US010759871B2

(12) United States Patent
Rao et al.

(10) Patent No.: US 10,759,871 B2
(45) Date of Patent: Sep. 1, 2020

(54) ANTIBODIES THAT BIND IL-4 AND/OR IL-13 AND THEIR USES

(71) Applicant: SANOFI, Paris (FR)

(72) Inventors: Ercole Rao, Morfelden-Waldorf (DE); Vincent Mikol, Charenton-le-Pont (FR); Danxi Li, Skillman, NJ (US); Jochen Kruip, Erzhausen (DE); Matthew Davison, Long Valley, NJ (US)

(73) Assignee: SANOFI, Paris (FR)

(*) Notice: Subject to any disclaimer, the term of this patent is extended or adjusted under 35 U.S.C. 154(b) by 383 days.

(21) Appl. No.: 15/645,765

(22) Filed: Jul. 10, 2017

(65) Prior Publication Data

US 2018/0030156 A1 Feb. 1, 2018

Related U.S. Application Data

(63) Continuation of application No. 13/831,862, filed on Mar. 15, 2013, now Pat. No. 9,732,162, which is a continuation of application No. 13/758,858, filed on Feb. 4, 2013, now abandoned, which is a continuation of application No. 12/682,864, filed as application No. PCT/US2008/079787 on Oct. 14, 2008, now Pat. No. 8,388,965.

(60) Provisional application No. 61/037,128, filed on Mar. 17, 2008.

(30) Foreign Application Priority Data

Oct. 15, 2007 (EP) .................................... 07291259

(51) Int. Cl.
*C07K 16/24* (2006.01)
*A61K 39/00* (2006.01)
*C07K 16/46* (2006.01)

(52) U.S. Cl.
CPC .......... *C07K 16/468* (2013.01); *C07K 16/244* (2013.01); *C07K 16/247* (2013.01); *A61K 39/00* (2013.01); *C07K 2317/31* (2013.01); *C07K 2317/64* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,179,337 A | 12/1979 | Davis et al. | |
| 4,256,746 A | 3/1981 | Miyashita et al. | |
| 4,275,149 A | 6/1981 | Litman et al. | |
| 4,294,757 A | 10/1981 | Asai | |
| 4,301,144 A | 11/1981 | Iwashita et al. | |
| 4,307,016 A | 12/1981 | Asai et al. | |
| 4,313,946 A | 2/1982 | Powell et al. | |
| 4,315,929 A | 2/1982 | Freedman et al. | |
| 4,318,980 A | 3/1982 | Boguslaski et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,376,110 A | 3/1983 | David et al. | |
| 4,424,219 A | 1/1984 | Hashimoto et al. | |
| 4,444,887 A | 4/1984 | Hoffmann | |
| 4,450,254 A | 5/1984 | Isley et al. | |
| 4,496,689 A | 1/1985 | Mitra | |
| 4,560,655 A | 12/1985 | Baker | |
| 4,640,835 A | 2/1987 | Shimizu et al. | |
| 4,657,866 A | 4/1987 | Kumar | |
| 4,670,417 A | 6/1987 | Iwasaki et al. | |
| 4,676,980 A | 6/1987 | Segal et al. | |
| 4,716,111 A | 12/1987 | Osband et al. | |
| 4,737,456 A | 4/1988 | Weng et al. | |
| 4,767,704 A | 8/1988 | Cleveland et al. | |
| 4,791,192 A | 12/1988 | Nakagawa et al. | |
| 4,816,397 A | 3/1989 | Boss et al. | |
| 4,816,567 A | 3/1989 | Cabilly et al. | |
| 4,946,778 A | 8/1990 | Ladner et al. | |
| 5,122,464 A | 6/1992 | Wilson et al. | |
| 5,122,469 A | 6/1992 | Mather et al. | |
| 5,223,409 A | 6/1993 | Ladner et al. | |
| 5,225,539 A | 7/1993 | Winter | |
| 5,314,995 A | 5/1994 | Fell, Jr. et al. | |
| 5,413,923 A | 5/1995 | Kucherlapati et al. | |

(Continued)

FOREIGN PATENT DOCUMENTS

EP 0 239 400 A2 9/1987
EP 0 332 424 A1 9/1989

(Continued)

OTHER PUBLICATIONS

Adey et al., Chapter 16, "Preparation of Second-Generation Phage Libraries", pp. 277-291, Phage Display of Peptides and Proteins, a Laboratory Manual, eds. Kay et al., Academic Press (1996).
Almawi et al. (1999) "Clinical Review 103: T Helper Type 1 and 2 Cytokines Mediate the Onset and Progression of Type I (Insulin-Dependent) Diabetes." The Journal of Clinical Endocrinology & Metabolism 84(5):1497-502.
Amit et al., "Three-dimensional structure of an antigen-antibody complex at 2.8 A resolution," 233(4765) Science 747-53 (1986).
Andrew et al., "Comparison of in Vitro Cell Binding Characteristics of Four Monoclonal Antibodies and Their Individual Tumor Localization Properties in Mice." Cancer Research 50:4423-28 (1990).

(Continued)

Primary Examiner — Elizabeth C. Kemmerer
Assistant Examiner — Regina M DeBerry
(74) Attorney, Agent, or Firm — Morrison & Foerster LLP

(57) ABSTRACT

The present invention relates to novel humanized anti-IL-4 and IL-13 antibodies and fragments thereof and novel bispecific antibodies and fragments thereof that specifically bind to IL-4 and IL-13. The invention also includes uses of the antibodies to treat or prevent IL-4 and/or IL-13 mediated diseases or disorders, including allergic asthma and dermatitis.

6 Claims, 2 Drawing Sheets

Specification includes a Sequence Listing.

(56) References Cited

U.S. PATENT DOCUMENTS

| | | |
|---|---|---|
| 5,474,981 A | 12/1995 | Leder et al. |
| 5,475,092 A | 12/1995 | Chari et al. |
| 5,530,101 A | 6/1996 | Queen et al. |
| 5,534,617 A | 7/1996 | Cunningham et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,585,499 A | 12/1996 | Chari et al. |
| 5,597,710 A | 1/1997 | Dalie et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,661,016 A | 8/1997 | Lonberg et al. |
| 5,698,417 A | 12/1997 | Robinson et al. |
| 5,698,435 A | 12/1997 | Robinson et al. |
| 5,705,154 A | 1/1998 | Dalie et al. |
| 5,712,163 A | 1/1998 | Parenteau et al. |
| 5,807,715 A | 9/1998 | Morrison et al. |
| 5,814,318 A | 9/1998 | Lonberg et al. |
| 5,846,545 A | 12/1998 | Chari et al. |
| 5,869,619 A | 2/1999 | Studnicka |
| 5,885,793 A | 3/1999 | Griffiths et al. |
| 5,916,771 A | 6/1999 | Hori et al. |
| 5,928,904 A | 7/1999 | Holmes et al. |
| 5,939,598 A | 8/1999 | Kucherlapati et al. |
| 5,989,830 A | 11/1999 | Davis et al. |
| 6,048,728 A | 4/2000 | Inlow et al. |
| 6,204,023 B1 | 3/2001 | Robinson et al. |
| 6,277,375 B1 | 8/2001 | Ward |
| 6,333,410 B1 | 12/2001 | Chari et al. |
| 6,514,496 B1 | 2/2003 | Platz et al. |
| 6,994,853 B1 | 2/2006 | Lindhofer et al. |
| 7,612,181 B2 | 11/2009 | Wu et al. |
| 8,388,965 B2 | 3/2013 | Rao et al. |
| 9,732,162 B2 | 8/2017 | Rao et al. |
| 9,738,728 B2 | 8/2017 | Rao et al. |
| 2002/0004587 A1 | 1/2002 | Miller et al. |
| 2002/0103345 A1 | 8/2002 | Zhu |
| 2002/0127231 A1 | 9/2002 | Schneck et al. |
| 2003/0130496 A1 | 7/2003 | Winter et al. |
| 2005/0002959 A1 | 1/2005 | Holmes et al. |
| 2005/0003403 A1 | 1/2005 | Rossi et al. |
| 2006/0063228 A1 | 3/2006 | Kasaian et al. |
| 2007/0071675 A1 | 3/2007 | Wu et al. |
| 2007/0104710 A1 | 5/2007 | Tomlinson et al. |
| 2009/0215092 A1 | 8/2009 | Love et al. |
| 2011/0217318 A1 | 9/2011 | Takayama et al. |
| 2012/0093830 A1 | 4/2012 | De Silva |
| 2013/0209469 A1 | 8/2013 | Rao et al. |
| 2013/0236461 A1 | 9/2013 | Rao et al. |
| 2013/0236463 A1 | 9/2013 | Rao et al. |
| 2013/0243776 A1 | 9/2013 | Rao et al. |
| 2013/0243777 A1 | 9/2013 | Rao et al. |
| 2013/0243778 A1 | 9/2013 | Rao et al. |
| 2013/0251716 A1 | 9/2013 | Rao et al. |
| 2013/0251717 A1 | 9/2013 | Rao et al. |
| 2013/0251718 A1 | 9/2013 | Rao et al. |
| 2013/0259866 A1 | 10/2013 | Rao et al. |
| 2014/0023649 A1 | 1/2014 | Rao et al. |
| 2014/0100359 A1 | 4/2014 | Wu et al. |
| 2016/0075777 A1 | 3/2016 | Carayon et al. |
| 2017/0029498 A1 | 2/2017 | Bender et al. |

FOREIGN PATENT DOCUMENTS

| | | |
|---|---|---|
| EP | 0 338 745 A1 | 10/1989 |
| EP | 0 396 387 A2 | 11/1990 |
| EP | 0 413 622 A1 | 2/1991 |
| EP | 0 439 095 A2 | 7/1991 |
| EP | 0 519 596 | 12/1992 |
| EP | 0 592 106 | 4/1994 |
| EP | 1 115 427 A1 | 12/2003 |
| EP | 1 115 427 B1 | 12/2003 |
| EP | 2573121 B1 | 8/2017 |
| EP | 2574629 B1 | 11/2017 |
| GB | 2403952 | 1/2005 |
| GB | 2430883 A | 4/2007 |
| JP | H09-502708 A | 3/1997 |
| JP | H09-510095 A | 10/1997 |
| RU | 2162711 C2 | 2/2001 |
| RU | 2295537 C2 | 3/2007 |
| WO | WO-86/05807 A1 | 10/1986 |
| WO | WO-87/05330 A1 | 9/1987 |
| WO | WO-89/01036 A1 | 2/1989 |
| WO | WO-89/09622 A1 | 10/1989 |
| WO | WO-89/12624 A2 | 12/1989 |
| WO | WO-89/12624 A3 | 12/1989 |
| WO | WO-91/09967 A1 | 7/1991 |
| WO | WO-91/10741 A1 | 7/1991 |
| WO | WO-91/14438 A1 | 10/1991 |
| WO | WO-92/01047 A1 | 1/1992 |
| WO | WO-92/08495 A1 | 5/1992 |
| WO | WO-93/08829 A1 | 5/1993 |
| WO | WO-93/11161 A1 | 6/1993 |
| WO | WO-93/15199 A1 | 8/1993 |
| WO | WO-93/15200 A1 | 8/1993 |
| WO | WO-93/16185 A2 | 8/1993 |
| WO | WO-93/16185 A3 | 8/1993 |
| WO | WO-93/21232 A1 | 10/1993 |
| WO | WO-93/21319 A1 | 10/1993 |
| WO | WO-94/25591 A1 | 11/1994 |
| WO | WO-95/07301 A1 | 3/1995 |
| WO | WO-95/09917 A1 | 4/1995 |
| WO | WO-96/33735 A1 | 10/1996 |
| WO | WO-96/34096 A1 | 10/1996 |
| WO | WO-97/14719 A1 | 4/1997 |
| WO | WO-97/33899 A1 | 9/1997 |
| WO | WO-97/34631 A1 | 9/1997 |
| WO | WO-97/34911 A1 | 9/1997 |
| WO | WO-98/16654 A1 | 4/1998 |
| WO | WO-98/23289 A1 | 6/1998 |
| WO | WO-98/24893 A2 | 6/1998 |
| WO | WO-98/24893 A3 | 6/1998 |
| WO | WO-98/46645 A2 | 10/1998 |
| WO | WO-98/46645 A3 | 10/1998 |
| WO | WO-98/50433 A2 | 11/1998 |
| WO | WO-98/50433 A3 | 11/1998 |
| WO | WO-00/64944 A1 | 11/2000 |
| WO | WO-01/77137 A1 | 10/2001 |
| WO | WO-01/77342 A1 | 10/2001 |
| WO | WO-01/90192 A2 | 11/2001 |
| WO | WO-01-90192 A3 | 11/2001 |
| WO | WO-02/08293 A2 | 1/2002 |
| WO | WO-02/08293 A3 | 1/2002 |
| WO | WO-03/035847 A2 | 5/2003 |
| WO | WO-03/035847 A3 | 5/2003 |
| WO | WO-03/038041 A2 | 5/2003 |
| WO | WO-03/038041 A3 | 5/2003 |
| WO | WO-03/092610 A2 | 11/2003 |
| WO | WO-03/092610 A3 | 11/2003 |
| WO | WO-2005/007699 A2 | 1/2005 |
| WO | WO-2005/007699 A3 | 1/2005 |
| WO | WO-2005/062967 A2 | 7/2005 |
| WO | WO-2005/062967 A3 | 7/2005 |
| WO | WO-2005/076990 A2 | 8/2005 |
| WO | WO-2005/076990 A3 | 8/2005 |
| WO | WO-2005/077042 A2 | 8/2005 |
| WO | WO-2005/077042 A3 | 8/2005 |
| WO | WO-2005/083440 A2 | 9/2005 |
| WO | WO-2005/083440 A3 | 9/2005 |
| WO | WO-2005/085284 A1 | 9/2005 |
| WO | WO-2005/113605 A1 | 12/2005 |
| WO | WO-2005/116077 A2 | 12/2005 |
| WO | WO-2005/116077 A3 | 12/2005 |
| WO | WO-2005/123126 A2 | 12/2005 |
| WO | WO-2005/123126 A3 | 12/2005 |
| WO | WO-2006/042333 A2 | 4/2006 |
| WO | WO-2006/042333 A3 | 4/2006 |
| WO | WO-2007/045477 A2 | 4/2007 |
| WO | WO-2007/045477 A3 | 4/2007 |
| WO | WO-2007/080174 A2 | 7/2007 |
| WO | WO02007/080174 A3 | 7/2007 |
| WO | WO-2007/085815 A2 | 8/2007 |

(56) References Cited

FOREIGN PATENT DOCUMENTS

| WO | WO-2007/085815 A3 | 8/2007 |
| --- | --- | --- |
| WO | WO-2007/107349 A1 | 9/2007 |
| WO | WO-2009/052081 A2 | 4/2009 |
| WO | WO-2009/052081 A3 | 4/2009 |
| WO | WO-2015/198146 A2 | 12/2015 |

OTHER PUBLICATIONS

Aplin & Wriston, "Preparation, properties, and applications of carbohydrate conjugates of proteins and lipids," 10(4) CRC Crit Rev Biochem 259-306 (1981).
Arnon et al., "Monoclonal Antibodies for Immunotargeting of Drugs in Cancer Therapy" in Monoclonal Antibodies and Cancer Therapy: Proceedings of the Roche-UCLA Symposium, 243-56 (Reisfeld and Sell eds., 1985).
Aversa et al., "An interleukin 4 (IL-4) mutant protein inhibits both IL-4 or IL-13-induced human immunoglobulin G4 (IgG4) and IgE synthesis and B cell proliferation: support for a common component shared by IL-4 and IL-13 receptors," 178(6) J Exp Med 2213-18 (1993).
Barbas et al., "In vitro evolution of a neutralizing human antibody to human immunodeficiency virus type 1 to enhance affinity and broaden strain cross-reactivity," 91(9) Proc Nat'l Acad Sci USA 3809-13 (1994).
Barbas et al., "Assembly of combinatorial antibody libraries on phage surfaces: the gene III site," 88(18) Proc Nat'l Acad Sci USA 7978-82 (1991).
Barnes et al., "Methods for growth of cultured cells in serum-free medium," 102(2) Anal Biochem 255-70 (1980).
Bass et al., "Hormone phage: an enrichment method for variant proteins with altered binding properties," 8(4) Proteins 309-14 (1990).
Biolegend: "Purified anti-human IL-4", Product Data Sheet, Nov. 30, 2012 (Nov. 30, 2012), Retrieved from the Internet: URL:http://www.biolegend.com/purified-anti-human-il-4-antibody-1 018.html [retrieved on Feb. 11, 2013].
Biolegend. (Feb. 21, 2007). "Cross Reactive Species Reference Chart", located at http://www.biolgend.com/media_assets/support_resource/bioLegend_Cross-Reactivity_Chartv2, pdf >, one page.
Birch & Racher, "Antibody production," 58(5-6) Adv Drug Del Rev 671-685 (2006).
Bird et al, "Single-chain antigen-binding proteins," 242(4877) Science 423-6 (1988).
Bird et al. (1991). "Development of immunoassays for human interleukin 3 and interleukin 4, some of which discriminate between different recombinant DNA-derived molecules," Cytokine 3(6):562-567.
Boder et al., "Directed evolution of antibody fragments with monovalent femtomolar antigen-binding affinity," 97(20) Proc Nat'l Acad Sci USA 10701-5 (2000).
Bodey et al., "Failure of cancer vaccines: the significant limitations of this approach to immunotherapy", Anticancer Research 20(4):2665-76 (2000).
Boerner et al., "Production of antigen-specific human monoclonal antibodies from in vitro-primed human splenocytes," 147(1) J Immunol 86-95 (1991).
Brennan et al., "Preparation of bispecific antibodies by chemical recombination of monoclonal immunoglobulin G1 fragments," 229(4708): 81-83 Science (1985).
Brodeur et al., "Mouse-Human Myeloma Partners for the Production of Heterohybridomas," in Monoclonal Antibody Production Techniques and Applications, Chapter4:51-63 (LB Schook ed. 1$^{st}$ ed. 1987).
Brooks et al., "CHARMM: A program for macromolecular energy, minimization, and dynamics calculations," 4(2) J Computational Chemistry 187-217 (1983).

Brüggemann et al., "Designer mice: the production of human antibody repertoires in transgenic animals," 7 Year in Immunol 33-40 (1993).
Buchwald et al., "Long-term, continuous intravenous heparin administration by an implantable infusion pump in ambulatory patients with recurrent venous thrombosis," 88(4) Surgery 507-16 (1980).
Caron et al., "Engineered humanized dimeric forms of IgG are more effective antibodies," 176(4) J Exp Med 1191-5(1992).
Carter et al., "Toward the production of bispecific antibody fragments for clinical applications," 4(5) J Hematother 463-70 (1995).
Carter, "Bispecific human IgG by design," 248(1-2) J Immunol Methods 7-15 (2001).
Carter et al., "Humanization of an anti-p185HER2 antibody for human cancer therapy," 89(10) Proc Nat'l Acad Sci USA 4285-9 (1992).
Carter et al., "High level Escherichia coli expression and production of a bivalent humanized antibody fragment," 10(2) Biotechnology 163-7 (1992).
Case et al., "The Amber biomolecular simulation programs," 26(16) J Computational Chemistry 1668-88 (2005).
Casset et al., "A peptide mimetic of an anti-CD4 monoclonal antibody by rational design" Biochemical and Biophysical Research Communication 307:198-205 (2003).
Chang et al., "Phenotypic expression in E. coli of a DNA sequence coding for mouse dihydrofolate reductase," 275(5681) Nature 615-24 (1978).
Chatterjee et al., "Idiotypic antibody immunotherapy of cancer", Cancer Immunology and Immunotherapy 38(2):75-82 (1994).
Chothia et al., "Canonical structures for the hypervariable regions of immunoglobulins," 196(4) J Mol Biol 901-17 (1987).
Clackson et al., "Making antibody fragments using phage display libraries," 352(6336) Nature 624-28 (1991).
Cockett et al., "High level expression of tissue inhibitor of metalloproteinases in Chinese hamster ovary cells using glutamine synthetase gene amplification," 8(7) Biotechnology 662-7 (1990).
Colbére-Garapin et al., "A new dominant hybrid selective marker for higher eukaryotic cells," 150(1) J Mol Biol 1-14 (1981).
Cole et al. (1985). "The EBV-hybridoma technique and its application to human lung cancer," in Monoclonal Antibodies and Cancer Therapy: Proceedings of the Roche-UCLA Symposium 77-96.
Coppola et al., "Enforced expression of KDR receptor promotes proliferation, survival and megakaryocytic differentiation of TF1 progenitor cell line," Cell Death Differ. 13(1):61-74 (Jan. 2006).
Cote et al., "Generation of human monoclonal antibodies reactive with cellular antigens," 80(7) Proc Nat'l Acad Sci USA 2026-39 (1983).
Creighton, Proteins: Structure and Molecular Properties, W.H. Freeman &Co., New York, pp. 78-87 (1$^{st}$ Edition, 1984).
Crouse et al., "Expression and amplification of engineered mouse dihydrofolate reductase minigenes," 3(2) Mol Cell Biol 257-66 (1983).
Cunningham & Wells, "High-resolution epitope mapping of hGH-receptor interactions by alanine-scanning mutagenesis," 244(4908) Science 1081-5 (1989).
Cunningham & Wells, "Rational design of receptor-specific variants of human growth hormone," 88(8) Proc Nat'l Acad Sci USA 3407-11 (1991).
Cwirla et al., "Peptides on phage: a vast library of peptides for identifying ligands," 87(16) Proc Nat'l Acad Sci USA 6378-82 (1990).
Davies & Riechmann, "Affinity improvement of single antibody VH domains: residues in all three hypervariable regions affect antigen binding," 2(3) Immunotechnology 169-79 (1996).
Definition of "Treating" or "To Treat," The American Heritage® Medical Dictionary (2007), retrieved Aug. 3, 2015 from http://medical-dictionary.thefreedictionary.com/treating. pp. 1-3.
Defrance et al., "Interleukin 13 is a B cell stimulating factor," 179(1) J Exp Med 135-43 (1994).
De Gruijl & Curiel, "Cancer vaccine strategies get bigger and better" Nature Medicine 5(10):1124-25 (1999).

(56) References Cited

OTHER PUBLICATIONS

De Kruif & Logtenberg, "Leucine zipper dimerized bivalent and bispecific scFv antibodies from a semi-synthetic antibody phage display library," 270(13) J Biol Chem 7630-4 (1996).
Dermer, G.B. "Another anniversary for the war on cancer." Bio/Technology, 12(3):320 (1994).
Derocq et al., "Interleukin-13 stimulates interleukin-6 production by human keratinocytes. Similarity with interleukin-4," 343(1) FEBS Lett 32-6 (1994).
Devlin et al., "No excess of homozygosity at loci used for DNA fingerprinting," 249(4975) Science 1416-20 (1990).
De Waal Malefyt et al., "Effects of IL-13 on phenotype, cytokine production, and cytotoxic function of human monocytes. Comparison with IL-4 and modulation by IFN-gamma or IL-10," 151(11) J Immunol 6370-381 (1993).
Diaclone: "Diaclone Monoclonal Antibody Cataloge 2004-2005", pp. 1-28, 2004. Retrieved from the Internet: URL:http://www.cellsciences.com/PDF/ DiacloneMAbCatalog.pdf [retrieved on Feb. 13, 2013].
Donnelly, "Cancer vaccine targets leukemia", Nature Medicine 9(11):1354-56 (2003).
Doyle et al., "Interleukin-13 alters the activation state of murine macrophages in vitro: comparison with interleukin-4 and interferon-gamma," 24(6) Eur J Immunol 1441-5 (1994).
Duchosal et al., "Immunization of hu-PBL-SCID mice and the rescue of human monoclonal Fab fragments through combinatorial libraries," 355(6357) Nature 258-62 (1992).
During et al., "Controlled release of dopamine from a polymeric brain implant: in vivo characterization," 25(4) Ann Neurol 351-6 (1989).
Edge et al., "Deglycosylation of glycoproteins by trifluoromethanesulfonic acid," 118(1) Anal Biochem 131-7 (1981).
Ezzell, "Cancer 'Vaccines': An Idea Whose Time Has Come?", J NIH Research 7:46-49 (1995).
Fell et al., "Genetic construction and characterization of a fusion protein consisting of a chimeric F(ab') with specificity for carcinomas and human IL-2," 146(7) J Immunol 2446-52 (1991).
Fior et al., "Interleukin-13 gene expression by malignant and EBV-transformed human B lymphocytes," 5(6) Eur Cytokine Network 593-600 (1994).
Fleer et al., "High-level secretion of correctly processed recombinant human interleukin-1 beta in Kluyveromyces lactis," 107(2) Gene 285-95 (1991).
Foecking et al., "Powerful and versatile enhancer-promoter unit for mammalian expression vectors," 45(1) Gene 101-5 (1986).
Forni et al., "Immunoprevention of cancer: is the time ripe?", Cancer Research 60(10):2571-75 (2000).
Foster, P.S. et al. (2002). "Interleukins-4, -5, and -13: Emerging Therapeutic Targets in Allergic Disease," *Pharmacology & Theapeutics*. 94(3): 253-64.
Freedberg et al., "Flexibility and Function in HIV Protease: Dynamics of the HIV-1 Protease Bound to the Asymmetric Inhibitor Kynostatin 272 (KNI-272)," 120(31) J Am Chem Soc 7916-23 (1998).
Freshney, R.I. Culture of Animal Cells, a Manual of Basic Technique, pp. 3-4; Alan R. Liss, Inc., New York (1983).
Furukawa et al., "A role of the third complementarity-determining region in the affinity maturation of an antibody," 276(29) J Biol Chem 27622-8 (2001).
Gauvreau et al., "Effects of interleukin-13 blockade on allergen-induced airway responses in mild atopic asthma." American Journal of Respiratory and Critical Care Medicine, 183(8):1007-14 (2011).
Garrard et al., "Fab assembly and enrichment in a monovalent phage display system," 9(12) Biotechnology 1373-7 (1991).
Gentz et al., "Bioassay for trans-activation using purified human immunodeficiency virus tat-encoded protein: trans-activation requires mRNA synthesis," 86(3) Proc Nat'l Acad Sci USA 821-4 (1989).
Gillies et al., "Antibody-targeted interleukin 2 stimulates T-cell killing of autologous tumor cells," 89(4) Proc Nat'l Acad Sci USA 1428-32 (1992).
Gillies et al., "High-level expression of chimeric antibodies using adapted cDNA variable region cassettes," 125(1-2) J Immunol Methods 191-202 (1989).
Goding, "Production of Monoclonal Antibodies," in Monoclonal Antibodies: Principles and Practice, Chapter3:59-103 ($2^{nd}$ Ed., 1986).
Goeddel et al., "Direct expression in *Escherichia coli* of a DNA sequence coding for human growth hormone," 281(5732) Nature 544-8 (1979).
Goeddel et al., "Synthesis of human fibroblast interferon by *E. coli*," 8(18) Nucl Acids Res 4057-74 (1980).
Gram et al., "In vitro selection and affinity maturation of antibodies from a naive combinatorial immunoglobulin library," 89(8) Proc Nat'l Acad Sci USA 3576-80 (1992).
Grünberg et al., "Flexibility and conformational entropy in protein-protein binding," 14(12) Structure 683-93 (2006).
Grünig, G. et al. (Dec. 18, 1998). "Requirement for IL-13 Independently of IL-4 in Experimental Asthma," *Science* 282(5397): 2261-63.
Guss et al., "Structure of the IgG-binding regions of streptococcal protein G," 5(7) EMBO J 1567-75 (1986).
Hakimuddin et al., "A chemical method for deglycosylation of proteins," 259(1) Arch Biochem Biophys 52-7 (1987).
Ham & McKeehan, "Media and growth requirements," 58 Meth Enzymol 44-93 (1979).
Harris et al., "Commercial manufacturing scale formulation and analytical characterization of therapeutic recombinant antibodies," 61(3) Drug Dev Res 137-54 (2004).
Hart et al., "Preclinical efficacy and safety of pascolizumabe (SB 240683): A humanized anti-interleukin-4 antibody with therapeutic potential in asthma," Clinical and Experimental Immunology 103(1) 93-100 (2002).
Hawkins et al., "Selection of phage antibodies by binding affinity: Mimicking affinity maturation," 226(3) J Mol Biol 889-96 (1992).
Heinzmann et al., "Genetic variants of IL-13 signalling and human asthma and atopy," 9(4) Hum Mol Genet 549-59 (2000).
Hellström et al., "Antibodies for Drug Delivery," in Controlled Drug Delivery: Fundamentals and Applications, Chapter 15:623-53 (Robinson & Lee eds., $2^{nd}$ ed. 1987).
Herbert et al., "IL-4 and IL-13 exhibit comparable abilities to reduce pyrogen-induced expression of procoagulant activity in endothelial cells and monocytes," 328(3) FEBS Lett 268-70 (1993).
Hinnen et al., "Transformation of yeast," 75(4) Proc Nat'l Acad Sci USA 1929-33 (1978).
Hitzeman et al., "Isolation and characterization of the yeast 3-phosphoglycerokinase gene (PGK) by an immunological screening technique," 255(24) J Biol Chem 12073-80 (1980).
Holland & Holland, "Isolation and identification of yeast messenger ribonucleic acids coding for enolase, glyceraldehyde-3-phosphate dehydrogenase, and phosphoglycerate kinase," 17(23) Biochemistry 4900-7 (1978).
Holliger et al., ""Diabodies": small bivalent and bispecific antibody fragments," 90(14) Proc Nat'l Acad Sci USA 6444-8 (1993).
Hostettler, K.E. et al. (Dec. 12, 2014). "Anti-fibrotic effects of nintedanib in lung fibroblasts derived from patients with idiopathic pulmonary fibrosis," *Respiratory Research* 15(1):157.
Howard et al., "Intracerebral drug delivery in rats with lesion-induced memory deficits," 71(1) J Neurosurg 105-12 (1989).
Hudson & Kortt, "High avidity scFv multimers; diabodies and triabodies," 231(1-2) J Immunol Methods 177-89 (1999).
Hudson, "Recombinant antibody constructs in cancer therapy," 11(5) Current Opinion in Immunology 548-57 (1999).
Huston et al., "Protein engineering of antibody binding sites: recovery of specific activity in an anti-digoxin single-chain Fv analogue produced in *Escherichia coli*," 85(16) Proc Nat'l Acad Sci USA 5879-83 (1988).
Jackson et al., "Review series on helminths, immune modulation and the hygiene hypothesis: Immunity against helminths and immunological phenomena in modern human populations: coevolutionary legacies?" Immunology 126(1):18-27 (2008).
Jakobovits et al., "Analysis of homozygous mutant chimeric mice: deletion of the immunoglobulin heavy-chain joining region blocks B-cell development and antibody production," 90(6) Proc Nat'l Acad Sci USA 2551-5 (1993).

(56) References Cited

OTHER PUBLICATIONS

Jakobovits et al., "Germ-line transmission and expression of a human-derived yeast artificial chromosome," 362(6417) Nature 255-8 (1993).
James et al., "Antibody multispecificity mediated by conformational diversity," 299(5611) Science 1362-7 (2003).
Jespers et al., "Guiding the selection of human antibodies from phage display repertoires to a single epitope of an antigen," 12(9) Biotechnology 899-903 (1994).
Jones et al., "Replacing the complementarity-determining regions in a human antibody with those from a mouse," 321(6069) Nature 522-5 (1986).
Kasaian et al., "Efficacy of IL-13 Neutralization in a Sheep Model of Experimental Asthma", American Journal of Respiratory Cell and Molecular Biology, 36(3):368-376 (2007).
Köhler, "Immunoglobulin chain loss in hybridoma lines," 77(4) Proc Nat'l Acad Sci USA 2197-9 (1980).
Köhler & Milstein, "Continuous cultures of fused cells secreting antibody of predefined specificity." 256(5517) Nature 495-7 (1975).
Kostelny et al., "Formation of a bispecific antibody by the use of leucine zippers," 148(5) J Immunol 1547-53 (1992).
Kozbor & Roder, "The production of monoclonal antibodies from human lymphocytes," 4(3) Immunology Today 72-9 (1983).
Kozbor et al., "A human hybrid myeloma for production of human monoclonal antibodies," 133(6) J Immunol 3001-5 (1984).
Kufer et al., "A revival of bispecific antibodies," 22(5) Trends Biotech 238-44 (2004).
Kundu et al., "Dynamics of proteins in crystals: comparison of experiment with simple models," 83(2) Biophys J 723-32 (2002).
Kunkel, "Rapid and efficient site-specific mutagenesis without phenotypic selection," 82(2) Proc Nat'l Acad Sci USA 488-92 (1985).
Kutemeier et al., "Assembly of humanized antibody genes from synthetic oligonucleotides using a single-round PCR," 17(2) BioTechniques 242-6 (1994).
Langer, "New methods in drug delivery," 249(4976) Science 1527-33 (1990).
Langer & Peppas, "Chemical and Physical Structure of Polymers as Carriers for Controlled Release of Bioactive Agents: A Review," C23(1) J Macromol Sci Rev Macromol Chem 61-126 (1983).
Lazar et al., "A molecular immunology approach to antibody humanization and functional optimization," 44(8) Mol Immunol 1986-1988 (2007).
Ledru, E. et al. (Apr. 15, 2003). "A Nonsecreted Variant of Interleukin-4 is Associated with Apoptosis: Implication for the T Helper-2 Polarization in HIV Infection," *Blood* 101(8):3102-3105.
Lehtonen, S.T. et al. (2016). "Pirfenidone and nintedanib modulate properties of fibroblasts and myofibroblasts in idiopathic pulmonary fibrosis," *Respiratory Research* 17:14, pp. 1-12.
Lee et al., "Increased vaccine-specific T cell frequency after peptide-based vaccination correlates with increased susceptibility to in vitro stimulation but does not lead to tumor regression'" Journal of Immunology 163(11):6292-6300 (1999).
Lefort et al., "IL-13 and IL-4 share signal transduction elements as well as receptor components in TF-1 cells," 366(1-2) FEBS Lett 122-6 (1995).
Levy et al., "Inhibition of calcification of bioprosthetic heart valves by local controlled-release diphosphonate," 228(4696) Science 190-2 (1985).
Lindmark et al., "Binding of immunoglobulins to protein A and immunoglobulin levels in mammalian sera," 62(1) J Immunol Methods 1-13 (1983).
Liu et al., "Characterization of the stability of a fully human monoclonal IgG after prolonged incubation at elevated temperature," 837(1-2) J Chromatog B 35-43 (2006).
Lonberg & Huszar, "Human antibodies from transgenic mice," 13(1) Int Rev Immunol 65-93 (1995).

Lopez-Berestein, "Treatment of Systemic Fungal Infections with Liposomal-Amphotericin B," in Liposomes in the Therapy of Infectious Disease and Cancer, 317-27 (Lopez-Berestein et al., eds., 1989).
Lowman & Wells, "Affinity maturation of human growth hormone by monovalent phage display," 234(3) J Mol Biol 564-78 (1993).
Lowman et al., "Selecting high-affinity binding proteins by monovalent phage display," 30(45) Biochemistry 10832-8 (1991).
Lowy et al., "Isolation of transforming DNA: cloning the hamster aprt gene," 22(3) Cell 817-23 (1980).
Lu et al., "Di-diabody: a novel tetravalent bispecific antibody molecule by design," J. Immunol. Methods 279(1-2):219-32 (2003).
Lu et al., "Simultaneous blockade of both the epidermal growth factor receptor and the insulin-like growth factor receptor signaling pathways in cancer cells with a fully human recombinant bispecific antibody." J Biol Chem. 279(4):2856-65 (2004).
Lu et al., "A fully human recombinant IgG-like bispecific antibody to both the epidermal growth factor receptor and the insulin-like growth factor receptor for enhanced antitumor activity," J. Biol. Chem. 280(20):19665-72 (2005).
Luckow & Summers, "Trends in the development of baculorvirus expression vectors," 6 Nature Biotechnology 47-55 (1988).
Ma et al., "Multiple diverse ligands binding at a single protein site: A matter of pre-existing populations," 11(2) Protein Science 184-7 (2002).
Mack et al., "A small bispecific antibody construct expressed as a functional single-chain molecule with high tumor cell cytotoxicity," 92(15) Proc Nat'l Acad Sci USA 7021-5 (1995).
Mackerell et al., "The Encyclopedia of Computational Chemistry," vol. 1:271-177 (Schleyer et al., eds. 1998).
Maeda et al., "Production of human alpha-interferon in silkworm using a baculovirus vector," 315(6020) Nature 592-4 (1985).
Mallender & Voss, "Construction, expression, and activity of a bivalent bispecific single-chain antibody," 269(1) J Biol Chem 199-206 (1994).
Marks et al., "By-passing immunization. Human antibodies from V-gene libraries displayed on phage," 222(3) J Mol Biol 581-97 (1991).
Marks et al., "By-passing immunization: building high affinity human antibodies by chain shuffling," 10(7) Biotechnology 779-83 (1992).
McCafferty et al., "Phage antibodies: filamentous phage displaying antibody variable domains," 348(6301) Nature 552-4 (1990).
McKenzie et al., "Interleukin 13, a T-cell-derived cytokine that regulates human monocyte and B-cell function," 90(8) Proc Nat'l Acad Sci USA 3735-9 (1993).
Miller et al. "An Insect Baculovirus Host-vector System for High-level Expression of Foreign Genes," Genetic Engineering: Principles and Methods, vol. 8:277-98 (Setlow et al, eds., 1986).
Miller et al., "Design, construction, and in vitro analyses of multivalent antibodies," 170(9) J Immunol 4854-61 (2003).
Milstein & Cuello, "Hybrid hybridomas and their use in immunohistochemistry," 305(5934) Nature 537-40 (1983).
Minty et al., "Interleukin-13 is a new human lymphokine regulating inflammatory and immune responses," 362(6417) Nature 248-50 (1993).
Minty, "Interleukin-13" in Cytokines in Health and Disease, Chapter 13:185-97 (Remick and Friedland, eds., $2^{nd}$ ed. 1997).
Montaner et al., "Interleukin 13 inhibits human immunodeficiency virus type 1 production in primary blood-derived human macrophages in vitro," 178(2) J Exp Med 743-7 (1993).
Morimoto & Inouye, "Single-step purification of F(ab')2 fragments of mouse monoclonal antibodies (immunoglobulins G1) by hydrophobic interaction high performance liquid chromatography using TSKgel Phenyl-5PW ," 24(1-2) J Biochem Biophys Methods 107-17 (1992).
Morrison, "Transfectomas provide novel chimeric antibodies," 229(4719) Science 1202-7 (1985).
Morrison et al., "Chimeric human antibody molecules: mouse antigen-binding domains with human constant region domains," 81(21) Proc Nat'l Acad Sci USA 6851-5 (1984).

(56) References Cited

OTHER PUBLICATIONS

Muller et al., "The first constant domain (CH1 and CL) of an antibody used as heterodimerization domain for bispecific miniantibodies." FEBS Letters 422:259-64 (1998).
Mulligan & Berg, "Selection for animal cells that express the *Escherichia coli* gene coding for xanthine-guanine phosphoribosyltransferase," 78(4) Proc Nat'l Acad Sci USA 2072-6 (1981).
Munson & Rodbard, "Ligand: a versatile computerized approach for characterization of ligand-binding systems," 107(1) Anal Biochem 220-39 (1980).
Murata et al., "Sharing of receptor subunits and signal transduction pathway between the IL-4 and IL-13 receptor system," 69(1) Int J Hematol 13-20 (1999).
Muzio et al., "Interleukin-13 induces the production of interleukin-1 receptor antagonist (IL-1ra) and the expression of the mRNA for the intracellular (keratinocyte) form of 1L-1ra in human myelomonocytic cells," 83(7) Blood 1738-43 (1994).
Naramura et al., "Mechanisms of cellular cytotoxicity mediated by a recombinant antibody-IL2 fusion protein against human melanoma cells," 39(1) Immunol Lett 91-9 (1994).
Ngoc et al., "Cytokines, allergy, and asthma," 5(2) Curr Opin Allergy Clin Immunology 161-6 (2005).
Nisonoff et al., "Separation of univalent fragments from the bivalent rabbit antibody molecule by reduction of disulfide bonds," 89 Arch Biochem Biophys 230-44 (1960).
Ohno et al., "Antigen-binding specificities of antibodies are primarily determined by seven residues of VH", Proc. Natl. Acad. Sci. USA, 82:2945-49 (1985).
Oi & Morrison, "Chimeric antibodies," 4 BioTechniques 214-221 (1986).
O'Hare et al., "Transformation of mouse fibroblasts to methotrexate resistance by a recombinant plasmid expressing a prokaryotic dihydrofolate reductase," 78(3) Proc Nat'l Acad Sci USA 1527-31 (1981).
Order, "Analysis, Results, and Future Prospective of the Therapeutic Use of Radiolabeled Antibody in Cancer Therapy," in Monoclonal Antibodies for Cancer Detection and Therapy 303-16 (Baldwin and Byers, eds., 1985).
Padlan, "A possible procedure for reducing the immunogenicity of antibody variable domains while preserving their ligand-binding properties," 28(4-5) Molecular Immunology 489-98 (1991).
Panka et al., "Variable region framework differences result in decreased or increased affinity of variant anti-digoxin antibodies," Immunology 85:3080-84 (1988).
Parham, "On the fragmentation of monoclonal IgG1, IgG2a, and IgG2b from BALB/c mice," 131(6) J Immunol 2895-2902 (1983).
Paul, W.E., Fundamental Immunology 3$^{rd}$ Ed. Fv Structure and Diversity in Three Dimensions: pp. 292-95 Raven Press, NY 1993.
Pearson & Lipman "Improved tools for biological sequence comparison," 85(8) Proc Nat'l Acad Sci USA 2444-8 (1988).
Pham et al., "De novo proteomic sequencing of a monoclonal antibody raised against OX40 ligand," 352(1) Anal Biochem 77-86 (2006).
Plückthun & Pack, "New protein engineering approaches to multivalent and bispecific antibody fragments," 3(2) Immunotechnology 83-105 (1997).
Presta et al., "Humanization of an antibody directed against IgE," 151(5) J Immunol 2623-32 (1993).
Proudfoot, "Transcriptional interference and termination between duplicated alpha-globin gene constructs suggests a novel mechanism for gene regulation," 322(6079) Nature 562-5 (1986).
Punnonen et al., "Interleukin 13 induces interleukin 4-independent IgG4 and IgE synthesis and CD23 expression by human B cells," 90(8) Proc Nat'l Acad Sci USA 3730-4 (1993).
Queen et al., "A humanized antibody that binds to the interleukin 2 receptor." Proc Natl Acad Sci U.S.A. 86(24):10029-33 (1989).
Rader et al., "A phage display approach for rapid antibody humanization: designed combinatorial V gene libraries," 95(15) Proc Nat'l Acad Sci USA 8910-5 (1998).
Riechmann et al., "Reshaping human antibodies for therapy," 332(6162) Nature 323-7 (1988).
Rizzo et al., "Validation of a model for the complex of HIV-1 reverse transcriptase with Sustiva through computation of resistance profiles," 122(51) J Am Chem Soc 12898-12900 (2000).
Roberts et al., "An integrated strategy for structural characterization of the protein and carbohydrate components of monoclonal antibodies: application to anti-respiratory syncytial virus MAb," 67(20) Anal Chem 3613-25 (1995).
Roguska et al., "Humanization of murine monoclonal antibodies through variable domain resurfacing," 91(3) Proc Nat'l Acad Sci USA 969-73 (1994).
Rosenberg et al., "Vectors for selective expression of cloned DNAs by T7 RNA polymerase," 56(1) Gene 125-35 (1987).
Roy et al., "Beneficial effect of anti-interleukin-4 antibody when administered in a murine model of tuberculosis infection." Tuberculosis, 88(3):197-202 (2008).
Rudikoff et al., "Single amino acid substitution altering antigen-binding specificity" Proc. Natl. Acad. Sci. 79(6):1979-83 (1982).
Sanger et al., "DNA sequencing with chain-terminating inhibitors," 74(12) Proc Nat'l Acad Sci USA 5463-7 (1977).
Santerre et al., "Expression of prokaryotic genes for hygromycin B and G418 resistance as dominant-selection markers in mouse L cells," 30(1-3) Gene 147-56 (1984).
Saudek et al., "A preliminary trial of the programmable implantable medication system for insulin delivery," 321(9) N Engl J Med 574-9 (1989).
Sefton, "Implantable pumps," 14(3) Crit Rev Biomed Eng 201-40 (1987).
Schoepfer, "The pRSET family of T7 promoter expression vectors for *Escherichia coli*," 124(1) Gene 83-5 (1993).
Scott & Smith, "Searching for peptide ligands with an epitope library," 249(4967) Science 386-90 (1990).
Shen et al., "Single Variable Domain-IgG Fusion: A Novel Recombinant Approach to Fc Domain-Containing BiSpecific Antibodies." J Biol Chem. 281(16): 10706-14 (2006).
Shopes, "A genetically engineered human IgG mutant with enhanced cytolytic activity," 148(9) J Immunol 2918-22 (1992).
Short et al., "Complementary combining site contact residue mutations of the anti-digoxin Fab 26-10 permit high affinity wild-type binding," 277(19) J Biol Chem 16365-70 (2002).
Sims et al., "A humanized CD18 antibody can block function without cell destruction," 151(4) J Immunol 2296-308 (1993).
Skerra & Plückthun, "Assembly of a functional immunoglobulin Fv fragment in *Escherichia coli*," 240(4855) Science 1038-41 (1988).
Smith, "Filamentous fusion phage: novel expression vectors that display cloned antigens on the virion surface," 228(4705) Science 1315-7 (1985).
Sozzani et al., "Interleukin-13 inhibits protein kinase C-triggered respiratory burst in human monocytes. Role of calcium and cyclic AMP," 270(10 J Biol Chem 5084-8 (1995).
Spring & Nisonoff et al., "Allotypic markers on Fab fragments of mouse immunoglobulins," 113(2) J Immunol 470-8 (1974).
Staerz et al., "Hybrid antibodies can target sites for attack by T cells," 314(6012) Nature 628-31 (1985).
Stevenson et al., "A chimeric antibody with dual Fc regions (bisFabFc) prepared by manipulations at the IgG hinge," 3(4) Anticancer Drug Des 219-30 (1989).
Studnicka et al., "Human-engineered monoclonal antibodies retain full specific binding activity by preserving non-CDR complementarity-modulating residues," 7(6) Protein Engineering 805-14 (1994).
Studier, "Use of bacteriophage T7 lysozyme to improve an inducible T7 expression system," 219(1) J Mol Biol 37-44 (1991).
Sundberg & Mariuzza, "Luxury accommodations: the expanding role of structural plasticity in protein-protein interactions," 8(7) Structure R137-R142 (2000).
Suresh et al., "Bispecific monoclonal antibodies from hybrid hybridomas," 121 Meth Enzym 210-28 (1986).
Szybalska & Szybalski, "Genetics of human cell lines IV. DNA-mediated heritable transformation of a biochemical trait," 48(12) Proc Nat'l Acad Sci USA 2026-34 (1962).
Takahashi et al., "Human Fas ligand: gene structure, chromosomal location and species specificity," 6(10) Int Immunol 1567-74 (1994).

(56) References Cited

OTHER PUBLICATIONS

Tanaka et al., "Interleukin-6, in Cytokine Regulation of Humoral Immunity: Basic and Clinical Aspects," Chapter10:251-272 (Snapper, ed. 1996).
Thompson et al., "Affinity maturation of a high-affinity human monoclonal antibody against the third hypervariable loop of human immunodeficiency virus: use of phage display to improve affinity and broaden strain reactivity," 256(1) J Mol Biol 77-88 (1996).
Thornton et al., "Protein structure. Prediction of progress at last," 354 (6349) Nature 105-6 (1991).
Thotakura & Bahl, "Enzymatic deglycosylation of glycoproteins," 138 Meth Enzymol 350-9 (1987).
Todorovska et al., "Design and application of diabodies, triabodies and tetrabodies for cancer targeting," 248(1-2) J Immunol Methods 47-66 (2001).
Thorpe & Ross, "The preparation and cytotoxic properties of antibody-toxin conjugates," 62 Immunol Rev 119-58 (1982).
Thorpe, "Antibody Carriers of Cytotoxic Agents in Cancer Therapy: A Review," in Monoclonal Antibodies '84: Biological and Clinical Applications, 475-506 (Pinchera et al. eds., 1985).
Traunecker et al., "Bispecific single chain molecules (Janusins) target cytotoxic lymphocytes on HIV infected cells," 10(12) EMBO J 3655-9 (1991).
Treat et al., "Liposome Encapsulated Doxorubicin Preliminary Reuslts of Phase I and Phase II Trials," in Liposomes in the Therapy of Infectious Disease and Cancer, 353-65 (Lopez-Berestein et al., eds., 1989).
Trkola et al., "In Vivo Efficacy of Human Immunodeficiency Virus Neutralizing Antibodies: Estimates for Protective Titers." Journal of Virology 82(3):1591-99 (2008).
Urlaub & Chasin, "Isolation of Chinese hamster cell mutants deficient in dihydrofolate reductase activity," 77(7) Proc Nat'l Acad Sci USA 4216-20 (1980).
Valadon et al., "Screening phage display libraries for organ-specific vascular immunotargeting in vivo," Proc. Nat'l Acad. Sci. 103(2):407-12 (2006).
Vaughan et al., "Human antibodies by design," 16(6) Nature Biotechnology 535-9 (1998).
Verhoeyen et al., "Reshaping human antibodies: grafting an antilysozyme activity," 239(4847) Science 1534-6 (1988).
Verma et al., "Bispecific antibodies and their use in applied research." Vet. World 5(12):775-80 (2012).
Vita et al., "Characterization and comparison of the interleukin 13 receptor with the interleukin 4 receptor on several cell types," 270(8) J Biol Chem 3512-7 (1995).
Ward et al., "Binding activities of a repertoire of single immunoglobulin variable domains secreted from *Escherichia coli*," 341(6242) Nature 544-6 (1989).
Waterhouse et al., "Combinatorial infection and in vivo recombination: a strategy for making large phage antibody repertoires," 21(9) Nucl Acids Res 2265-6 (1993).
Wells & Lowman, "Rapid evolution of peptide and protein binding properties in vitro," 2 Curr Opin Struct Biol 597-604 (1992).
Wigler et al., "Transfer of purified herpes virus thymidine kinase gene to cultured mouse cells" 11(1) Cell 223-32 (1977).
Wigler et al., "Transformation of mammalian cells with an amplifiable dominant-acting gene," 77(6) Proc Nat'l Acad Sci USA 3567-70 (1980).
Wilson et al., "The structure of an antigenic determinant in a protein," 37(3) Cell 767-78 (1984).
Winter & Milstein, "Man-made antibodies," 349(6307) Nature 293-9 (1991).
Wörn & Plückthun, "Stability engineering of antibody single-chain Fv fragments," 305(5) J Mol Biol 989-1010 (2001).
Wu & Wu, "Delivery systems for gene therapy," 3(1) Biotherapy 87-95 (1991).
Wu et al., "Multimerization of a chimeric anti-CD20 single-chain Fv-Fc fusion protein is mediated through variable domain exchange," 14(12) Protein Eng 1025-33 (2001).
Wu & Wu, "Receptor-mediated in-vitro gene transformation by a soluble DNA carrier system," 262(10) J Biol Chem 4429-32 (1987).
Wu "Simultaneous Humanization and Affinity Optimization of Monoclonal Antibodies" Methods in Molecular Biology, 207(1):197-212 (2003).
Xiang et al., "Modification in Framework Region I Results in a Decreased Affinity of Chimeric Anti-TAG72 Antibody" Molecular Immunology 28(1/2):141-48 (1998).
Yang et al., "CDR walking mutagenesis for the affinity maturation of a potent human anti-HIV-1 antibody into the picomolar range," 254(3) J Mol Biol 392-403 (1995).
Zuo et al., "An efficient route to the production of an IgG-like bispecific antibody." *Protein Engineering* 13(5):361-67 (2000).
Zurawski & De Vries, "Interleukin 13, an interleukin 4-like cytokine that acts on monocytes and B cells, but not on T cells," 15(1) Immunol Today 19-26 (1994).
Zurawski et al., "Receptors for interleukin-13 and interleukin-4 are complex and share a novel component that functions in signal transduction," 12(7) EMBO J 2663-70 (1993).
Zurawski et al., "Continuously Proliferating Human Cell Lines Synthesizing Antibody of Predetermined Specificity," in Monoclonal Antibodies Chapter2:19-33 (Kennett et al., eds. 1980).
Final Office Action issued in U.S. Appl. No. 13/758,858 dated Sep. 18, 2015, pp. 1-7.
Final Office Action issued in U.S. Appl. No. 13/794,295 dated May 29, 2015, pp. 1-14.
Final Office Action issued in U.S. Appl. No. 13/794,295 dated Apr. 8, 2016, pp. 1-17. (Double patenting rejection issued).
Final Office Action issued in U.S. Appl. No. 13/794,310 dated May 29, 2015, pp. 1-20.
Final Office Action issued in U.S. Appl. No. 13/794,310 dated Apr. 22, 2016, pp. 1-30.
Final Office Action issued in U.S. Appl. No. 13/794,320 dated May 2, 2014, pp. 1-11.
Final Office Action issued in U.S. Appl. No. 13/794,320 dated Oct. 31, 2014, pp. 1-15.
Final Office Action issued in U.S. Appl. No. 13/794,341 dated Jul. 30, 2015, pp. 1-21.
Final Office Action issued in U.S. Appl. No. 13/794,341 dated May 5, 2016, pp. 1-28.
Final Office Action issued in U.S. Appl. No. 13/794,354 dated Sep. 4, 2014, pp. 1-11.
Final Office Action issued in U.S. Appl. No. 13/794,370 dated Jun. 10, 2015, pp. 1-16.
Final Office Action issued in U.S. Appl. No. 13/794,384 dated Jun. 12, 2015, pp. 1-18.
Final Office Action issued in U.S. Appl. No. 13/794,384 dated Nov. 24, 2015, pp. 1-23.
Final Office Action issued in U.S. Appl. No. 13/794,394 dated Jun. 30, 2015, pp. 1-22.
Final Office Action issued in U.S. Appl. No. 13/794,394 dated Nov. 17, 2015, pp. 1-22.
Final Office Action issued in U.S. Appl. No. 13/831,856 dated Dec. 28, 2015, pp. 1-8.
Final Office Action issued in U.S. Appl. No. 13/831,862 dated Nov. 13, 2015, pp. 1-18.
Final Office Action issued in U.S. Appl. No. 13/831,884 dated Dec. 22, 2015, pp. 1-9.
International Preliminary Report on Patentability in International Application No. PCT/US2008/079787, report dated Apr. 20, 2010.
International Search Report in International Application No. PCT/US2008/079787, dated Apr. 8, 2009.
Non-Final Office Action issued in U.S. Appl. No. 12/682,864 dated Mar. 9, 2012, pp. 1-8.
Non Final Office Action issued in U.S. Appl. No. 13/794,295 dated Dec. 19, 2016, pp. 1-8.
Non-Final Office Action issued in U.S. Appl. No. 13/758,858 dated Sep. 18, 2014, pp. 1-13.
Non-Final Office Action issued in U.S. Appl. No. 13/794,295 dated Nov. 19, 2014, pp. 1-20.
Non-Final Office Action issued in U.S. Appl. No. 13/794,310 dated Jan. 14, 2015, pp. 1-29.

(56) References Cited

OTHER PUBLICATIONS

Non-Final Office Action issued in U.S. Appl. No. 13/794,320 dated Nov. 4, 2013, pp. 1-12.
Non-Final Office Action issued in U.S. Appl. No. 13/794,341 dated Jan. 15, 2015, pp. 1-29.
Non-Final Office Action issued in U.S. Appl. No. 13/794,354 dated Mar. 24, 2014, pp. 1-11.
Non-Final Office Action issued in U.S. Appl. No. 13/794,370 dated Nov. 26, 2014, pp. 1-21.
Non-Final Office Action issued in U.S. Appl. No. 13/794,370 dated Dec. 22, 2015, pp. 1-17.
Non-Final Office Action issued in U.S. Appl. No. 13/794,384 dated Nov. 25, 2014, pp. 1-27.
Non-Final Office Action issued in U.S. Appl. No. 13/794,394 dated Dec. 9, 2014, pp. 1-26.
Non-Final Office Action issued in U.S. Appl. No. 13/831,856 dated Jun. 29, 2015, pp. 1-14.
Non-Final Office Action issued in U.S. Appl. No. 13/831,862 dated Jul. 12, 2016, pp. 1-15.
Non-Final Office Action issued in U.S. Appl. No. 13/831,862 dated May 13, 2015, pp. 1-22.
Non-Final Office Action issued in U.S. Appl. No. 13/831,866 dated Apr. 23, 2014, pp. 1-12.
Non-Final Office Action issued in U.S. Appl. No. 13/831,866 dated Oct. 30, 2014, pp. 1-10.
Non-Final Office Action issued in U.S. Appl. No. 13/831,884 dated Jul. 22, 2015, pp. 1-15.

Anti-IL13 hB-B13 VL3 (SEQ ID NO: 1):
DIVLTQSPAS LAVSLGQRAT ISCRASESVD SYGQSYMHWY QQKAGQPPKL
LIYLASNLES GVPARFSGSG SRTDFTLTID PVQAEDAATY YCQQNAEDSR
TFGGGTKLEI K Anti-IL13 hB-B13 VH2 (SEQ ID NO: 2):
EVQLKESGPG LVAPGGSLSI TCTVSGFSLT DSSINWVRQP PGKGLEWLGM
IWGDGRIDYA DALKSRLSIS KDSSKSQVFL EMTSLRTDDT ATYYCARDGY
FPYAMDFWGQ GTSVTVSS Anti-IL4 h8D4-8 VL1 (SEQ ID NO: 3):
DIQMTQSPAS LSVSVGDTIT LTCHASQNID VWLSWFQQKP GNIPKLLIYK
ASNLHTGVPS RFSGSGSGTG FTLTISSLQP EDIATYYCQQ AHSYPFTFGG
GTKLEIKR Anti-IL4 h8D4-8 VH1 (SEQ ID NO: 4):
QVQLQQSGPE LVKPGASVKI SCKASGYSFT SYWIHWIKQR PGQGLEWIGM
IDPSDGETRL NQRFQGRATL TVDESTSTAY MQLRSPTSED SAVYYCTRLK
EYGNYDSFYF DVWGAGTLVT VSSA Anti-IL4 h8D4-8 VH2 (SEQ ID NO: 5):
QVQLQQSGPE LVKPGASVKI SCKASGYSFT SYWIHWIKQR PGQGLEWIGM
IDASDGETRL NQRFQGRATL TVDESTSTAY MQLRSPTSED SAVYYCTRLK
EYGNYDSFYF DVWGAGTLVT VSSA

FIG. 2

ANTIBODIES THAT BIND IL-4 AND/OR IL-13 AND THEIR USES

CROSS REFERENCE TO RELATED APPLICATIONS

This application is a continuation of U.S. patent application Ser. No. 13/831,862, filed Mar. 15, 2013, which is a continuation of U.S. patent application Ser. No. 13/758,858, filed Feb. 4, 2013 (now abandoned), which is a continuation of U.S. patent application Ser. No. 12/682,864, filed Apr. 13, 2010, which issued as U.S. Pat. No. 8,388,965, and which is a national stage application under 35 U.S.C. § 371 of International Application No. PCT/US2008/079787, filed Oct. 14, 2008, which claims the benefit of U.S. Provisional Application No. 61/037,128, filed Mar. 17, 2008, and European Patent Application No. 07 291 259.5, filed Oct. 15, 2007, the disclosures of each of which are explicitly incorporated by reference herein.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952526005SeqList.txt, date recorded: Jul. 10, 2017, size: 10 KB).

FIELD OF THE INVENTION

The present invention relates to novel anti-IL-4 antibodies, anti-IL-13 antibodies and bispecific anti-IL-4/anti-IL-13 antibodies and their use in the amelioration, treatment or prevention of diseases or disorders in mammals, including humans, resulting from improper IL-4 and/or IL-13 activity or metabolism. An antibody of interest may block engagement and/or signaling of a ligand, such as IL-4 or IL-13, with a receptor or receptor complex, such as IL-4Rα, IL-13Rα1 and IL-13Rα2. Prophylactic, immunotherapeutic and diagnostic compositions comprising the antibodies of interest and their use in methods for preventing or treating diseases in mammals, including humans, caused by inappropriate metabolism and/or activity of lymphoid and non-lymphoid cells, including monocytes, fibroblasts and endothelial cells, are disclosed. Such diseases include autoimmune deficiencies and diseases caused by or characterized by inflammation, such as allergic asthma and dermatitis.

BACKGROUND OF THE INVENTION

Interleukin-4 (IL-4) is a pleiotropic cytokine that has a broad spectrum of biological effects on lymphoid B and T cells, and many non-lymphoid cells including monocytes, endothelial cells and fibroblasts. For example, IL-4 stimulates the proliferation of several IL-2- and IL-3-dependent cell lines, induces the expression of class II major histocompatability complex molecules on resting B cells, and enhances the secretion of IgG4 and IgE by human B cells. IL-4 is associated with a Th2-type immune response, and is produced by and promotes differentiation of Th2 cells. IL-4 has been implicated in a number of disorders, such as allergy and asthma.

IL-13 is a recently identified (Minty, A. et al., Nature, 1993, 362, 248-250, and McKenzie, A. N. et al., Proc. Natl. Acad. Sci. U.S.A, 1993, 90, 3735-3739) cytokine of 112 amino acids secreted by the activated T lymphocytes, the B lymphocytes and the mastocytes after activation.

By virtue of its numerous biological properties shared with IL-4, IL-13 has been described as an IL-4-like cytokine. Its activities are indeed similar to those of IL-4 on the B cells (Defrance, T. et al., J. Exp. Med., 1994, 179, 135-143, Punnonen, J. et al., Proc. Natl. Acad. Sci. (USA), 1993, 90, 3730-3734, Fior, R. et al., Eur. Cytokine Network, 1994, 5, 593-600), the monocytes (Muzio, M. R. F. et al., Blood, 1994, 83, 1738-1743, De Waal Malefyt, R. et al., J. Immunol, 1993, 151, 6370-6381, Doyle, A. et al., Eur. J. Immunol. 1994, 24, 1441-1445, Montaner, L. J. et al., J. Exp. Med., 1993, 178, 743-747, Sozzani, P. et al., J. Biol. Chem., 1995, 270, 5084-5088) and other non-haematopoietic cells (Herbert, J. M. et al., Febs Lett., 1993, 328, 268-270, and Derocq, J. M. et al., Febs Lett. 1994, 343, 32-36). On the other hand, contrary to IL-4, it does not exert a specific effect on resting or activated T cells (Zurawuki, G. et al., Immunol. Today, 1994, 15, 19-26).

Various biological activities of IL-13 on the monocytes/macrophages, the B lymphocytes and certain haematopoietic precursors have been described in detail by A. J. Minty as well as in review articles on IL-13. Several data indicate, in addition, that this cytokine has a pleiotropic effect on other cell types. These non-haematopoietic cells which are directly affected by IL-13 are endothelial and microglial cells, keratinocytes and kidney and colon carcinomas.

One of the stages in the analysis of the signal transmitted by a biological molecule within a cell consists in identifying its membrane receptor. The research studies carried out to this end on the IL-13 receptor have shown that IL-13 and IL-4 have a common receptor, or at the very least some of the components of a common receptor complex, as well as common signal transduction elements (Zurawski S. M. et al., Embo Journal, 1993, 12, 2663-2670, Aversa, G. et al., J. Exp. Med., 1993, 178, 2213-2218, Vita, N. et al., Biol. Chem., 1995, 270, 3512-3517, Lefort, S. et al., Febs Lett., 1995, 366, 122-126). This receptor is present at the surface of various cell types, in a variable number according to the cell type considered. The comparative distribution of the IL-13 and IL-4 receptors has been indicated by A. J. Minty (Interleukin-13 for Cytokines in Health and Disease. Eds D. G. Remick and J. S. Frie, Marcel Decker, N.Y. 1996).

The cell surface receptors and receptor complexes bind IL-4 and/or IL-13 with different affinities. The principle components of receptors and receptor complexes that bind IL-4 and/or IL-13 are IL-4Rα, IL-13Rα1 and IL-13Rα2. These chains are expressed on the surface of cells as monomers or heterodimers of IL-4Rα/IL-13Rα1 (Type II IL-4R) or IL-4Rα/γc (Type I IL-4R). IL-4Rα monomer and IL-4Rα/γc heterodimer bind IL-4, but not IL-13. IL-13Rα1 and IL-13Rα2 monomers bind IL-13, but do not bind IL-4. IL-4Rα/IL-13Rα1 heterodimer binds both IL-4 and IL-13 (Murata et al., Int. J. Hematol., 1999, 69, 13-20).

Th2-type immune responses promote antibody production and humoral immunity, and are elaborated to fight off extracellular pathogens. Th2 cells are mediators of Ig production (humoral immunity) and produce IL-4, IL-5, IL-6, IL-9, IL-10 and IL-13 (Tanaka, et, al., Cytokine Regulation of Humoral Immunity, 251-272, Snapper, ed., John Wiley and Sons, New York (1996)). Th2-type immune responses are characterized by the generation of certain cytokines (e.g., IL-4, IL-13) and specific types of antibodies (IgE, IgG4) and are typical of allergic reactions, which may result in watery eyes and asthmatic symptoms, such as airway inflammation and contraction of airway muscle cells in the lungs.

Both IL-4 and IL-13 are therapeutically important cytokines based on their biological functions and play critical roles in many diseases, including asthma (Curr Opin Allergy Clin Immunol 2005, Vo. 5, 161-166). IL-4 has been shown to be able to inhibit autoimmune disease and IL-4 and IL-13 have both shown the potential to enhance anti-tumor immune responses. Since both cytokines are involved in the pathogenesis of allergic diseases, inhibitors of these cytokines could provide therapeutic benefits.

Accordingly, a need exists for improved agents that inhibit IL-4, inhibit IL-13, and single agents that inhibit both IL-4 and IL-13.

SUMMARY OF THE INVENTION

The present invention provides novel humanized monoclonal and bispecific antibodies, and fragments and derivatives thereof, which specifically bind to IL-4 and/or IL-13. Some of the anti-IL-4 and/or IL-13 mono- or bispecific antibodies, and fragments thereof, can be altered to prevent intrachain disulfide bond formation resulting in a molecule that is stable through manufacturing and use in vivo. The antibodies of the present invention neutralize IL-4 and/or IL-13 activity in the biological assays described herein.

The invention includes the amino acid sequences of the variable heavy and light chain of the antibodies and their corresponding nucleic acid sequences.

Another embodiment of the present invention includes the cell lines and vectors harboring the antibody sequences of the present invention.

Another embodiment of the present invention is the use of the antibodies for the preparation of a pharmaceutical composition for the treatment of diseases and disorders associated with IL-4 and/or IL-13 function and metabolism. In particular, the present invention relates to the treatment of cancer, autoimmune deficiencies and diseases caused by or characterized by inflammation, such as allergic asthma and dermatitis.

Additional features and advantages are described herein, and will be apparent from, the following Detailed Description and the figures.

BRIEF DESCRIPTION OF THE DRAWINGS

FIG. 2 illustrates the amino acid sequences of humanized variable domains of B-B13 anti-IL-13 antibody (SEQ ID NOS: 1 and 2) and humanized variable domains of 8D4-8 anti-IL-4 antibody (SEQ ID NOS: 3, 4 and 5). Underline indicates amino acid changes made. Bold indicates the CDR.

DETAILED DESCRIPTION OF THE INVENTION

Figure 1:
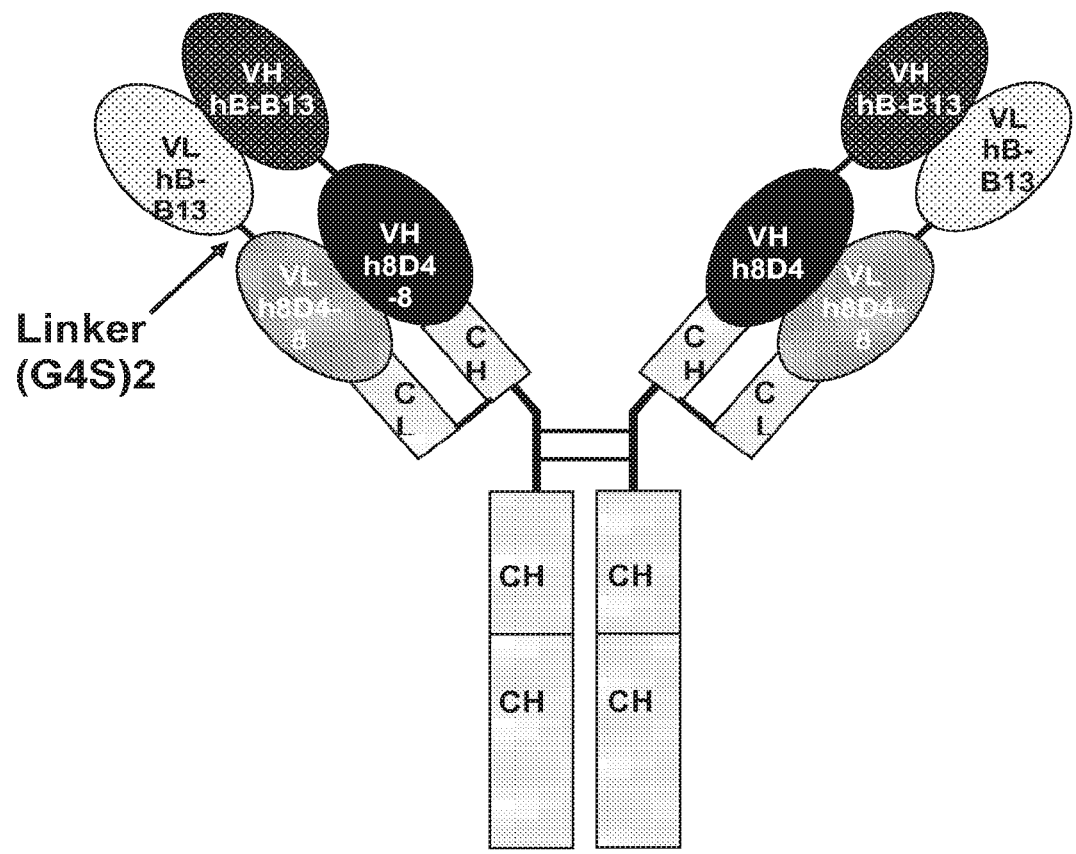
FIG. 1 is a schematic drawing of a bispecific anti-IL-4/IL-13 antibody molecule containing four polypeptide chains. Two lighter chains consist of N-VL$_{hB-B13}$-linker-VL$_{h8D4-8}$-CL-C(CL, light chain constant region), two heavier chains consist of N-VH$_{hB-B13}$-linker-VH$_{h8D4-8}$-CH1-CH2-CH3-C. The linker sequence (G4S)$_2$ is GGGGSGGGGS (SEQ ID NO: 6).

This invention is not limited to the particular methodology, protocols, cell lines, vectors, or reagents described herein because they may vary without departing from the spirit and scope of the invention. Further, the terminology used herein is for the purpose of exemplifying particular embodiments only and is not intended to limit the scope of the present invention. Unless defined otherwise, all technical and scientific terms and any acronyms used herein have the same meanings as commonly understood by one of ordinary skill in the art in the field of the invention. Any method and material similar or equivalent to those described herein can be used in the practice of the present invention and only exemplary methods, devices, and materials are described herein.

All patents and publications mentioned herein are incorporated herein in entirety by reference for the purpose of describing and disclosing the proteins, enzymes, vectors, host cells and methodologies reported therein that might be used with and in the present invention. However, nothing herein is to be construed as an admission that the invention is not entitled to antedate such disclosure by virtue of prior invention.

Prior to teaching the making and using of the IL-4 and/or IL-13 related methods and products of interest, the following non-limiting definitions of some terms and phrases are provided to guide the artisan.

"Interleukin-4" (IL-4) relates to the naturally occurring, or endogenous mammalian IL-4 proteins and to proteins having an amino acid sequence which is the same as that of a naturally occurring or endogenous corresponding mammalian IL-4 protein {e.g., recombinant proteins, synthetic proteins (i.e., produced using the methods of synthetic organic chemistry)). Accordingly, as defined herein, the term includes mature IL-4 protein, polymorphic or allelic variants, and other isoforms of an IL-4 and modified or unmodified forms of the foregoing (e.g., lipidated, glycosylated). Naturally occurring or endogenous IL-4 includes wild type proteins such as mature IL-4, polymorphic or allelic variants and other isoforms and mutant forms which occur naturally in mammals (e.g., humans, non-human primates). Such proteins can be recovered or isolated from a source which naturally produces IL-4, for example. These proteins and proteins having the same amino acid sequence as a naturally occurring or endogenous corresponding IL-4, are referred to by the name of the corresponding mammal. For example, where the corresponding mammal is a human, the protein is designated as a human IL-4. Several mutant IL-4 proteins are known in the art, such as those disclosed in WO 03/038041.

"Interleukin-13" (IL-13) refers to naturally occurring or endogenous mammalian IL-13 proteins and to proteins having an amino acid sequence which is the same as that of a naturally occurring or endogenous corresponding mammalian IL-13 protein (e.g., recombinant proteins, synthetic proteins (i.e., produced using the methods of synthetic organic chemistry)). Accordingly, as defined herein, the term includes mature IL-13 protein, polymorphic or allelic variants, and other isoforms of IL-13 (e.g., produced by alternative splicing or other cellular processes), and modified or unmodified forms of the foregoing (e.g., Hpidated, glycosylated). Naturally occurring or endogenous IL-13 include wild type proteins such as mature IL-13, polymorphic or allelic variants and other isoforms and mutant forms which occur naturally in mammals (e.g., humans, non-human primates). For example, as used herein IL-13 encompasses the human IL-13 variant in which Arg at position 110 of mature human IL-13 is replaced with Gin (position 110 of mature IL-13 corresponds to position 130 of the precursor protein) which is associated with asthma (atopic and nonatopic asthma) and other variants of IL-13. (Heinzmann et al, Hum Mol Genet. 9:549-559 (2000).) Such proteins can be recovered or isolated from a source which naturally produces IL-13, for example. These proteins and proteins having the same amino acid sequence as a naturally occurring or endogenous corresponding IL-13 are referred to by the name of the corresponding mammal. For example, where the corresponding mammal is a human, the protein is designated as a human IL-13. Several mutant IL-13 proteins are known in the art, such as those disclosed in WO 03/035847.

The phrase "substantially identical" with respect to an antibody chain polypeptide sequence may be construed as an antibody chain exhibiting at least 70%, 80%, 90%, 95% or more sequence identity to the reference polypeptide sequence. The term with respect to a nucleic acid sequence may be construed as a sequence of nucleotides exhibiting at least about 85%, 90%, 95%, or 97% or more sequence identity to the reference nucleic acid sequence.

The terms, "identity" or "homology" may mean the percentage of nucleotide bases or amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

The phrases and terms "functional fragment, variant, derivative or analog" and the like, as well as forms thereof, of an antibody or antigen is a compound or molecule having qualitative biological activity in common with a full-length antibody or antigen of interest. For example, a functional fragment or analog of an anti-IL-4 antibody is one which can bind to an IL-4 molecule or one which can prevent or substantially reduce the ability of a ligand, or an agonistic or antagonistic antibody, to bind to IL-4.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "antibody" is used in the broadest sense, and specifically covers monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity. The antibodies of the invention can be of any class (e.g., IgG, IgE, IgM, IgD, IgA and so on), or subclass (e.g., $IgG_1$, $IgG_2$, $IgG_{2a}$, $IgG_3$, $IgG_4$, $IgA_1$, $IgA_2$ and so on) ("type" and "class", and "subtype" and ""subclass", are used interchangeably herein). Native or wildtype, that is, obtained from a non-artificially manipulated member of a population, antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at the other end. By "non-artificially manipulated" is meant not treated to contain or express a foreign antigen binding molecule. Wildtype can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-IL-4 antibody" means an antibody or polypeptide derived therefrom (a derivative) which binds specifically to IL-4 as defined herein, including, but not limited to, molecules which inhibit or substantially reduce the binding of IL-4 to its receptor or inhibit IL-4 activity.

As used herein, "anti-IL-13 antibody" means an antibody or polypeptide derived therefrom (a derivative) which binds specifically to IL-13 as defined herein, including, but not limited to, molecules which inhibit or substantially reduce the binding of IL-13 to its receptor or inhibit IL-13 activity.

The term "variable" in the context of a variable domain of antibodies refers to certain portions of the pertinent molecule which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat et al., unless otherwise indicated. One CDR can carry the ability to bind specifically to the cognate epitope.

The term "hinge" or "hinge region" as used in the present invention refers to the flexible polypeptide comprising the amino acids between the first and second constant domains of an antibody.

The term "antibody fragment" refers to a portion of an intact or a full-length chain or an antibody, generally the target binding or variable region. Examples of antibody fragments include, but are not limited to, $F_{ab}$, $F_{ab'}$, $F_{(ab')2}$ and $F_v$ fragments. A "functional fragment" or "analog of an anti-IL-4 and/or IL-13 antibody" is one which can prevent or substantially reduce the ability of the receptor to bind to a ligand or to initiate signaling. As used herein, functional fragment generally is synonymous with, "antibody fragment" and with respect to antibodies, can refer to fragments, such as $F_v$, $F_{ab}$, $F_{(ab')2}$ and so on which can prevent or substantially reduce the ability of the receptor to bind to a ligand or to initiate signaling. An "$F_v$" fragment consists of a dimer of one heavy and one light chain variable domain in a non-covalent association (Vu-$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an $F_v$ comprising only three CDRs specific for a target) can have the ability to recognize and to bind target.

"Single-chain $F_v$," "sFv" or "scAb" antibody fragments comprise the $V_H$ and $V_L$ domains of an antibody, wherein these domains are present in a single polypeptide chain. Generally, the $F_v$ polypeptide further comprises a polypeptide linker, often a flexible molecule, between the $V_H$ and $V_L$ domains, which enables the sFv to form the desired structure for target binding.

The term "diabodies" refers to antibody fragments with two antigen-binding sites, which fragments can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with the binding domains of another chain to create two antigen-binding sites.

The $F_{ab}$ fragment contains the variable and constant domains of the light chain and the variable and first constant domain ($C_{H1}$) of the heavy chain. $F_{ab}$ fragments differ from $F_{ab}$ fragments by the addition of a few residues at the carboxyl terminus of the Cm domain to include one or more cysteines from the antibody hinge region. $F_{ab}$ fragments can be produced by cleavage of the disulfide bond at the hinge cysteines of the $F_{(ab')2}$ pepsin digestion product. Additional enzymatic and chemical treatments of antibodies can yield other functional fragments of interest.

The term "linear Fab" refers to a tetravalent antibody as described by Miller et al. (2003), J Immunol. 170: 4854-4861. The "linear Fab" is composed of a tandem of the same CH1-VH domain, paired with the identical light chain at each CH1-VH position. These molecules have been developed in order to increase the valency of an antibody to enhance its functional affinity through the avidity effect, but they are monospecific.

The term "bispecific antibodies (BsAbs)" refers to molecules which combine the antigen-binding sites of two antibodies within a single molecule. Thus, a bispecific antibody is able to bind two different antigens simultaneously. Besides applications for diagnostic purposes, BsAbs pave the way for new therapeutic applications by redirecting potent effector systems to diseased areas or by increasing neutralizing or stimulating activities of antibodies.

Initial attempts to couple the binding specificities of two whole antibodies against different target antigens for therapeutic purposes utilized chemically fused heteroconjugate molecules (Staerz et al. (1985), Nature 314: 628-631).

Bispecific antibodies have been produced from hybrid hybridomas by heterohybridoma techniques and have demonstrated in vitro properties similar to those observed for heteroconjugates (Milstein & Cuello (1983) Nature 305: 537-540).

Despite the promising results obtained using heteroconjugates or bispecific antibodies produced from cell fusions as cited above, several factors made them impractical for large scale therapeutic applications. Such factors include: rapid clearance of large heteroconjugates in vivo, the labor intensive techniques required for generating either type of molecule, the need for extensive purification of heteroconjugates away from homoconjugates or mono-specific antibodies and generally low yields.

Genetic engineering has been used with increasing frequency to design, modify, and produce antibodies or antibody derivatives with a desired set of binding properties and effector functions.

A variety of recombinant methods have been developed for efficient production of BsAbs, both as antibody fragments (Carter et al. (1995), J. Hematotherapy 4: 463-470; Pluckthun et al. (1997) Immunotechology 3: 83-105; Todorovska et al. (2001) J. Immunol. Methods 248: 47-66) and full length IgG formats (Carter (2001) J. Immunol. Methods 248: 7-15).

Combining two different scFvs results in BsAb formats with minimal molecular mass, termed sc-BsAbs or Ta-scFvs (Mack et al. (1995), Proc. Acad. Sci. USA. 92: 7021-7025, Mallender et al. (1994) J. Biol. Chem. 269: 199-206). BsAbs have been constructed by genetically fusing two scFvs via dimerization functionality such as a leucine zipper (Kostelny et al. (1992) J. Immunol. 148: 1547-53; de Kruif et al. (1996) J. Biol. Chem. 271: 7630-4).

As mentioned above, diabodies are small bivalent and bispecific antibody fragments. The fragments comprise a VH connected to a VL on the same polypeptide chain, by using a linker that is too short (less than 12 amino acids) to allow pairing between the two domains on the same chain. The domains are forced to pair intermolecularly with the complementary domains of another chain and create two antigen-binding sites. These dimeric antibody fragments, or "diabodies," are bivalent and bispecific. (Holliger et al. (1993), Proc. Natl. Acad. Sci. USA. 90: 6444-6448). Diabodies are similar in size to a Fab fragment. Polypeptide chains of VH and VL domains joined with linker between 3 and 12 amino acids form predominantly dimers (diabodies), whereas with linker between 0 and 2 amino acid residues, trimers (triabodies) and tetramers (tetrabodies) find favor. In addition to the linker length, the exact pattern of oligomerization seems to depend on the composition as well as the orientation of the V-domains (Hudson et al. (1999), J Immunol Methods 231: 177-189). The predictability of the final structure of diabody molecules is very poor.

Although sc-BsAbs and diabodies based constructs display interesting clinical potential, it was shown that such non-covalently associated molecules are not sufficient stable under physiological conditions. The overall stability of a scFv fragment depends on the intrinsic stability of the VL and VH domains as well as on the stability of the domain interface. Insufficient stability of the VH-VL interface of scFv fragments has often been suggested as a main cause of irreversible scFv inactivation, since transient opening of the interface, which would be allowed by the peptide linker, exposes hydrophobic patches that favor aggregation and therefore instability and poor production yield (Wörn and Plückthun (2001), J. Mol. Biol. 305: 989-1010).

An alternative method of manufacturing bispecific bivalent antigen-binding proteins from VH and VL domains is disclosed in U.S. Pat. No. 5,989,830. Such double head antibody fragments are obtained by expressing a dicistronic vector which encodes two polypeptide chains, whereby one polypeptide chain has two times a VH in series by a peptide linker (VH1-linker-VH2) and the other polypeptide chain consisting of complementary VL domains connected in series by a peptide linker (VL1-linker-VL2). It was described in U.S. Pat. No. 5,989,830 that each linker should comprise at least 10 amino acid residues.

Polyvalent protein complexes (PPC) with an increased valency are described in US 2005/0003403 A1. PPCs comprise two polypeptide chains generally arranged laterally to one another. Each polypeptide chain typically comprises 3 or 4 "v-regions", which comprise amino acid sequences capable of forming an antigen binding site when matched with a corresponding v-region on the opposite polypeptide chain. Up to about 6 "v-regions" can be used on each polypeptide chain. The v-regions of each polypeptide chain are connected linearly to one another and may be connected by interspersed linking regions. When arranged in the form of the PPC, the v-regions on each polypeptide chain form individual antigen binding sites. The complex may contain one or several binding specificities.

However, the use of such molecules showed aggregation, unstability and poor expression yield (Wu et al. (2001) Prot. Eng. 14: 1025-1033). These are typical stability problems that may occur expressing single chain based antibodies. (Wörn and Plûckthun (2001), J. Mol. Biol. 305: 989-1010).

Thus, it is the object of the present invention to provide a bispecific polyvalent antibody by means of which the formation of aggregates can be avoided. Furthermore, it shall have a stability which makes it usable for therapeutic uses.

The term "monoclonal antibody" as used herein refers to an antibody obtained from a population of substantially homogeneous antibodies, i.e., the individual antibodies comprising the population are identical except for possible naturally occurring mutations that may be present in minor amounts.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as they exhibit the desired biological activity of binding to IL-4 and/or IL-13 or impacting IL-4 and/or IL-13 activity or metabolism (U.S. Pat. No. 4,816,567; and Morrison et al., Proc Natl Acad Sci USA 81:6851 (1984)). Thus, CDRs from one class of antibody can be grafted into the FR of an antibody of different class or subclass.

Monoclonal antibodies are highly specific, being directed against a single target site, epitope or determinant. Furthermore, in contrast to conventional (polyclonal) antibody preparations which typically include different antibodies directed against different determinants (epitopes) of an antigen, each monoclonal antibody is directed against a single determinant on the target. In addition to their specificity, monoclonal antibodies are advantageous being synthesized by a host cell, uncontaminated by other immunoglobulins, and provides for cloning the relevant gene and mRNA encoding the antibody of chains thereof. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using well known techniques or can be purified from a polyclonal prep. The parent monoclonal antibodies to be used in accordance with the present invention may be made by the hybridoma method described by Kohler et al., Nature 256:495 (1975), or may be made by recombinant methods well known in the art.

The term "polyvalent antibody" as used in the present invention refers to an antibody comprising two or more antigen binding sites, thus being able to bind two or more antigens, which may have the same or a different structure, simultaneously. The term "bivalent" means that the antibody comprises two antigen binding sites. The term "tetravalent" means that the antibody comprises four antigen binding sites.

The term "antigen binding site" as used in the present invention refers to the part of the antibody which comprises the area which specifically binds to and is complementary to part or all of an antigen. Where an antigen is large, an antibody may only bind to a particular part of the antigen, which part is termed on epitope. An antigen binding domain may be provided by one or more antibody variable domains. Preferably, an antigen binding domain is made of the association of an antibody light chain variable domain (VL) and an antibody heavy chain variable domain (VH).

The term "antigen" as used in the present invention refers to a molecule or a portion of a molecule capable of being bound by the antibodies of the present invention. An antigen can have one or more than one epitope. Examples of antigens recognized by the antibodies of the present invention include, but are not limited to, serum proteins, e.g. cytokines such as IL-4, IL5, IL9 and IL-13, bioactive peptides, cell surface molecules, e.g. receptors, transporters, ion-channels, viral and bacterial proteins.

The term "monospecific" as used in the present invention means that the polyvalent antibody of the present invention recognizes only one antigen, all the antigen binding sites being identical.

The term "bispecific" as used in the present invention means that the polyvalent antibody of the present invention recognizes two different epitopes on the same or on two different antigens.

The term "multispecific" as used in the present invention means that the polyvalent antibody of the present invention recognizes multiple different epitopes on the same or on multiple different antigens.

The term "linker" as used in the present invention refers to a peptide adapted to connect the variable domains of the antibody constructs of the present invention. The peptide linker may contain any amino acids, the amino acids glycine (G) and serine (S) being preferred. The linkers may be equal or differ from each other between and within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19 or 20 amino acids. A preferred peptide linker unit for the heavy chain domains as for the light chain domains is GGGGS. The numbers of linker units of the heavy chain and of the light chain may be equal (symmetrical order) or differ from each other (asymmetrical order).

A peptide linker is preferably long enough to provide an adequate degree of flexibility to prevent the antibody moieties from interfering with each others activity, for example by steric hindrance, to allow for proper protein folding and, if necessary, to allow the antibody molecules to interact with two or more, possibly widely spaced, receptors on the same cell; yet it is preferably short enough to allow the antibody moieties to remain stable in the cell.

Therefore, the length, composition and/or conformation of the peptide linkers can readily be selected by one skilled in the art in order to optimize the desired properties of the polyvalent antibody.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies) which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_c$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to IL-4 and/or IL-13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., Prot Eng 7(6)805-814, 1994; Mol Imm 44:1986-1988, 2007; Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333 and U.S. Pat. No. 5,869,619.

A humanization method of interest is based on the impact of the molecular flexibility of the antibody during and at immune recognition. Protein flexibility is related to the molecular motion of the protein molecule. Protein flexibility is the ability of a whole protein, a part of a protein or a single amino acid residue to adopt an ensemble of conformations which differ significantly from each other. Information about protein flexibility can be obtained by performing protein X-ray crystallography experiments (see, for example, Kundu et al. 2002, Biophys J 83:723-732.), nuclear magnetic resonance experiments (see, for example, Freedberg et al., J Am Chem Soc 1998, 120(31):7916-7923) or by running molecular dynamics (MD) simulations. An MD simulation of a protein is done on a computer and allows one to determine the motion of all protein atoms over a period of time by calculating the physical interactions of the atoms with each other. The output of a MD simulation is the trajectory of the studied protein over the period of time of the simulation. The trajectory is an ensemble of protein conformations, also called snapshots, which are periodically sampled over the period of the simulation, e.g. every 1 picosecond (ps). It is by analyzing the ensemble of snapshots that one can quantify the flexibility of the protein amino acid residues. Thus, a flexible residue is one which adopts an ensemble of different conformations in the context of the polypeptide within which that residue resides. MD methods are known in the art, see, e.g., Brooks et al. "Proteins: A Theoretical Perspective of Dynamics, Structure and Thermodynamics" (Wiley, New York, 1988). Several software enable MD simulations, such as Amber (see Case et al. (2005) J Comp Chem 26:1668-1688), Charmm (see Brooks et al. (1983) J Comp Chem 4:187-217; and MacKerell et al. (1998) in "The Encyclopedia of Computational Chemistry" vol. 1:271-177, Schleyer et al., eds. Chichester: John Wiley & Sons) or Impact (see Rizzo et al. J Am Chem Soc; 2000; 122(51):12898-12900.)

Most protein complexes share a relatively large and planar buried surface and it has been shown that flexibility of binding partners provides the origin for their plasticity, enabling them to conformationally adapt to each other (Structure (2000) 8, R137-R142). As such, examples of "induced fit" have been shown to play a dominant role in protein-protein interfaces. In addition, there is a steadily increasing body of data showing that proteins actually bind ligands of diverse shapes sizes and composition (Protein Science (2002) 11:184-187) and that the conformational diversity appears to be an essential component of the ability to recognize different partners (Science (2003) 299, 1362-1367). Flexible residues are involved in the binding of protein-protein partners (Structure (2006) 14, 683-693).

The flexible residues can adopt a variety of conformations that provide an ensemble of interaction areas that are likely to be recognized by memory B cells and to trigger an immunogenic response. Thus, antibody can be humanized by modifying a number of residues from the framework so that the ensemble of conformations and of recognition areas displayed by the modified antibody resemble as much as possible those adopted by a human antibody.

That can be achieved by modifying a limited number of residues by: (1) building a homology model of the parent mAb and running an MD simulation; (2) analyzing the flexible residues and identification of the most flexible residues of a non-human antibody molecule, as well as identifying residues or motifs likely to be a source of heterogeneity or of degradation reaction; (3) identifying a human antibody which displays the most similar ensemble of recognition areas as the parent antibody; (4) determining the flexible residues to be mutated, residues or motifs likely to be a source of heterogeneity and degradation are also mutated; and (5) checking for the presence of known T cell or B cell epitopes. The flexible residues can be found using an MD calculation as taught herein using an implicit solvent model, which accounts for the interaction of the water solvent with the protein atoms over the period of time of the simulation. Once the set of flexible residues has been identified within the variable light and heavy chains, a set of human heavy and light chain variable region frameworks that closely resemble that of the antibody of interest are identified. That can be done, for example, using a blast search on the set of flexible residues against a database of antibody human germline sequence. It can also be done by comparing the dynamics of the parent mAb with the dynamics of a library of germline canonical structures. The CDR residues and neighboring residues are excluded from the search to ensure high affinity for the antigen is preserved.

Flexible residues then are replaced. When several human residues show similar homologies, the selection is driven also by the nature of the residues that are likely to affect the solution behavior of the humanized antibody. For instance, polar residues will be preferred in exposed flexible loops over hydrophobic residues. Residues which are a potential source of instability and heterogeneity are also mutated even if there are found in the CDRs. That will include exposed methionines as sulfoxide formation can result from oxygen radicals, proteolytic cleavage of acid labile bonds such as those of the Asp-Pro dipeptide (Drug Dev Res (2004) 61:137-154), deamidation sites found with an exposed asparagine residue followed by a small amino acid, such as Gly, Ser, Ala, His, Asn or Cys (J Chromatog (2006) 837: 35-43) and N-glycosylation sites, such as the Asn-X-Ser/Thr site. Typically, exposed methionines will be substituted by a Leu, exposed asparagines will be replaced by a glutamine or by an aspartate, or the subsequent residue will be changed. For the glycosylation site (Asn-X-Ser/Thr), either the Asn or the Ser/Thr residue will be changed.

The resulting composite sequence is checked for the presence of known B cell or linear T-cell epitopes. A search is performed, for example, with the publicly available IEDB. If a known epitope is found within the composite sequence, another set of human sequences is retrieved and substituted Unlike the resurfacing method of U.S. Pat. No. 5,639,641, both B-cell-mediated and T-cell-mediated immunogenic responses are addressed by the method. The method also avoids the issue of loss of activity that is sometimes observed with CDR grafting (U.S. Pat. No. 5,530,101). In addition, stability and solubility issues also are considered in the engineering and selection process, resulting in an antibody that is optimized for low immunogenicity, high antigen affinity and improved biophysical properties.

Strategies and methods for resurfacing antibodies, and other methods for reducing immunogenicity of antibodies within a different host, are disclosed, for example, in U.S. Pat. No. 5,639,641. Briefly, in a preferred method, (1) position alignments of a pool of antibody heavy and light chain variable regions are generated to yield heavy and light chain variable region framework surface exposed positions, wherein the alignment positions for all variable regions are at least about 98% identical; (2) a set of heavy and light chain variable region framework surface exposed amino acid residues is defined for a non-human, such as a rodent antibody (or fragment thereof); (3) a set of heavy and light chain variable region framework surface exposed amino acid residues that is most closely identical to the set of rodent surface exposed amino acid residues is identified; and (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of a CDR of the rodent antibody, to yield a humanized, such as a rodent antibody retaining binding specificity.

Antibodies can be humanized by a variety of other techniques including CDR grafting (EPO 0 239 400; WO 91/09967; and U.S. Pat. Nos. 5,530,101 and 5,585,089), veneering or resurfacing (EPO 0 592 106; EPO 0 519 596; Padlan, 1991, Molec Imm 28(4/5):489-498; Studnicka et al., 1994, Prot Eng 7(6):805-814; and Roguska et al., 1994, PNAS 91:969-973) and chain shuffling (U.S. Pat. No. 5,565, 332). Human antibodies can be made by a variety of methods known in the art including, but not limited to, phage display methods, see U.S. Pat. Nos. 4,444,887, 4,716,111, 5,545,806 and 5,814,318; and WO 98/46645, WO 98/50433, WO 98/24893, WO 98/16654, WO 96/34096, WO 96/33735 and WO 91/10741, using transgenic animals, such as rodents, using chimeric cells and so on.

"Antibody homolog" or "homolog" refers to any molecule which specifically binds IL-4 and/or IL-13 as taught herein. Thus, an antibody homolog includes native or recombinant antibody, whether modified or not, portions of antibodies that retain the biological properties of interest, such as binding IL-4 or IL-13, such as an $F_{ab}$ or $F_v$ molecule, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of a IL-4, IL-13 or bispecific IL-4/IL-13 antibody of the present invention. Preferably, homology is with the amino acid sequence of the variable regions of an antibody of the present invention. "Sequence homology" as applied to an amino acid sequence herein is defined as a sequence with at least about 90%, 91%, 92%, 93%, 94% or more sequence homology, and more preferably at least about 95%, 96%, 97%, 98% or 99% sequence homology to another amino acid sequence, as determined, for example, by the FASTA search method in accordance with Pearson & Lipman, Proc Natl Acad Sci USA 85, 2444-2448 (1988).

A chimeric antibody is one with different portions of an antibody derived from different sources, such as different antibodies, different classes of antibody, different animal species, for example, an antibody having a variable region derived from a murine monoclonal antibody paired with a human immunoglobulin constant region and so on. Thus, a humanized antibody is a species of chimeric antibody. Methods for producing chimeric antibodies are known in the art, see, e.g., Morrison, 1985, Science 229:1202; Oi et al., 1986, BioTechniques 4:214; Gillies et al., 1989, J Immunol Methods 125:191-202; and U.S. Pat. Nos. 5,807,715, 4,816, 567, and 4,816,397.

Artificial antibodies include scFv fragments, chimeric antibodies, diabodies, triabodies, tetrabodies and mru (see reviews by Winter & Milstein, 1991, Nature 349:293-299; and Hudson, 1999, Curr Opin Imm 11:548-557), each with antigen-binding or epitope-binding ability. In the single chain $F_v$ fragment ($scF_v$), the $V_H$ and $V_L$ domains of an antibody are linked by a flexible peptide. Typically, the linker is a peptide of about 15 amino acids. If the linker is much smaller, for example, 5 amino acids, diabodies are formed. The smallest binding unit of an antibody is a CDR, typically the CDR2 of the heavy chain which has sufficient specific recognition and binding capacity. Such a fragment is called a molecular recognition unit or mru. Several such mrus can be linked together with short linker peptides, therefore forming an artificial binding protein with higher avidity than a single mru.

Also included within the scope of the invention are functional equivalents of an antibody of interest. The term "functional equivalents" includes antibodies with homologous sequences, antibody homologs, chimeric antibodies, artificial antibodies and modified antibodies, for example, wherein each functional equivalent is defined by the ability to bind to IL-4 and/or IL-13, inhibiting IL-4 and/or IL-13 signaling ability or function, or inhibiting binding of IL-4 and/or IL-13 to its receptor. The skilled artisan will understand that there is an overlap in the group of molecules termed "antibody fragments" and the group termed "functional equivalents." Methods of producing functional equivalents which retain IL-4 and/or IL-13 binding ability are known to the person skilled in the art and are disclosed, for example, in WO 93/21319, EPO Ser. No. 239,400, WO 89/09622, EPO Ser. No. 338,745 and EPO Ser. No. 332,424.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein etc. The covalent attachment need not yield an antibody that is immune from generating an anti-idiotypic response. The modifications may be achieved by known techniques, including, but not limited to, specific chemical cleavage, acetylation, formylation, metabolic synthesis etc. Additionally, the modified antibodies may contain one or more non-classical amino acids.

Many techniques are available to one of ordinary skill in the art which permit the optimization of binding affinity. Typically, the techniques involve substitution of various amino acid residues at the site of interest, followed by a screening analysis of binding affinity of the mutant polypeptide for the cognate antigen or epitope.

Once the antibody is identified and isolated, it is often useful to generate a variant antibody or mutant, or mutein, wherein one or more amino acid residues are altered, for example, in one or more of the hypervariable regions of the antibody. Alternatively, or in addition, one or more alterations (e.g., substitutions) of framework residues may be introduced in the antibody where these result in an improvement in the binding affinity of the antibody mutant for IL-4 and/or IL-13. Examples of framework region residues that can be modified include those which non-covalently bind antigen directly (Amit et al., Science 233:747-753 (1986)); interact with/affect the conformation of a CDR (Chothia et al., J Mol Biol 196:901-917 (1987)); and/or participate in the $V_L$-$V_H$ interface (EP 239 400). In certain embodiments, modification of one or more of such framework region residues results in an enhancement of the binding affinity of the antibody for the cognate antigen. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant can comprise one or more hypervariable region alteration(s). The constant regions also can be altered to obtain desirable or more desirable effector properties.

The hypervariable region residues which are altered may be changed randomly, especially where the starting binding affinity of the parent antibody is such that randomly-produced antibody mutants can be readily screened for altered binding in an assay as taught herein.

One procedure for obtaining antibody mutants, such as CDR mutants, is "alanine scanning mutagenesis" (Cunningham & Wells, Science 244:1081-1085 (1989); and Cunningham & Wells, Proc Nat Acad Sci USA 84:6434-6437 (1991)). One or more of the hypervariable region residue(s) are replaced by alanine or polyalanine residue(s). Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues.

A more systematic method for identifying amino acid residues to modify comprises identifying hypervariable region residues involved in binding IL-4 and/or IL-13 and those hypervariable region residues with little or no involvement with IL-4 and/or IL-13 binding. An alanine scan of the non-binding hypervariable region residues is performed, with each ala mutant tested for enhancing binding to IL-4 and/or IL-13. In another embodiment, those residue(s) significantly involved in binding IL-4 and/or IL-13 are selected to be modified. Modification can involve deletion of a residue or insertion of one or more residues adjacent to a residue of interest. However, normally the modification involves substitution of the residue by another amino acid. A conservative substitution can be a first substitution. If such a substitution results in a change in biological activity (e.g., binding affinity), then another conservative substitution can be made to determine if more substantial changes are obtained.

Even more substantial modification in an antibody range and presentation of biological properties can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

For example, the naturally occurring amino acids can be divided into groups based on common side chain properties:

(1) hydrophobic: methionine (M or met), alanine (A or ala), valine (V or val), leucine (L or leu) and isoleucine (I or ile);

(2) neutral, hydrophilic: cysteine (C or cys), serine (S or ser), threonine (T or thr), asparagine (N or asn) and glutamine (Q or gin);

(3) acidic: aspartic acid (D or asp) and glutamic acid (E or glu);

(4) basic: histidine (H or his), lysine (K or lys) and arginine (R or arg);

(5) residues that influence chain orientation: glycine (G or gly) and proline (P or pro), and (6) aromatic: tryptophan (W or trp), tyrosine (Y or tyr) and phenylalanine (F or phe).

Non-conservative substitutions can entail exchanging an amino acid with an amino acid from another group. Conservative substitutions can entail exchange of one amino acid for another within a group.

Preferred amino acid substitutions include those which: (1) reduce susceptibility to proteolysis, (2) reduce susceptibility to oxidation, (3) alter binding affinity and (4) confer or modify other physico-chemical or functional properties of such analogs. Analogs can include various muteins of a sequence other than the naturally occurring peptide sequence. For example, single or multiple amino acid substitutions (preferably conservative amino acid substitutions) may be made in the naturally-occurring sequence (preferably in the portion of the polypeptide outside the domain (s)

forming intermolecular contacts. A conservative amino acid substitution should not substantially change the structural characteristics of the parent sequence (e. g., a replacement amino acid should not tend to break a helix that occurs in the parent sequence, or disrupt other types of secondary structure that characterizes the parent sequence) unless of a change in the bulk or conformation of the R group or side chain, Proteins, Structures and Molecular Principles (Creighton, ed., W. H. Freeman and Company, New York (1984)); Introduction to Protein Structure (Branden & Tooze, eds., Garland Publishing, New York, N.Y. (1991)); and Thornton et al. Nature 354:105 (1991).

Ordinarily, the antibody mutant with improved biological properties will have an amino acid sequence having at least 75% amino acid sequence identity or similarity with the amino acid sequence of either the heavy or light chain variable domain of the parent anti-human IL-4 and/or IL-13 antibody, at least 80%, at least 85%, at least 90% and often at least 95% identity. Identity or similarity with respect to parent antibody sequence is defined herein as the percentage of amino acid residues in the candidate sequence that are identical (i.e., same residue) or similar (i.e., amino acid residue from the same group based on common side-chain properties, supra) with the parent antibody residues, after aligning the sequences and introducing gaps, if necessary, to achieve the maximum percent sequence identity.

Alternatively, antibody mutants can be generated by systematic mutation of the FR and CDR regions of the heavy and light chains, or the $F_c$ region of the anti-IL-4, anti-IL-13 or bispecific IL-4/IL-13 antibody. Another procedure for generating antibody mutants involves the use of affinity maturation using phage display (Hawkins et al., J Mol Biol 254:889-896 (1992) and Lowman et al., Biochemistry 30(45):10832-10838(1991)). Bacteriophage coat-protein fusions (Smith, Science 228:1315 (1985); Scott & Smith, Science 249:386 (1990); Cwirla et al. Proc Natl Acad Sci USA 8:309 (1990); Devlin et al. Science 249:404 (1990); Wells & Lowman, Curr Opin Struct Biol 2:597 (1992); and U.S. Pat. No. 5,223,409) are known to be useful for linking the phenotype of displayed proteins or peptides to the genotype of bacteriophage particles which encode them. The $F_{ab}$ domains of antibodies have also been displayed on phage (McCafferty et al., Nature 348: 552 (1990); Barbas et al. Proc Natl Acad Sci USA 88:7978 (1991); and Garrard et al. Biotechnol 9:1373 (1991)).

Monovalent phage display consists of displaying a set of protein variants as fusions of a bacteriophage coat protein on phage particles (Bass et al., Proteins 8:309 (1990). Affinity maturation, or improvement of equilibrium binding affinities of various proteins, has previously been achieved through successive application of mutagenesis, monovalent phage display and functional analysis (Lowman & Wells, J Mol Biol 234:564 578 (1993); and U.S. Pat. No. 5,534,617), for example, by focusing on the CDR regions of antibodies (Barbas et al., Proc Natl Acad Sci USA 91:3809 (1994); and Yang et al., J Mol Biol 254:392 (1995)).

Libraries of many (for example, $10^6$ or more) protein variants, differing at defined positions in the sequence, can be constructed on bacteriophage particles, each of which contains DNA encoding the particular protein variant. After cycles of affinity purification, using an immobilized antigen, individual bacteriophage clones are isolated, and the amino acid sequence of the displayed protein is deduced from the DNA.

Following production of the antibody mutant, the biological activity of that molecule relative to the parent antibody can be determined as taught herein. As noted above, that may involve determining the binding affinity and/or other biological activities or physical properties of the antibody. In a preferred embodiment of the invention, a panel of antibody mutants is prepared and screened for binding affinity for the antigen. One or more of the antibody mutants selected from the screen are optionally subjected to one or more further biological activity assays to confirm that the antibody mutant(s) have new or improved properties. In preferred embodiments, the antibody mutant retains the ability to bind IL-4 and/or IL-13 with a binding affinity similar to or better/higher than that of the parent antibody.

The antibody mutant(s) so selected may be subjected to further modifications, often depending on the intended use of the antibody. Such modifications may involve further alteration of the amino acid sequence, fusion to heterologous polypeptide(s) and/or covalent modifications. For example, a cysteine residue not involved in maintaining the proper conformation of the antibody mutant may be substituted, generally with serine, to improve the oxidative stability of the molecule and to prevent aberrant cross-linking. Conversely, a cysteine may be added to the antibody to improve stability (particularly where the antibody is an antibody fragment such as an $F_v$ fragment).

Another type of antibody mutant has an altered glycosylation pattern. That may be achieved by deleting one or more carbohydrate moieties found in the antibody and/or by adding one or more glycosylation sites that are not present in the antibody. Glycosylation of antibodies is typically either N-linked to Asn or O-linked to Ser or Thr. The tripeptide sequences, asparagine-X-serine and asparagine-X-threonine, where X is any amino acid except proline, are common recognition sequences for enzymatic attachment of a carbohydrate moiety to the asparagine side chain. N-acetylgalactosamine, galactose, fucose or xylose, for example, are bonded to a hydroxyamino acid, most commonly serine or threonine, although 5-hydroxyproline or 5-hydroxylysine also may be used. Addition or substitution of one or more serine or threonine residues to the sequence of the original antibody can enhance the likelihood of O-linked glycosylation.

It may be desirable to modify the antibody of the invention with respect to effector function, so as to enhance the effectiveness of the antibody. For example, cysteine residue(s) may be introduced in the $F_c$ region, thereby allowing interchain disulfide bond formation in that region. The homodimeric antibody thus generated may have improved internalization capability and/or increased complement-mediated cell killing and antibody-dependent cellular cytotoxicity (ADCC), see Caron et al., J Exp Med 176:1191-1195 (1992) and Shopes, Immunol 148:2918-2922 (1993). Alternatively, an antibody can be engineered which has dual $F_c$ regions and may thereby have enhanced complement lysis and ADCC capabilities, see Stevenson et al., Anti-Cancer Drug Design 3: 219 230 (1989).

Covalent modifications of the antibody are included within the scope of the invention. Such may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or with the N-terminal or C-terminal residue.

Cysteinyl residues can be reacted with α-haloacetates (and corresponding amines), such as chloroacetic acid or chloroacetamide, to yield carboxylmethyl or carboxyamidomethyl derivatives. Cysteinyl residues also can be derivatized by reaction with bromotrifluoroacetone, α-bromo-β-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercura-4-nitrophenol or chloro-7-nitrobenzo-2-oxa-1,3-diazole, for example.

Histidyl residues can be derivatized by reaction with diethylpyrocarbonate at pH 5.5-7.0. p-bromophenacyl bromide also can be used, the reaction is preferably performed in 0.1 M sodium cacodylate at pH 6.0.

Lysinyl and α terminal residues can be reacted with succinic or other carboxylic acid anhydrides to reverse the charge of the residues. Other suitable reagents for derivatizing α-amino-containing residues include imidoesters, such as methyl picolinimidate, pyridoxal phosphate, pyridoxal, chloroborohydride, trinitrobenzenesulfonic acid, O-methylisourea and 2,4-pentanedione, and the amino acid can be transaminase-catalyzed with glyoxylate.

Arginyl residues can be modified by reaction with one or several conventional reagents, such as phenylglyoxal, 2,3-butanedione, 1,2-cyclohexanedione and ninhydrin. Derivatization of arginine residues often requires alkaline reaction conditions. Furthermore, the reagents may react with lysine as well as the arginine ε-amino group.

The specific modification of tyrosyl residues can be made with aromatic diazonium compounds or tetranitromethane. For example, N-acetylimidizole and tetranitromethane are used to form O-acetyl tyrosyl species and 3-nitro derivatives, respectively. Tyrosyl residues can be iodinated using $^{125}I$ or $^{131}I$ to prepare labeled proteins for use in a radioimmunoassay.

Carboxyl side groups (aspartyl or glutamyl) can be modified by reaction with carbodiimides (R—N=C=C—R'), where R and R' can be different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonium ions.

Glutaminyl and asparaginyl residues are frequently deamidated to the corresponding glutamyl and aspartyl residues, respectively, under neutral or basic conditions. The deamidated form of those residues falls within the scope of this invention.

Other modifications include hydroxylation of proline and lysine, phosphorylation of hydroxyl groups of serinyl or threonyl residues, methylation of the α-amino groups of lysine, arginine, and histidine side chains (Creighton, Proteins: Structure and Molecular Properties, W.H. Freeman & Co., San Francisco, pp. 79-86 (1983)), acetylation of the N-terminal amine and amidation of any C-terminal carboxyl group.

Another type of covalent modification involves chemically or enzymatically coupling glycosides to the antibody. Those procedures do not require production of the antibody in a host cell that has glycosylation capabilities for N-linked or O-linked glycosylation. Depending on the coupling mode used, the sugar(s) may be attached to: (a) arginine and histidine; (b) free carboxyl groups; (c) free sulfhydryl groups, such as those of cysteine; (d) free hydroxyl groups, such as those of serine, threonine or hydroxyproline; (e) aromatic residues such as those of phenylalanine, tyrosine or tryptophan: or (f) the amide group of glutamine. Such methods are described in WO 87/05330 and in Aplin & Wriston, CRC Crit Rev Biochem, pp. 259-306 (1981).

Removal of any carbohydrate moieties present on the antibody may be accomplished chemically or enzymatically. Chemical deglycosylation, for example, can require exposure of the antibody to the compound, trifluoromethanesulfonic acid, or an equivalent compound, resulting in cleavage of most or all sugars except the linking sugar (N-acetylglucosamine or N-acetylgalactosamine), while leaving the antibody intact. Chemical deglycosylation is described, for example, in Hakimuddin et al. Arch Biochem Biophys 259:52 (1987) and in Edge et al., Anal Biochem 118:131 (1981). Enzymatic cleavage of carbohydrate moieties on antibodies can be achieved by any of a variety of endoglycosidases and exoglycosidases as described, for example, in Thotakura et al., Meth Enzymol 138:350(1987).

Another type of covalent modification of the antibody comprises linking the antibody to one of a variety of nonproteinaceous polymers, e.g., polyethylene glycol, polypropylene glycol or polyoxylalkylenes, in the manner set forth in U.S. Pat. Nos. 4,640,835; 4,496,689; 4,301,144; 4,670,417; 4,791,192 or 4,179,337.

Another technique preferred for obtaining mutants or muteins is affinity maturation by phage display (Hawkins et al., J Mol Biol 254:889-896 (1992); and Lowman et al., Biochemistry 30(45):10832-10838 (1991)). Briefly, several hypervariable region sites (e.g., 6-7 sites) are mutated to generate all possible amino acid substitutions at each site. The antibody mutants thus generated are displayed in monovalent fashion on phage particles as fusions to a protein found on the particles. The phage expressing the various mutants can be cycled through rounds of binding selection, followed by isolation and sequencing of those mutants which display high affinity.

The method of selecting novel binding polypeptides can utilize a library of structurally related polypeptides. The library of structurally related polypeptides, for example, fused to a phage coat protein, is produced by mutagenesis, and is displayed on the surface of the particle. The particles then are contacted with a target molecule and those particles having the highest affinity for the target are separated from those of lower affinity. The high affinity binders then are amplified by infection of a suitable bacterial host and the competitive binding step is repeated. The process is repeated until polypeptides of the desired affinity are obtained.

Alternatively, multivalent phage (McCafferty et al. (1990) Nature 348:552-554; and Clackson et al. (1991) Nature 352:624-628) also can be used to express random point mutations (for example, generated by use of an error-prone DNA polymerase) to generate a library of phage antibody fragments which then could be screened for affinity to IL-4 and/or IL-13, Hawkins et al., (1992) J Mol Biol 254:889-896.

Preferably, during the affinity maturation process, the replicable expression vector is under tight control of a transcription regulatory element, and the culturing conditions are adjusted so the amount or number of particles displaying more than one copy of the fusion protein is less than about 1%. Also preferably, the amount of particles displaying more than one copy of the fusion protein is less than 10% of the amount of particles displaying a single copy of the fusion protein. Preferably the amount is less than 20%.

Functional equivalents may be produced by interchanging different CDRs of different antibody chains within a framework or a composite FR derived from plural antibodies. Thus, for example, different classes of antibody are possible for a given set of CDRs by substitution of different heavy chains, for example, $IgG_{1-4}$, IgM, $IgA_{1-2}$ or IgD, to yield differing IL-4 and/or IL-13 antibody types and isotypes. Similarly, artificial antibodies within the scope of the invention may be produced by embedding a given set of CDRs within an entirely synthetic framework.

The antibody fragments and functional equivalents of the present invention encompass those molecules with a detectable degree of specific binding to IL-4 and/or IL-13. A detectable degree of binding includes all values in the range of at least 10-100%, preferably at least 50%. 60% or 70%, more preferably at least 75%, 80%, 85%, 90%, 95% or 99% of the binding ability of an antibody of interest. Also included are equivalents with an affinity greater than 100% that of an antibody of interest.

The CDRs generally are of importance for epitope recognition and antibody binding. However, changes may be made to residues that comprise the CDRs without interfering with the ability of the antibody to recognize and to bind the cognate epitope. For example, changes that do not impact epitope recognition, yet increase the binding affinity of the antibody for the epitope, may be made. Several studies have surveyed the effects of introducing one or more amino acid changes at various positions in the sequence of an antibody, based on the knowledge of the primary antibody sequence, on the properties thereof, such as binding and level of expression (Yang et al., 1995, J Mol Biol 254:392-403; Rader et al., 1998, Proc Natl Acad Sci USA 95:8910-8915; and Vaughan et al., 1998, Nature Biotechnology 16, 535-539).

Thus, equivalents of an antibody of interest can be generated by changing the sequences of the heavy and light chain genes in the CDR1, CDR2 or CDR3, or framework regions, using methods such as oligonucleotide-mediated site-directed mutagenesis, cassette mutagenesis, error-prone PCR. DNA shuffling or mutator-strains of E. coli (Vaughan et al., 1998, Nat Biotech 16:535-539; and Adey et al., 1996, Chap. 16, pp. 277-291, in Phage Display of Peptides and Proteins, eds. Kay et al., Academic Press). The methods of changing the nucleic acid sequence of the primary antibody can result in antibodies with improved affinity (Gram et al., 1992, Proc Natl Acad Sci USA 89:3576-3580; Boder et al., 2000, Proc Natl Acad Sci USA 97:10701-10705; Davies & Riechmann, 1996, Immunotech 2:169-179; Thompson et al., 1996, J Mol Biol 256:77-88; Short et al., 2002, J Biol Chem 277:16365-16370; and Furukawa et al., 2001, J Biol Chem 276:27622-27628).

Repeated cycles of "polypeptide selection" can be used to select for higher and higher affinity binding by, for example, the selection of multiple amino acid changes which are selected by multiple selections of cycles. Following a first round of selection, involving a first region of selection of amino acids in the ligand or antibody polypeptide, additional rounds of selection in other regions or amino acids of the ligand are conducted. The cycles of selection are repeated until the desired affinity properties are achieved.

Improved antibodies also include those antibodies having improved characteristics that are prepared by the standard techniques of animal immunization, hybridoma formation and selection for antibodies with specific characteristics.

"Antagonist" refers to a molecule capable of inhibiting one or more biological activities of a target molecule, such as signaling by IL-4 and/or IL-13. Antagonists may interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist may completely block receptor-ligand interactions or may substantially reduce such interactions.

"Agonist" refers to a compound, including a protein, a polypeptide, a peptide, an antibody, an antibody fragment, a conjugate, a large molecule, a small molecule, which activates one or more biological activities of IL-4 and/or IL-13. Agonists may interact with the binding of a receptor to a ligand and vice versa, by acting as a mitogen of cells activated by a ligand, and/or by interfering with cell inactivation or signal transduction inhibition after ligand binding to a receptor. All such points of intervention by an agonist shall be considered equivalent for purposes of the instant invention.

The terms "cell," "cell line," and "cell culture" include progeny thereof. It is also understood that all progeny may not be precisely identical, such as in DNA content, due to deliberate or inadvertent mutation. Variant progeny that have the same function or biological property of interest, as screened for in the original cell, are included.

The term "vector" means a nucleic acid construct, a carrier, containing a nucleic acid, the transgene, the foreign gene or the gene of interest, which can be operably linked to suitable control sequences for expression of the transgene in a suitable host. Such control sequences include, for example, a promoter to effect transcription, an optional operator sequence to control such transcription, a sequence encoding suitable mRNA ribosome binding sites and sequences which control the termination of transcription and translation. The vector may be a plasmid, a phage particle or just a potential genomic insert. Once transformed into a suitable host, the vector may replicate and function independently of the host genome, or may in some instances, integrate into the host cell genome. In the present specification, "plasmid" and "vector" are used interchangeably, as the plasmid is a commonly used form of vector. However, the invention is intended to include such other forms of vectors which serve equivalent carrier function as and which are, or become, known in the art, such as viruses, synthetics molecules that carry nucleic acids, liposomes and the like.

"Mammal" for purposes of treatment refers to any animal classified as a mammal, including human, domestic and farm animals, nonhuman primates, and zoo, sports or pet animals, such as dogs, horses, cats, cows etc.

The antibodies of interest can be screened or can be used in an assay as described herein or as known in the art. Often, such assays require a reagent to be detectable, that is, for example, labeled. The word "label" when used herein refers to a detectable compound or composition which can be conjugated directly or indirectly to a molecule or protein, e.g., an antibody. The label may itself be detectable (e.g., radioisotope labels, particles or fluorescent labels) or, in the case of an enzymatic label, may catalyze chemical alteration of a substrate compound or composition which is detectable.

As used herein, "solid phase" means a non-aqueous matrix to which an entity or molecule, such as the antibody of the instant invention, can adhere. Example of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others can be used in a purification column (e.g., an affinity chromatography column). Thus, the solid phase can be a paper, a bead, a plastic, a chip and so on, can be made from a variety of materials, such as nitrocellulose, agarose, polystyrene, polypropylene, silicon and so on, and can be in a variety of configurations.

The gene or a cDNA encoding IL-4 and IL-13 are known in the art, may be cloned in a plasmid or other expression vector and expressed in any of a number of expression systems according to methods well known to those of skill in the art, and see below, for example.

Nucleic acid molecules encoding amino acid sequence mutants can be prepared by a variety of methods known in the art. The methods include, but are not limited to, oligonucleotide-mediated (or site-directed) mutagenesis, PCR mutagenesis and cassette mutagenesis of an earlier prepared mutant or a non-mutant version of the molecule of interest, (see, for example, Kunkel, Proc Natl Acad Sci USA 82:488 (1985)).

Recombinant expression of an antibody of the invention, or fragment, derivative or analog thereof, (e.g., a heavy or light chain of an antibody of the invention, a single chain antibody of the invention or an antibody mutein of the invention) includes construction of an expression vector containing a polynucleotide that encodes the antibody or a fragment of the antibody as described herein. Once a polynucleotide encoding an antibody molecule has been obtained, the vector for the production of the antibody may be produced by recombinant DNA technology as known in the art. An expression vector is constructed containing antibody coding sequences and appropriate transcriptional and translational control signals. The methods include, for example, in vitro recombinant DNA techniques, synthetic techniques and in vivo genetic recombination.

The expression vector is transferred to a host cell by conventional techniques and the transfected cells then are cultured by conventional techniques to produce an antibody or fragment of the invention. In one aspect of the invention, vectors encoding both the heavy and light chains may be co-expressed in the host cell for expression of the entire immunoglobulin molecule, as detailed herein.

A variety of host/expression vector systems may be utilized to express the antibody molecules of the invention. Such expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells, such as *E. coli*, and eukaryotic cells are commonly used for the expression of a recombinant antibody molecule, especially for the expression of whole recombinant antibody molecule. For example, mammal cells such as CHO cells, in conjunction with a vector, such as one carrying the major intermediate early gene promoter element from human cytomegalovirus, are an effective expression system for antibodies (Foecking et al., Gene 45:101 (1986); and Cockett et al., Bio/Technology 8:2 (1990)). Plants and plant cell culture, insect cells and so on also can be used to make the proteins of interest, as known in the art.

In addition, a host cell is chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the expressed antibody of interest. Hence, eukaryotic host cells which possess the cellular machinery for proper processing of the primary transcript, glycosylation and phosphorylation of the gene product may be used. Such mammalian host cells include, but are not limited to, CHO, COS, 293, 3T3 or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites etc.) and a selectable marker. Following the introduction of the foreign DNA, engineered cells may be allowed to grow for one to two days in an enriched media, and then are moved to a selective media. The selectable marker in the recombinant plasmid confers resistance to the selection and allows cells to stably integrate the plasmid into a chromosome and be expanded into a cell line. Such engineered cell lines not only are useful for antibody production but are useful in screening and evaluation of compounds that interact directly or indirectly with the antibody molecule.

A number of selection systems may be used, including but not limited to the Herpes simplex virus thymidine kinase (Wigler et al., Cell 11:223 (1977)), hypoxanthine-guanine phosphoribosyltransferase (Szybalska et al., Proc Natl Acad Sci USA 48:202 (1992)), glutamate synthase selection in the presence of methionine sulfoximide (Adv Drug Del Rev 58, 671, 2006 and see the website or literature of Lonza Group Ltd.) and adenine phosphoribosyltransferase (Lowy et al., Cell 22:817 (1980)) genes in tk, hgprt or aprt cells, respectively. Also, antimetabolite resistance can be used as the basis of selection for the following genes: dhfr, which confers resistance to methotrexate (Wigler et al., Proc Natl Acad Sci USA 77:357 (1980); O'Hare et al., Proc Natl Acad Sci USA 78:1527 (1981)); gpt, which confers resistance to mycophenolic acid (Mulligan et al., Proc Natl Acad Sci USA 78:2072 (1981)); neo, which confers resistance to the aminoglycoside, G-418 (Wu et al., Biotherapy 3:87 (1991)); and hygro, which confers resistance to hygromycin (Santerre et al., Gene 30:147 (1984)). Methods known in the art of recombinant DNA technology may be routinely applied to select the desired recombinant clone, and such methods are described, for example, in Ausubel et al., eds., Current Protocols in Molecular Biology, John Wiley & Sons (1993); Kriegler, Gene Transfer and Expression, A Laboratory Manual, Stockton Press (1990); Dracopoli et al., eds., Current Protocols in Human Genetics, John Wiley & Sons (1994); and Colberre-Garapin et al., J Mol Biol 150:1 (1981).

The expression levels of an antibody molecule can be increased by vector amplification (for example, see Bebbington et al., in DNA Cloning, Vol. 3. Academic Press (1987)). When a marker in the vector system expressing antibody is amplifiable, an increase in the level of inhibitor present in the culture will increase the number of copies of the marker gene. Since the amplified region is associated with the antibody gene, production of the antibody will also increase (Crouse et al., Mol Cell Biol 3:257 (1983)).

The host cell may be co-transfected with two or more expression vectors of the invention, for example, the first vector encoding a heavy chain-derived polypeptide and the second vector encoding a light chain-derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); and Kohler, Proc Natl Acad Sci USA 77:2197 (1980)). The coding sequences for the heavy and light chains may comprise cDNA or genomic DNA.

Once an antibody molecule of the invention has been produced by an animal, chemically synthesized or recombinantly expressed, it may be purified by any method known in the art for purification of an immunoglobulin molecule, for example, by chromatography (e.g., ion exchange, affinity, particularly by affinity for IL-4 and/or IL-13 after Protein A and size-exclusion chromatography and so on), centrifugation, differential solubility or by any other standard technique for the purification of proteins. In addition, the antibodies of the instant invention or fragments thereof can be fused to heterologous polypeptide sequences described herein or otherwise known in the art, to facilitate purification.

The antibodies of the present invention may be generated by any suitable method known in the art. The antibodies of the present invention may comprise polyclonal antibodies, although because of the modification of antibodies to optimize use in human, as well as to optimize the use of the antibody per se, monoclonal antibodies are preferred because of ease of production and manipulation of particular proteins. Methods of preparing polyclonal antibodies are known to the skilled artisan (Harlow et al., Antibodies: a Laboratory Manual, Cold Spring Harbor Laboratory Press, 2nd ed. (1988)).

The antibodies of the present invention preferably comprise monoclonal antibodies. Monoclonal antibodies may be prepared using hybridoma technology, such as described by Kohler et al., Nature 256:495 (1975); U.S. Pat. No. 4,376, 110; Harlow et al., Antibodies: A Laboratory Manual, Cold Spring Harbor Laboratory Press, 2nd ed. (1988) and Hammerling et al., Monoclonal Antibodies and T-Cell Hybridomas, Elsevier (1981), recombinant DNA methods, for example, making and using transfectomas, or other methods known to the artisan. Other examples of methods which may be employed for producing monoclonal antibodies include, but are not limited to, the human B-cell hybridoma technique (Kosbor et al., Immunology Today 4:72 (1983); and Cole et al., Proc Natl Acad Sci USA 80:2026 (1983)), and the EBV-hybridoma technique (Cole et al., Monoclonal Antibodies and Cancer Therapy, pp. 77-96, Alan R. Liss (1985)). Such antibodies may be of any immunoglobulin class including IgG, IgM, IgE, IgA and IgD, and any subclass thereof. The hybridoma producing the mAb of the invention may be cultivated in vitro or in vivo.

In the hybridoma model, a host such as a mouse, a humanized mouse, a transgenic mouse with human immune system genes, hamster, rabbit, rat, camel or any other appropriate host animal, is immunized to elicit lymphocytes that produce or are capable of producing antibodies that specifically bind to IL-4 or IL-13. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, Academic Press, pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin and thymidine ("HAT medium"), substances that prevent the growth of HGPRT-deficient cells.

Preferred immortalized cell lines are those that fuse efficiently, support stable high level production of antibody by the selected antibody-producing cells, and are sensitive to a medium such as HAT medium. Among these myeloma cell lines are murine myeloma lines, such as those derived from the MOPC-21 and MPC-11 mouse tumors available from the Salk Institute Cell Distribution Center, San Diego, Calif. and SP2/0 FO or X63-Ag8-653 cells available from the American Type Culture Collection, Manassas, Va.

Human myeloma and mouse-human heteromyeloma cell lines also have been described for the production of human monoclonal antibodies (Kozbor, J Immunol 133:3001 (1984); and Brodeur et al., Monoclonal Antibody Production Techniques and Applications, Marcel Dekker, Inc, pp. 51-63 (1987)). The mouse myeloma cell line NSO may also be used (European Collection of Cell Cultures, Salisbury, Wilshire, UK).

Another alternative is to use electrical fusion rather than chemical fusion to form hybridomas. Instead of fusion, a B cell can be immortalized using, for example, Epstein Barr Virus or another transforming gene, see, e.g., Zurawaki et al., in Monoclonal Antibodies, ed., Kennett et al., Plenum Press, pp. 19-33. (1980). Transgenic mice expressing immunoglobulins and severe combined immunodeficient (SCID) mice transplanted with human B lymphocytes also can be used.

The culture medium in which hybridoma cells are grown is assayed for production of monoclonal antibodies directed against IL-4 and/or IL-13. The binding specificity of monoclonal antibodies produced by hybridoma cells may be determined by immunoprecipitation or by an in vitro binding assay, such as radioimmunoassay (RIA), fluorocytometric analysis (FACS) or enzyme-linked immunosorbent assay (ELISA). Such techniques are known in the art and are within the skill of the artisan. The binding affinity of the monoclonal antibody to IL-4 and/or IL-13 can, for example, be determined by a Scatchard analysis (Munson et al., Anal Biochem 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, Academic Press, pp. 59-103 (1986)). Suitable culture media include, for example, Dulbecco's Modified Eagle's Medium (D-MEM) or RPMI-1640 medium. In addition, the hybridoma cells may be grown in vivo as ascites tumors in an animal.

The monoclonal antibodies secreted by the subclones are suitably separated or isolated from the culture medium, ascites fluid or serum by conventional immunoglobulin purification procedures such as, for example, protein A-Sepharose, protein G-Sepharose, hydroxylapatite chromatography, gel exclusion chromatography, gel electrophoresis, dialysis or affinity chromatography.

A variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage or prokaryotic clone.

DNA encoding the monoclonal antibodies of the invention is readily isolated and sequenced using conventional procedures (e.g., by using oligonucleotide probes that are capable of binding specifically to genes encoding the heavy and light chains of murine antibodies, or such chains from human, humanized or other sources) (Innis et al. in PCR Protocols. A Guide to Methods and Applications, Academic (1990), and Sanger et al., Proc Natl Acad Sci 74:5463 (1977)). The hybridoma cells serve as a source of such DNA. Once isolated, the DNA may be placed into expression vectors, which are then transfected into host cells such as E. coli cells, NSO cells, COS cells, Chinese hamster ovary (CHO) cells or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; and Morrison et al., Proc Natl Acad Sci USA 81:6851 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one IL-4 or IL-13 combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the $F_c$ region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. Traditionally, these fragments were derived via proteolytic digestion of intact antibodies (see, e.g., Morimoto et al., J Biochem Biophys Methods 24:107 (1992); and Brennan et al., Science 229:81 (1985)). For example, $F_{ab}$ and $F_{(ab')2}$ fragments of the invention may be produced by proteolytic cleavage of immunoglobulin molecules, using enzymes such as papain (to produce $F_{ab}$ fragments) or pepsin (to produce $F_{(ab')2}$ fragments). $F_{(ab')2}$ fragments contain the variable region, the light chain constant region and the $C_{H1}$ domain of the heavy chain. However, those fragments can be produced directly by recombinant host cells. For example, the antibody fragments can be isolated from an antibody phage library. Alternatively, $F_{(ab')2}$-SH fragments can be directly recovered from E. coli and chemically coupled to form F(ab')$_2$ fragments (Carter et al., Bio/Technology 10:163 (1992). According to another approach, $F_{(ab')2}$ fragments can be isolated directly from recombinant host cell culture. Other techniques for the production of antibody fragments will be apparent to the skilled practitioner. In other embodiments, the antibody of choice is a single chain $F_v$ fragment ($F_v$) (WO 93/16185).

For some uses, including in vivo use of antibodies in humans and in vitro detection assays, it may be preferable to use chimeric, humanized or human antibodies. Methods for producing chimeric antibodies are known in the art, see e.g., Morrison, Science 229:1202 (1985); Oi et al., BioTechniques 4:214 (1986); Gillies et al., J Immunol Methods 125:191 (1989); and U.S. Pat. Nos. 5,807,715; 4,816,567; and 4,816397.

Humanized antibodies are derived from antibody molecules generated in a non-human species that bind IL-4 and/or IL-13 wherein one or more CDRs therefrom are inserted into the FR regions from a human immunoglobulin molecule. Antibodies can be humanized using a variety of techniques known in the art including, for example, CDR grafting (EPO 239,400; WO 91/09967; and U.S. Pat. Nos. 5,225,539; 5,530,101; and 5,585,089), veneering or resurfacing (EPO 592.106; EPO 519,596; Padlan, Molecular Immunology 28:489 (1991); Studnicka et al., Protein Engineering 7:805 (1994); and Roguska et al., Proc Natl Acad Sci USA 91:969 (1994)), and chain shuffling (U.S. Pat. No. 5,565,332).

A humanized antibody has one or more amino acid residues from a source that is non-human. The non-human amino acid residues are often referred to as "import" residues, which are typically taken from an "import" variable domain. Humanization can be essentially performed following the methods of Winter and co-workers (Jones et al., Nature 321:522 (1986); Riechmann et al., Nature 332:323 (1988); and Verhoeyen et al., Science 239:1534 (1988)), by substituting non-human CDRs or portions of CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies. The heavy chain constant region and hinge region can be from any class or subclass to obtain a desired effect, such as a particular effector function.

Often, framework residues in the human framework regions can be substituted with the corresponding residue from the CDR donor antibody to alter, and possibly improve, antigen binding. The framework substitutions are identified by methods known in the art, e.g., by modeling of the interactions of the CDR and framework residues to identify framework residues important for antigen binding and sequence comparison to identify unusual framework residues at particular positions, see, e.g., U.S. Pat. No. 5,585,089; and Riechmann et al., Nature 332:323 (1988).

It is further preferable that humanized antibodies retain high affinity for IL-4 and/or IL-13, and retain or acquire other favorable biological properties. Thus, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of the displays permits analysis of the likely role of certain residues in the functioning of the candidate immunoglobulin sequence, i.e., the analysis of residues that influence the ability of the candidate immunoglobulin to bind IL-4 and/or IL-13. In that way, FR residues can be selected and combined from the recipient and import sequences so that the desired antibody characteristic, such as increased affinity for the target antigen, is maximized, although it is the CDR residues that directly and most substantially influence IL-4 or IL-13 binding. The CDR regions also can be modified to contain one or more amino acids that vary from that obtained from the parent antibody from which the CDR was obtained, to provide enhanced or different properties of interest, such as binding of greater affinity or greater avidity, for example.

Certain portions of the constant regions of antibody can be manipulated and changed to provide antibody homologs, derivatives, fragments and the like with properties different from or better than that observed in the parent antibody. Thus, for example, many IgG4 antibodies form intrachain disulfide bonds near the hinge region. The intrachain bond can destabilize the parent bivalent molecule forming monovalent molecules comprising a heavy chain with the associated light chain. Such molecules can reassociate, but on a random basis.

It was observed that modifying amino acids in the hinge region of IgG4 molecules can reduce the likelihood of intrachain bond formation, thereby stabilizing the IgG4 molecule, which will minimize the likelihood of forming bispecific molecules. That modification can be beneficial if a therapeutic antibody is an IgG4 molecule as the enhanced stability will minimize the likelihood of having the molecule dissociate during production and manufacture, as well as in vivo. A monovalent antibody may not have the same effectiveness as the bivalent parent molecule. For example, when bivalent IgG4 is administered to a patient, the percentage of bivalent IgG4 decays to about 30% over a two-week period. An amino acid substitution at position 228 enhances IgG4 stability. The serine that resides at 228 can be replaced with another amino acid, such as one of the remaining 19 amino acids. Such a change can be made particularly with recombinant antibodies wherein the nucleic acid coding sequence can be mutated to yield a replacement amino acid at position 228. For example, the S can be replaced with a proline.

Another set of amino acids suitable for modification include amino acids in the area of the hinge which impact binding of a molecule containing a heavy chain with binding to the $F_c$ receptor and internalization of bound antibody. Such amino acids include, in IgG1 molecules, residues from about 233 to about 237 (Glu-Leu-Leu-Gly-Gly); (SEQ ID NO:49) from about 252 to about 256 (Met-Ile-Ser-Arg-Thr) (SEQ ID NO:50) and from about 318 (Glu) to about 331 (Pro), including, for example, $Lys_{320}$, $Lys_{322}$ and $Pro_{329}$.

Completely human antibodies are particularly desirable for therapeutic treatment of human patients. Human antibodies can be made by a variety of methods known in the art including phage display methods described above using antibody libraries derived from human immunoglobulin sequences, see, U.S. Pat. Nos. 4,444,887 and 4,716,111; and WO 98/46645, WO 98/50433, WO 98/24893, WO 98/16654, WO 96/34096, WO 96/33735 and WO 91/10741. The techniques of Cole et al. and Boerder et al. are also available for the preparation of human monoclonal antibodies (Cole et al., Monoclonal Antibodies and Cancer Therapy, Alan R. Liss (1985); and Boerner et al., J Immunol 147:86 (1991)).

Human antibodies can also be produced using transgenic mice which are incapable of expressing functional endogenous immunoglobulins, but which also express certain human immunoglobulin genes. For example, the human heavy and light chain immunoglobulin gene complexes may be introduced randomly or by homologous recombination into mouse embryonic stem cells. Alternatively, the human variable region, constant region and diversity region may be introduced into mouse embryonic stem cells, in addition to the human heavy and light chain genes. The mouse heavy and light chain immunoglobulin genes may be rendered non-functional separately or simultaneously with the introduction of the human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies, see, e.g., Jakobovitis et al., Proc Natl Acad Sci USA 90:2551 (1993); Jakobovitis et al., Nature 362:255 (1993); Bruggermann et al., Year in Immunol 7:33 (1993); and Duchosal et al., Nature 355:258 (1992)).

The transgenic mice are immunized in the normal fashion with IL-4 or IL-13 cytokine, e.g., all or a portion of IL-4 or IL-13 Monoclonal antibodies directed against IL-4 and IL-13 can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview, see Lonberg et al., Int Rev Immunol 13:65-93 (1995). For a discussion of producing human antibodies and human monoclonal antibodies and protocols for producing such antibodies, see, e.g., WO 98/24893; WO 92/01047; WO 96/34096; and WO 96/33735; EPO No. 0 598 877; and U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Amgen (Fremont, Calif.), Genpharm (San Jose, Calif.) and Medarex, Inc. (Princeton, N.J.) can be engaged to provide human antibodies directed against IL-4 and/or IL-13 using technology similar to that described above.

Also, human mAbs could be made by immunizing mice transplanted with human peripheral blood leukocytes, splenocytes or bone marrow (e.g., trioma technique of XTL Biopharmaceuticals, Israel). Completely human antibodies which recognize a selected epitope can be generated using a technique referred to as "guided selection." In that approach, a selected non-human monoclonal antibody, e.g., a mouse antibody is used to guide the selection of a completely human antibody recognizing the same epitope (Jespers et al., Bio/technology 12:899 (1988)).

When using recombinant techniques, the antibody variant can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter et al., Bio/Technology 10:163 (1992) describe a procedure for isolating antibodies which are secreted to the periplasmic space of *E. coli*. Briefly, cell paste is exposed to sodium acetate (pH 3.5) and EDTA. Cell debris can be removed by centrifugation. Where the antibody variant is secreted into the medium, supernatant from such expression systems are generally first concentrated using a commercially available protein concentration filter, for example, an Amicon or Millipore Pellicon ultrafiltration unit. A protease inhibitor such as PMSF may be included to inhibit proteolysis, and antibiotics may be included to prevent growth of adventitious contaminants.

The antibody composition prepared from the cells can be purified using, for example, hydroxylapatite chromatography, gel electrophoresis, dialysis and affinity chromatography. The suitability of protein A or protein G as an affinity ligand depends on the species and isotype of any immunoglobulin $F_c$ domain that is present in the antibody variant. Protein A can be used to purify antibodies that are based on human IgG1, IgG2 or IgG4 heavy chains (Lindmark et al., J Immunol Meth 62:1 (1983)). Protein G can be used for mouse isotypes and for human IgG3 (Guss et al., EMBO J 5:1567 (1986)). The matrix to which the affinity ligand is attached is most often agarose, but other matrices are available. Mechanically stable matrices, such as controlled pore glass or poly(styrenedivinyl)benzene, allow for faster flow rates and shorter processing times than can be achieved with agarose. Where the antibody variant comprises a $C_{H3}$ domain, the Bakerbond ABX™ resin (JT Baker; Phillipsburg, N.J.) is useful for purification. Other techniques for protein purification, such as fractionation on an ion-exchange column, ethanol precipitation, reverse phase HPLC, chromatography on silica, chromatography on heparin agarose chromatography on an anion or cation exchange resin (such as a polyaspartic acid column), chromatofocusing, SDS-PAGE and ammonium sulfate precipitation are also available, depending on the antibody or variant to be recovered.

Following any preliminary purification step(s), the mixture comprising the antibody or variant of interest and contaminants may be subjected to low pH hydrophobic interaction chromatography using an elution buffer at a pH of between about 2.5-4.5, preferably performed at low salt concentrations (e.g., from about 0-0.25 M salt).

The antibodies of the present invention may be bispecific antibodies. Bispecific antibodies can be monoclonal, preferably human or humanized, antibodies that have binding specificities for at least two different antigens. In a preferred embodiment, the bispecific antibody, fragment thereof and so on has binding specificities directed towards IL-4 and IL-13.

Methods for making bispecific antibodies are well known. Traditionally, the recombinant production of bispecific antibodies is based on the co-expression of two immunoglobulin heavy chain/light chain pairs, where the two heavy chains have different specificities (Milstein et al., Nature 305:537 (1983)). Because of the random assortment of immunoglobulin heavy and light chains, the hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., EMBO J 10:3655 (1991). Other methods for making bispecific antibodies are provided in, for example, Kufer et al., Trends Biotech 22:238-244, 2004.

Antibody variable domains with the desired binding specificities can be fused to immunoglobulin constant domain sequences. The fusion preferably is with an immunoglobulin heavy chain constant domain, comprising at least part of the hinge, $C_{H2}$, and $C_{H3}$ regions. It may have the first heavy chain constant region ($C_{H1}$) containing the site necessary for light chain binding present in at least one of the fusions. DNAs encoding the immunoglobulin heavy chain fusions and, if desired, the immunoglobulin light chain, are inserted into separate expression vectors, and are co-transformed into a suitable host organism. For further details of generating bispecific antibodies see, for example Suresh et al., Meth Enzym 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for that purpose include iminothiolate and methyl-4-mercaptobutyrimidate, and those disclosed, for example, in U.S. Pat. No. 4,676,980.

In addition, one can generate single-domain antibodies to IL-4 and/or IL-13. Examples of that technology have been described in WO9425591 for antibodies derived from Camelidae heavy chain Ig, as well as in US20030130496 describing the isolation of single domain fully human antibodies from phage libraries.

Alternatively, techniques described for the production of single chain antibodies (U.S. Pat. No. 4,946,778; Bird, Science 242:423 (1988); Huston et al., Proc Natl Acad Sci USA 85:5879 (1988); and Ward, et al., Nature 334:544 (1989)) can be adapted to produce single chain antibodies. Single chain antibodies are formed by linking the heavy and light chain fragments of the $F_v$ region via an amino acid bridge, resulting in a single chain polypeptide. Techniques for the assembly of functional $F_v$ fragments in E. coli may also be used (Skerra et al., Science 242:1038 (1988)).

The instant invention encompasses antibodies recombinantly fused or chemically conjugated (including both covalently and non-covalently conjugations) to a polypeptide. Fused or conjugated antibodies of the present invention may be used for ease in purification, see e.g., WO 93/21232; EP 439,095; Naramura et al., Immunol Lett 39:91 (1994); U.S. Pat. No. 5,474,981; Gillies et al., Proc Natl Acad Sci USA 89:1428 (1992); and Fell et al., J Immunol 146:2446 (1991). The marker amino acid sequence can be a hexa-histidine peptide, such as the tag provided in a pQE vector (QIAGEN, Inc., Chatsworth, Calif.), among others, many of which are commercially available, Gentz et al., Proc Natl Acad Sci USA 86:821 (1989). Other peptide tags useful for purification include, but are not limited to, the "HA" tag, which corresponds to an epitope derived from the influenza hemagglutinin protein (Wilson et al., Cell 37:767 (1984)) and the "flag" tag.

One can also create a single peptide chain binding molecules in which the heavy and light chain $F_v$ regions are connected. Single chain antibodies ("sc$F_v$") and the method of their construction are described in, for example, U.S. Pat. No. 4,946,778. Alternatively, $F_{ab}$ can be constructed and expressed by similar means. All of the wholly and partially human antibodies can be less immunogenic than wholly murine monoclonal antibodies, and the fragments and single chain antibodies also can be less immunogenic.

Antibodies or antibody fragments can be isolated from antibody phage libraries generated using the techniques described in McCafferty et al., Nature 348:552 (1990). Clarkson et al., Nature 352:624 (1991) and Marks et al., J Mol Biol 222:581 (1991) describe the isolation of murine and human antibodies, respectively, using phage libraries. Subsequent publications describe the production of high affinity (nM range) human antibodies by chain shuffling (Marks et al., Bio/Technology 10:779 (1992)), as well as combinatorial infection and in vivo recombination as a strategy for constructing very large phage libraries (Waterhouse et al., Nucl Acids Res 21:2265 (1993)). Thus, the techniques are viable alternatives to traditional monoclonal antibody hybridoma techniques for isolation of monoclonal antibodies.

Candidate anti-IL-4 and/or IL-13 antibodies are tested by enzyme-linked immunosorbent assay (ELISA), FACS, Western immunoblotting or other immunochemical techniques as known in the art.

To determine whether a particular antibody homolog binds to human IL-4 and/or IL-13, any conventional binding assay may be used. Useful IL-4 and IL-13 binding assays include FACS analysis, ELISA assays, Surface Plasmon Resonance (Biacore), radioimmunoassays and the like, which detect binding of antibody, and functions resulting therefrom, to human IL-4 and/or IL-13. Full-length and soluble forms of human IL-4 and IL-13 taught herein are useful in such assays. The binding of an antibody or homolog to IL-4 and/or IL-13, or to soluble fragments thereof, may conveniently be detected through the use of a second antibody specific for immunoglobulins of the species from which the antibody or homolog is derived.

To determine whether a particular antibody or homolog does or does not significantly block binding to IL-4 and/or IL-13, any suitable competition assay may be used. Useful assays include, for example, ELISA assays, FACS assays, radioimmunoassays and the like that quantify the ability of the antibody or homolog to compete with IL-4 and/or IL-13. Preferably, the ability of ligand to block binding of labeled human IL-4 and/or IL-13 to immobilized antibody or homolog is measured.

Antibodies of the instant invention may be described or specified in terms of the epitope(s) or portion(s) of IL-4 and/or IL-13 to which the antibody recognizes or specifically binds. The epitope(s) or polypeptide portion(s) may be specified as described herein, e.g., by N-terminal and C-terminal positions, by size in contiguous amino acid residues, conformational epitopes and so on.

Antibodies of the instant invention may also be described or specified in terms of cross-reactivity. Antibodies that bind IL-4 and/or IL-13 polypeptides, which have at least 95%, at least 90%, at least 85%, at least 80%, at least 75%, at least 70%, at least 65%, at least 60%, at least 55%, and at least 50% identity (as calculated using methods known in the art and described herein) to IL-4 and/or IL-13 are also included in the instant invention.

Antibodies of the instant invention also may be described or specified in terms of binding affinity to IL-4 and/or IL-13. Anti-IL-4 and/or anti-IL-13 antibodies may bind with a $K_D$ of less than about $10^{-7}$ M, less than about $10^{-6}$ M, or less than about $10^{-5}$ M. Higher binding affinities in an antibody of interest can be beneficial, such as those with an equilibrium dissociation constant or $K_D$ of from about $10^{-8}$ to about $10^{-15}$ M, from about $10^{-8}$ to about $10^{-12}$ M, from about $10^{-9}$ to about $10^{-11}$ M, or from about $10^{-8}$ to about $10^{-10}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

The instant invention also includes conjugates comprising an antibody of interest. The conjugates comprise two primary components, an antibody of interest and a second component, which may be a cell-binding agent, a cytotoxic agent and so on.

As used herein, the term "cell-binding agent" refers to an agent that specifically recognizes and binds to a molecule on the cell surface. Thus, the cell-binding agent can be a CD antigen, a pathogen antigen, such as a virus antigen, a differentiation antigen, a cancer antigen, a cell-specific antigen, a tissue-specific antigen, an Ig or Ig-like molecule and so on.

Cell-binding agents may be of any type as presently known, or that become known, and includes peptides, non-peptides, saccharides, nucleic acids, ligands, receptors and so on, or combinations thereof. The cell-binding agent may be any compound that can bind a cell, either in a specific or non-specific manner. Generally, the agent can be an antibody (especially monoclonal antibodies), lymphokines, hormones, growth factors, vitamins, nutrient-transport molecules (such as transferrin), or any other cell-binding molecule or substance.

Other examples of cell-binding agents that can be used include: polyclonal antibodies; monoclonal antibodies; and fragments of antibodies such as $F_{ab}$, $F_{ab'}$, $F_{(ab')2}$ and $F_v$ (Parham, J. Immunol. 131:2895-2902 (1983); Spring et al., J. Immunol. 113:470-478 (1974); and Nisonoff et al., Arch. Biochem. Biophys. 89: 230-244 (1960)).

The second component also can be a cytotoxic agent. The term "cytotoxic agent" as used herein refers to a substance that reduces or blocks the function, or growth, of cells and/or causes destruction of cells. Thus, the cytotoxic agent can be a taxol, a maytansinoid, such as DM1 or DM4, CC-1065 or a CC-1065 analog, a ricin, mitomycin C and so on. In some embodiments, the cytotoxic agent, as with any binding agent of a conjugate of the instant invention is covalently attached, directly or via a cleavable or non-cleavable linker, to an antibody of interest.

Examples of suitable maytansinoids include maytansinol and maytansinol analogs. Maytansinoids inhibit microtubule formation and are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Examples of suitable analogues of maytansinol having a modified aromatic ring include: (1) C-19-dechloro (U.S. Pat. No. 4,256,746) (prepared, for example, by LAH reduction of ansamytocin P2); (2) C-20-hydroxy (or C-20-demethyl)+/− C-19-dechloro (U.S. Pat. Nos. 4,361,650 and 4,307,016) (prepared, for example, by demethylation using *Streptomyces* or *Actinomyces* or dechlorination using lithium aluminum hydride (LAH)); and (3) C-20-demethoxy, C-20-acyloxy (—OCOR), +/−dechloro (U.S. Pat. No. 4,294,757) (prepared by acylation using acyl chlorides).

Examples of suitable analogues of maytansinol having modifications of other positions include: (1) C-9-SH (U.S. Pat. No. 4,424,219) (prepared by the reaction of maytansinol with $H_2S$ or $P_2S_5$); (2) C-14-alkoxymethyl (demethoxy/$CH_2OR$) (U.S. Pat. No. 4,331,598); (3) C-14-hydroxymethyl or acyloxymethyl ($CH_2OH$ or $CH_2OAc$) (U.S. Pat. No. 4,450,254) (prepared from *Nocardia*); (4) C-15-hydroxy/acyloxy (U.S. Pat. No. 4,364,866) (prepared by the conversion of maytansinol by *Streptomyces*); (5) C-15-methoxy (U.S. Pat. Nos. 4,313,946 and 4,315,929) (isolated from *Trewia nudiflora*); (6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

The cytotoxic conjugates may be prepared by in vitro methods. To link a cytotoxic agent, drug or prodrug to the antibody, commonly, a linking group is used. Suitable linking groups are known in the art and include disulfide groups, thioether groups, acid labile groups, photolabile groups, peptidase labile groups and esterase labile groups. For example, conjugates can be constructed using a disulfide exchange reaction or by forming a thioether bond between an antibody of interest and the drug or prodrug.

As discussed above, the instant invention provides isolated nucleic acid sequences encoding an antibody or functional fragment or variant thereof as disclosed herein, vector constructs comprising a nucleotide sequence encoding the IL-4 and/or IL-13-binding portion of the antibody or functional fragment thereof of the present invention, host cells comprising such a vector, and recombinant techniques for the production of the polypeptide.

The vector normally contains components known in the art and generally include, but are not limited to, one or more of the following: a signal sequence, an origin of replication, one or more marker or selection genes, sequences facilitating and/or enhancing translation, an enhancer element and so on. Thus, the expression vectors include a nucleotide sequence operably linked to such suitable transcriptional or translational regulatory nucleotide sequences such as those derived from mammalian, microbial, viral or insect genes. Examples of additional regulatory sequences include operators, mRNA ribosomal binding sites, and/or other appropriate sequences which control transcription and translation, such as initiation and termination thereof. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of that nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody or portion thereof. The signal peptide may be cleaved from the polypeptide on secretion of antibody from the cell. Examples of such secretory signals are well known and include, e.g., those described in U.S. Pat. Nos. 5,698,435; 5,698,417; and 6,204,023.

The vector may be a plasmid, a single-stranded or double-stranded viral vector, a single-stranded or double-stranded RNA or DNA phage vector, a phagemid, a cosmid or any other carrier of a transgene of interest. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells and using plural vectors carrying the various virus components necessary to produce a particle. Cell-free translation systems may also be employed to produce the protein using RNAs derived from the present DNA constructs (see, e.g., WO 86/05807 and WO 89/01036; and U.S. Pat. No. 5,122,464).

The antibodies of the present invention can be expressed from any suitable host cell. Examples of host cells useful in the instant invention include prokaryotic, yeast or higher eukaryotic cells and include but are not limited to microorganisms such as bacteria (e.g., *E. coli, B. subtilis, Enterobacter, Erwinia, Klebsiella, Proteus, Salmonella, Serratia,* and *Shigella*, as well as Bacilli, *Pseudomonas* and *Streptomyces*) transformed with recombinant bacteriophage DNA, plasmid DNA or cosmid DNA expression vectors containing the antibody coding sequences of interest; yeast (e.g., *Saccharomyces, Pichia, Actinomycetes, Kluyveromyces, Schizosaccharomyces, Candida, Trichoderma, Neurospora*, and filamentous fungi, such as *Neurospora, Penicillium, Tolypocladium* and *Aspergillus*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; or tobacco mosaic virus, TMV) or transformed with recombinant plasmid expression vectors (e.g., Ti plasmid) containing antibody coding sequences; or mammalian cell systems (e.g., COS, CHO, BHK, 293 or 3T3 cells) harboring recombinant expression constructs containing promoters derived from the genome of mammalian cells (e.g., metallothionein promoter) or from mammalian viruses (e.g., the adenovirus late promoter; or the vaccinia virus 7.5K promoter).

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids, such as pKK223-3 (Pharmacia Fine Chemicals, Uppsala, Sweden), pGEM1 (Promega Biotec, Madison, Wis.), pET (Novagen, Madison, Wis.) and the pRSET (Invitrogen, Carlsbad, Calif.) series of vectors (Studier, J Mol Biol 219:37 (1991); and Schoepfer, Gene 124:83 (1993)). Promoter sequences commonly used for recombinant prokaryotic host cell expression vectors include T7, (Rosenberg et al., Gene 56:125 (1987)), β-lactamase (penicillinase), lactose promoter system (Chang et al., Nature 275:615 (1978); and Goeddel et al., Nature 281:544 (1979)), tryptophan (trp) promoter system (Goeddel et al., Nucl Acids Res 8:4057 (1980)), and tac promoter (Sambrook et al., Molecular Cloning, A Laboratory Manual, 2nd ed., Cold Spring Harbor Laboratory (1990)).

Yeast vectors will often contain an origin of replication sequence, such as from a 2μ yeast plasmid, an autonomously replicating sequence (ARS), a promoter region, sequences for polyadenylation, sequences for transcription termination and a selectable marker gene. Suitable promoter sequences for yeast vectors include, among others, promoters for metallothionein, 3-phosphoglycerate kinase (Hitzeman et al., J Biol Chem 255:2073 (1980)) or other glycolytic enzymes (Holland et al., Biochem 17:4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other suitable vectors and promoters for use in yeast expression are further described in Fleer et al., Gene 107:285 (1991). Other suitable promoters and vectors for yeast and yeast transformation protocols are well known in the art. Yeast transformation protocols are well known. One such protocol is described by Hinnen et al., Proc Natl Acad Sci 75:1929 (1978), which selects for Trp+ transformants in a selective medium.

Any eukaryotic cell culture is workable, whether from vertebrate or invertebrate culture. Examples of invertebrate cells include plant and insect cells (Luckow et al., Bio/Technology 6:47 (1988); Miller et al., Genetic Engineering, Setlow et al., eds., vol. 8, pp. 277-9, Plenum Publishing (1986); and Maeda et al., Nature 315:592 (1985)). For example, Baculovirus systems may be used for production of heterologous proteins. In an insect system, *Autographa californica* nuclear polyhedrosis virus (AcNPV) may be used as a vector to express foreign genes. The virus grows in *Spodoptera frugiperda* cells. The antibody coding sequence may be cloned under control of an AcNPV promoter (for example the polyhedrin promoter). Other hosts that have been identified include *Aedes, Drosophila melanogaster* and *Bombyx mori*. A variety of viral strains for transfection are publicly available, e.g., the L-1 variant of AcNPV and the Bm-5 strain of *Bombyx mori* NPV. Moreover, plant cell cultures of cotton, corn, potato, soybean, petunia, tomato, and tobacco and also be utilized as hosts as known in the art.

Vertebrate cells and propagation of vertebrate cells in culture (tissue culture) can be a routine procedure, although fastidious cell lines do exist which require, for example, a specialized medium with unique factors, feeder cells and so on, see Tissue Culture, Kruse et al., eds., Academic Press (1973). Examples of useful mammal host cell lines are monkey kidney; human embryonic kidney line; baby hamster kidney cells; Chinese hamster ovary cells/-DHFR (CHO, Urlaub et al., Proc Natl Acad Sci USA 77:4216 (1980)); mouse sertoli cells; human cervical carcinoma cells (for example, HeLa); canine kidney cells; human lung cells; human liver cells; mouse mammary tumor; and NSO cells.

Host cells are transformed with vectors for antibody production and cultured in conventional nutrient medium containing growth factors, vitamins, minerals and so on, as well as inducers appropriate for the cells and vectors used. Commonly used promoter sequences and enhancer sequences are derived from polyoma virus, Adenovirus 2, Simian virus 40 (SV40) and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice and polyadenylation sites. Viral early and late promoters are particularly useful because both are easily obtained from a viral genome as a fragment which may also contain a viral origin of replication. Exemplary expression vectors for use in mammalian host cells are commercially available.

Commercially available medium such as Ham's F10, Minimal Essential Medium (MEM), RPMI-1640 and Dulbecco's Modified Eagle's Medium (DMEM) are suitable for culturing host cells. In addition, any of the media described in Ham et al., Meth Enzymol 58:44 (1979) and Barnes et al., Anal Biochem 102:255 (1980), and in U.S. Pat. Nos. 4,767, 704; 4,657,866; 4,560,655; 5,122,469; 5,712,163; or 6,048, 728 may be used as a culture medium for the host cells. Any of those media may be supplemented as necessary with hormones and/or other growth factors (such as insulin, transferrin or epidermal growth factor), salts (such as chlorides, such as sodium, calcium or magnesium chloride; and phosphates), buffers (such as HEPES), nucleotides (such as adenosine and thymidine), antibiotics, trace elements (defined as inorganic compounds usually present at final concentrations in the micromolar range) and glucose or an equivalent energy source. Any other necessary supplements may be included at appropriate concentrations, as a design choice. The culture conditions, such as temperature, pH and the like, are as known in the art appropriate for the cell and to enable the desired expression of the transgene.

The polynucleotides of interest may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio/Techniques 17:242 (1994)) and then amplifying the ligated oligonucleotides, for example, by PCR.

Alternatively, a polynucleotide encoding an antibody may be generated from nucleic acid of a cell expressing same. If a clone containing a nucleic acid encoding a particular antibody is not available, but the sequence of the antibody molecule is known, a nucleic acid encoding the immunoglobulin may be obtained from a suitable source, such as a library, which may be one specific for antibody-producing cells, such as hybridoma cells selected to express an antibody of the invention. Suitable primers can be configured for PCR amplification. Amplified nucleic acids generated by PCR may then be cloned into replicable cloning vectors using any method well known in the art.

Once the nucleotide sequence and corresponding amino acid sequence of the antibody are determined, the nucleotide sequence of the antibody may be manipulated to obtain the equivalents of interest described herein using methods known in the art for manipulating nucleotide sequences, e.g., recombinant DNA techniques, site directed mutagenesis, PCR etc. (see, for example, Sambrook et al., Molecular Cloning, A Laboratory Manual, 2nd ed., Cold Spring Harbor Laboratory (1990); and Ausubel et al., eds., Current Protocols in Molecular Biology, John Wiley & Sons (1998) to generate antibodies having a different amino acid sequence, for example, to create amino acid substitutions, deletions and/or insertions.

The amino acid sequence of the heavy and/or light chain variable domain may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The polynucleotide of interest generated by the combination of the framework regions and one or more CDRs encodes an antibody that specifically binds IL-4 and/or IL-13, or at least the ED domain thereof. For example, such methods may be used to make amino acid substitutions or deletions of one or more variable region cysteine residues participating in an intrachain disulfide bond to generate antibody molecules lacking one or more intrachain disulfide bonds.

The antibodies or antibody fragments of the invention can be used to detect IL-4 and/or IL-13, and hence cells expressing IL-4 and/or IL-13, in a biological sample in vitro or in vivo. In one embodiment, the anti-IL-4 and/or IL-13 antibody of the invention is used to determine the presence and the level of IL-4 and/or IL-13 in a tissue or in cells derived from the tissue. The levels of IL-4 and/or IL-13 in the tissue or biopsy can be determined, for example, in an immunoassay with the antibodies or antibody fragments of the invention. The tissue or biopsy thereof can be frozen or fixed. The same or other methods can be used to determine other properties of IL-4 and/or IL-13, such as the level thereof, cellular localization, mRNA levels, mutations thereof and so on.

The above-described method can be used, for example, to diagnose a cancer in a subject known to be or suspected to have a cancer, wherein the level of IL-4 and/or IL-13 measured in said patient is compared with that of a normal reference subject or standard. The assay of interest also can be used to diagnose arthritis or other autoimmune diseases characterized by B cell infiltration and concentration, along with development of differentiated lymphoid tissue.

The instant invention further provides for monoclonal antibodies, humanized antibodies and epitope-binding fragments thereof that are further labeled for use in research or diagnostic applications. In some embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer, arthritis, autoimmune diseases or other IL-4 and/or IL-13 mediated disease, and the distribution of the label within the body of the subject is measured or monitored.

The antibody and fragments thereof of the instant invention may be used as affinity purification agents. In that process, the antibodies are immobilized on a solid phase, such as a dextran or agarose resin or filter paper, using methods known in the art. The immobilized antibody is contacted with a sample containing IL-4 and/or IL-13 or cells carrying same to be purified, and thereafter the support is washed with a suitable solvent that will remove substantially all the material in the sample except the IL-4 and/or IL-13 or cell to be purified, which is bound to the immobilized antibody of interest. Finally, the support is washed with another suitable solvent, such as glycine buffer, pH 5.0 that will release the IL-4 and/or IL-13 or cell from the antibody of interest.

For diagnostic applications, the antibody of interest typically will be labeled with a detectable moiety. Numerous labels are available which can be generally grouped into the following categories: (a) radioisotopes, such as $^{36}S$, $^{14}C$, $^{12}I$, $^{3}H$ and $^{131}I$ (The antibody can be labeled with the radioisotope using a techniques described in Current Protocols in Immunology, vol. 12, Coligen et al., ed., Wiley-Interscience, New York (1991), for example, and radioactivity can be measured using scintillation counting); (b) fluorescent labels, such as rare earth chelates (europium chelates), fluorescein and its derivatives, rhodamine and its derivatives, dansyl, lissamine, phycoerythrin and Texas Red, the fluorescent labels can be conjugated to the antibody using a technique disclosed in Current Protocols in Immunology, supra, for example, where fluorescence can be quantified using a fluorimeter; and (c) various enzyme substrate labels are available (U.S. Pat. No. 4,275,149 provides a review), the enzyme generally catalyzes a chemical alteration of the chromogenic substrate which can be measured using various techniques, for example, the enzyme may catalyze a color change in a substrate, which can be measured spectrophotometrically, or the enzyme may alter the fluorescence or chemiluminescence of the substrate. Techniques for quantifying a change in fluorescence are known, for example, using a luminometer, or the label donates energy to a fluorescent acceptor. Examples of enzymatic labels include luciferases (e.g., firefly luciferase and bacterial luciferase; U.S. Pat. No. 4,737,456), luciferin, 2,3-dihydrophthalazindiones, malate dehydrogenase, urease, peroxidase, such as horseradish peroxidase (HRPO), alkaline phosphatase, 3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase and the like. Techniques for conjugating enzymes to antibodies are described in O'Sullivan et al., Meth Enz, ed. Langone & Van Vunakis, Academic Press, New York, 73 (1981).

When such labels are used, suitable substrates are available, such as: (i) for horseradish peroxidase with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) for alkaline phosphatase (AP) with p-nitrophenyl phosphate as the chromogenic substrate; and (iii) β-D-galactosidase (β-D-Gal) with a chromogenic substrate (e.g., p-nitrophenyl-β-D-galactosidase) or a fluorogenic substrate such as 4-methylumbelliferyl-β-D-galactosidase.

Other enzyme-substrate combinations are available to those skilled in the art. For a general review, see U.S. Pat. Nos. 4,275,149 and 4,318,980.

Sometimes, the label is indirectly conjugated with the antibody. For example, the antibody can be conjugated with biotin and any of the reporters mentioned above can be conjugated with avidin, or vice versa. Biotin binds selectively to avidin and thus, the label can be conjugated with the antibody in that indirect manner. Alternatively, to achieve indirect conjugation of the label, the antibody is conjugated with a small hapten (e.g., digoxin) and one of the different types of labels or reporters mentioned above is conjugated with an anti-digoxin antibody. Thus, indirect conjugation of the label with the antibody or mutein can be achieved using a second antibody.

In another embodiment of the invention, the antibody need not be labeled, and the presence thereof can be detected using a labeled antibody which binds to the antibody, another form of a second antibody.

The antibodies of the present invention may be employed in any known assay method, such as competitive binding assays, direct and indirect sandwich assays, and immunoprecipitation assays. Zola, Monoclonal Antibodies: A Manual of Techniques (CRC Press, Inc. 1987).

Competitive binding assays rely on the ability of a labeled standard to compete with the test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, determinant or epitope, of the target to be detected. In a sandwich assay, the test sample to be analyzed is bound by a first antibody which is immobilized directly or indirectly on a solid support, and thereafter a second antibody directly or indirectly labeled binds to the bound test sample, thus forming an insoluble three-part complex, see e.g., U.S. Pat. No. 4,376,110. The second antibody may itself be labeled with a detectable moiety (direct sandwich assays) or may be measured using an anti-immunoglobulin antibody or other suitable member of the binding pair (antibody/antigen, receptor/ligand, enzyme/substrate, for example) that is labeled with a detectable moiety (indirect sandwich assay).

For example, one type of sandwich assay is an ELISA assay, in which case the detectable moiety is an enzyme.

The instant invention also includes kits, e.g., comprising an antibody, fragment thereof, homolog, derivative thereof and so on, such as a labeled or cytotoxic conjugate, and instructions for the use of the antibody, conjugate for killing particular cell types and so on. The instructions may include directions for using the antibody, conjugate and so on in vitro, in vivo or ex vivo. The antibody can be in liquid form or as a solid, generally lyophilized. The kit can contain suitable other reagents, such as a buffer, a reconstituting solution and other necessary ingredients for the intended use. A packaged combination of reagents in predetermined amounts with instructions for use thereof, such as for a therapeutic use of for performing a diagnostic assay is contemplated. Where the antibody is labeled, such as with an enzyme, the kit can include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied to provide for concentrates of a solution of a reagent, which provides user flexibility, economy of space, economy of reagents and so on. The reagents may be provided as dry powders, usually lyophilized, including excipients, which on dissolution provide a reagent solution having the appropriate concentration.

The antibodies of the present invention may be used to treat a mammal. In one embodiment, the antibody or equivalent of interest is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody, or may be used to study toxicity of the antibody of interest. In each of those embodiments, dose escalation studies may be performed in the mammal.

An antibody, with or without a second component, such as a therapeutic moiety conjugated to same, administered alone or in combination with cytotoxic factor(s) can be used as a therapeutic. The present invention is directed to antibody-based therapies which involve administering antibodies of the invention to an animal, a mammal, or a human, for treating a IL-4 and/or IL-13 mediated disease, disorder or condition.

The term "treatment" as used in the present invention refers to both therapeutic treatment and prophylactic or preventative measures. It refers to preventing, curing, reversing, attenuating, alleviating, minimizing, suppressing or halting the deleterious effects of a disease state, disease progression, disease causative agent (e.g., bacteria or viruses) or other abnormal condition.

Thus the invention also includes polyvalent antibodies, including bispecific anti-IL-4/IL-13 antibodies, having attached thereto diagnostically or therapeutically functional effector molecules, atoms or other species. For example, the antibody may have a radioactive diagnostic label or radioactive cytotoxic atom or metal or cytotoxic species, e.g. ricin chain, attached thereto for in vivo diagnosis or therapy of cancer.

Moreover, the antibodies according to the invention may be used in immunoassays, in purification methods and in other methods in which immunoglobulins or fragments thereof are used. Such uses are well-known in the art.

Accordingly, the invention also provides compositions comprising the anti-IL-13 and/or anti-IL-4 antibodies or fragments thereof according to the invention, conveniently in combination with a pharmaceutically acceptable carrier, diluent or excipient which are conventional in the art.

The term "pharmaceutical composition" as used in the present invention refers to formulations of various preparations. The formulations containing therapeutically effective amounts of the polyvalent antibodies are sterile liquid solutions, liquid suspensions or lyophilized versions and optionally contain stabilizers or excipients.

The term "disorder" as used in the present invention refers to any condition that would benefit from treatment with the antibody of the present invention. This includes chronic and acute disorders or diseases including those pathological conditions which predispose the mammal, and in particular humans, to the disorder in question. Non-limiting examples of disorders to be treated herein include cancers, inflammation, autoimmune diseases, infections, cardiovascular diseases, respiratory diseases, neurological diseases and metabolic diseases.

The antibodies of the present invention may be used to treat, suppress or prevent disease, such as an allergic disease, a Th2-mediated disease, IL-13-mediated disease, IL-4-mediated disease, and/or IL-4/IL-13-mediated disease. Examples of such diseases include, Hodgkin's disease, asthma, allergic asthma, atopic dermatitis, atopic allergy, ulcerative colitis, scleroderma, allergic rhinitis, COPD3 idiopathic pulmonary fibrosis, chronic graft rejection, bleomycin-induced pulmonary fibrosis, radiation-induced pulmonary fibrosis, pulmonary granuloma, progressive systemic sclerosis, schistosomiasis, hepatic fibrosis, renal cancer, Burkitt lymphoma, Hodgkins disease, non-Hodgkins disease, Sezary syndrome, asthma, septic arthritis, dermatitis herpetiformis, chronic idiopathic urticaria, ulcerative colitis, scleroderma, hypertrophic scarring, Whipple's Disease, benign prostate hyperplasia, a lung disorder in which IL-4 receptor plays a role, condition in which IL-4 receptor-mediated epithelial barrier disruption plays a role, a disorder of the digestive system in which IL-4 receptor plays a role, an allergic reaction to a medication, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, cystic fibrosis, allergic bronchopulmonary mycosis, chronic obstructive pulmonary disease, bleornycin-induced pneumopathy and fibrosis, pulmonary alveolar proteinosis, adull respiratory distress syndrome, sarcoidosis, hyper IgE syndrome, idiopathic hypcrcosinophil syndrome, an autoimmunc blistering disease, pemphigus vulgaris, bullous pemphigoid, myasthenia gravis, chronic fatigue syndrome, nephrosis).

The term "allergic disease" refers to a pathological condition in which a patient is hypersensitized to and mounts an immunologic reaction against a substance that is normally nonimmunogenic. Allergic disease is generally characterized by activation of mast cells by IgE resulting in an inflammatory response (e.g., local response, systemic response) that can result in symptoms as benign as a runny nose, to life-threatening anaphylactic shock and death. Examples of allergic disease include, but are not limited to, allergic rhinitis (e.g., hay fever), asthma (e.g., allergic asthma), allergic dermatitis (e.g., eczema), contact dermatitis, food allergy and urticaria (hives).

As used herein "Th2-mediated disease" refers to a disease in which pathology is produced (in whole or in part) by an immune response (Th2-type immune response) that is regulated by $CD4^+$ Th2 T lymphocytes, which characteristically produce IL-4, IL-5, IL-9 and IL-13. A Th2-type immune response is associated with the production of certain cytokines (e.g., IL-4, IL-13) and of certain classes of antibodies (e.g., IgE), and is associate with humoral immunity. Th2-mediated diseases are characterized by the presence of elevated levels of Th2 cytokines (e.g., IL-4, IL-13) and/or certain classes of antibodies (e.g., IgE) and include, for example, allergic disease (e.g., allergic rhinitis, atopic dermatitis, asthma (e.g., atopic asthma), allergic airways disease (AAD), anaphylactic shock, conjunctivitis), autoimmune disorders associated with elevated levels of IL-4 and/or IL-13 (e.g., rheumatoid arthritis, host-versus-graft disease, renal disease (e.g., nephritic syndrome, lupus nephritis)), and infections associated with elevated levels of IL-4 and/or IL-13 (e.g., viral, parasitic, fungal (e.g., *C. albicans*) infection). Certain cancers are associated with elevated levels of IL-4 and/or IL-13 or associated with IL-4-induced and/or IL-13-induced cancer cell proliferation (e.g., B cell lymphoma, T cell lymphoma, multiple myeloma, head and neck cancer, breast cancer and ovarian cancer). These cancers can be treated, suppressed or prevented using the li gaud of the invention.

The term "cancer" as used in the present invention refers to or describes the physiological condition in mammals, in particular humans, which is typically characterized by unregulated cell growth. Examples of cancer include but are not limited to, carcinoma, lymphoma, blastoma, sarcoma, and leukemia.

The term "autoimmune disease" as used in the present invention refers to a non-malignant disease or disorder arising from and directed against an individual's own tissues. Examples of autoimmune diseases or disorders include, but are not limited to, inflammatory responses such as inflammatory skin diseases including psoriasis and dermatitis; allergic conditions such as eczema and asthma; other conditions involving infiltration of T cells and chronic inflammatory responses; atherosclerosis; diabetes mellitus (e. g. Type I diabetes mellitus or insulin dependent diabetes mellitis); multiple sclerosis and central nervous system (CNS) inflammatory disorder.

The antibodies of the present invention may be used as separately administered compositions or in conjunction with other agents. The antibodies can be used in combination therapy with existing IL-13 therapeutics (e.g., existing IL-13 agents such as anti-IL-13Rα1, IL-4/13 Trap, anti-IL-13) plus anti-IL-4 antibody and existing IL-4 agents (for example, anti-IL-4R, IL-4 Mutein, IL-4/13 Trap) plus anti-IL-13 antibody and IL-4 antibodies (for example, WO05/0076990 (CAT), WO03/092610 (Regeneron), WO00/64944 (Genetic Inst.) and WO2005/062967 (Tanox)).

The antibodies of the present invention may be administered and/or formulated together with one or more additional therapeutic or active agents. When a ligand is administered with an additional therapeutic agent, the ligand can be administered before, simultaneously with or subsequent to administration of the additional agent. Generally, the ligand and additional agent are administered in a manner that provides an overlap of therapeutic effect. Additional agents that can be administered or formulated with the ligand of the invention include, for example, various immunotherapeutic dings?, such as cylcosporine, methotrexate, adriamycin or cisplatimun, antibiotics, antimycotics, anti-viral agents and immunotoxins. For example, when the antagonist is administered to prevent, suppress or treat lung inflammation or a respiratory disease (e.g., asthma), it can be administered in conjuction with phosphodiesterase inhibitors (e.g., inhibitors of phosphodiesterase 4), bronchodilators (e.g., P2-agonists, anticholinergerics, theophylline), short-acting beta-agonists (e.g., albuterol, salbuiamol, bambuterol, fenoter[sigma]1, isoetherine, isoproterenol, leva[iota]buterol, metaproterenol, pirbuterol, terbutaline and tornlate), long-acting beta-agonists (e.g., formoterol and salmeterol), short acting anticholinergics (e.g., ipratropium bromide and oxitropium bromide), long-acting anticholinergics (e.g., tiotropium), theophylline (e.g. short acting formulation, long acting formulation), inhaled steroids (e.g., beclomethasone, beclometasone, budesonide, flunisolide, fluticasone propionate and triamcinolone), oral steroids (e.g., methylprcdnisolonc, prcdnisolonc, prednisolon and prednisonc), combined short-acting beta-agonists with anticholinergics (e.g., albuterol/salbutamol/ipratopium, and fenoterol/ipratopium), combined long-acting beta-agonists with inhaled steroids (e.g., salmeterol/fluticasone, and formolerol/budesonide) and mucolytic agents (e.g., erdosteine, acetylcysteine, bromheksin, carbocyslcine, guiafencsin and iodinated glycerol Other suitable co-therapeutic agents that can be administered with antibody of the present invention to prevent, suppress or treat asthma (e.g., allergic asthma), include a corticosteroid (e.g., beclomethasone, budesonide, fluticasone), cromoglycate, nedocromil, beta-agonist (e.g., salbutamol, terbutaline, bambuterol, fenoterol, reproterol, tolubuterol, salmeterol, fomtero), zafirlukast, salmeterol, prednisone, prednisolone, theophylline, zileutron, montelukast, and leukotriene modifiers. The ligands of the invention can be coadministered with a variety of co-therapeutic agents suitable for treating diseases (e.g., a Th-2 mediated disease, YL-A-mediatcd disease, IL-13 mediated disease, IL-4 mediated disease and cancer), including cytokines, analgesics/antipyretics, antiemetics, and chemotherapeutics.

Antibodies of the invention may be provided in pharmaceutically acceptable compositions as known in the art or as described herein. The term "physiologically acceptable," "pharmacologically acceptable" and so on mean approved by a regulatory agency of the Federal or a state government or listed in the U.S. Pharmacopeia or other generally recognized pharmacopeia for use in animals and more particularly in humans.

The anti-IL-4, anti-IL-13 and bispecific anti-IL-4/IL-13 antibodies may be administered to a mammal and in particular humans, in any acceptable manner. Methods of introduction include, but are not limited to, parenteral, subcutaneous, intraperitoneal, intrapulmonary, intranasal, epidural, inhalation and oral routes, and if desired for immunosuppressive treatment, intralesional administration. Parenteral infusions include intramuscular, intradermal, intravenous, intraarterial or intraperitoneal administration. The antibodies or compositions may be administered by any convenient route, for example, by infusion or bolus injection, by absorption through epithelial or mucocutaneous linings (e.g., oral mucosa, rectal and intestinal mucosa etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir. In addition, the antibody is suitably administered by pulse infusion, particularly with declining doses of the antibody. Preferably the dosing is given by injection, preferably intravenous or subcutaneous injections, depending, in part, on whether the administration is brief or chronic.

Various other delivery systems are known and can be used to administer an antibody of the present invention, including, e.g., encapsulation in liposomes, microparticles, microcapsules (see Langer, Science 249:1527 (1990): Treat et al., in Liposomes in the Therapy of Infectious Disease and Cancer, Lopez-Berestein et al., eds., p. 353-365 (1989); and Lopez-Berestein, ibid., p. 317-327) and recombinant cells capable of expressing the compound; receptor-mediated endocytosis (see, e.g., Wu et al., J Biol Chem 262:4429 (1987)); construction of a nucleic acid as part of a retroviral or other vector etc.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, A. Osal, Ed. (1980).

Pulmonary administration can also be employed, e.g., by use of an inhaler or nebulizer, and formulation with an aerosolizing agent. The antibody may also be administered into the lungs of a patient in the form of a dry powder composition, see e.g., U.S. Pat. No. 6,514,496.

In a specific embodiment, it may be desirable to administer the therapeutic antibodies or compositions of the invention locally to the area in need of treatment; that may be achieved by, for example, and not by way of limitation, local infusion, topical application, by injection, by means of a catheter, by means of a suppository or by means of an implant, said implant being of a porous, non-porous or gelatinous material, including membranes, such as sialastic membranes or fibers. Preferably, when administering an antibody of the invention, care is taken to use materials to which the protein does not absorb or adsorb.

In yet another embodiment, the antibody can be delivered in a controlled release system. In one embodiment, a pump may be used (see Langer, Science 249:1527 (1990); Sefton, CRC Crit Ref Biomed Eng 14:201 (1987); Buchwald et al., Surgery 88:507 (1980); and Saudek et al., N Engl J Med 321:574 (1989)). In another embodiment, polymeric materials can be used (see Medical Applications of Controlled Release, Langer et al., eds., CRC Press (1974); Controlled Drug Bioavailability, Drug Product Design and Performance, Smolen et al., eds., Wiley (1984); Ranger et al., J Macromol Sci Rev Macromol Chem 23:61 (1983); see also Levy et al., Science 228:190 (1985); During et al., Ann Neurol 25:351 (1989); and Howard et al., J Neurosurg 71:105 (1989)). In yet another embodiment, a controlled release system can be placed in proximity of the therapeutic target.

Therapeutic formulations of the polypeptide or antibody may be prepared for storage as lyophilized formulations or aqueous solutions by mixing the polypeptide having the desired degree of purity with optional "pharmaceutically acceptable" carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5% or 1%, (by dry weight) of contaminating protein. When the antibody is recombinantly produced, it is also preferably substantially free of culture medium, i.e., culture medium represents less than about 20%, 10%, 5%, 2.5% or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 30%, 20%, 10%, 5% or 1% (by dry weight) of chemical precursors or compounds other than antibody of interest. In a preferred embodiment of the present invention, antibodies are isolated or purified.

As used herein, the phrase "low to undetectable levels of aggregation" refers to samples containing no more than 5%, no more than 4%, no more than 3%, no more than 2%, no more than 1% and often no more than 0.5% aggregation, by weight protein, as measured by, for example, high performance size exclusion chromatography (HPSEC).

As used herein, the term "low to undetectable levels of fragmentation" refers to samples containing equal to or more than 80%, 85%, 90%, 95%, 98% or 99%, of the total protein, for example, in a single peak, as determined by HPSEC, or in two (2) peaks (heavy chain and light chain) by, for example, reduced capillary gel electrophoresis (rCGE) and containing no other single peaks having more than 5%, more than 4%, more than 3%, more than 2%, more than 1% or more than 0.5% of the total protein, each. The rCGE as used herein refers to capillary gel electrophoresis under reducing conditions sufficient to reduce disulfide bonds in an antibody or antibody-type or derived molecule.

As used herein, the terms "stability" and "stable" in the context of a liquid formulation comprising a IL-4 and/or IL-13 antibody or binding fragment thereof refer to the resistance of the antibody or antigen-binding fragment thereof in the formulation to thermal and chemical unfolding, aggregation, degradation or fragmentation under given manufacture, preparation, transportation and storage conditions. The "stable" formulations of the invention retain biological activity equal to or more than 80%, 85%, 90%, 95%, 98%, 99% or 99.5% under given manufacture, preparation, transportation and storage conditions. The stability of said antibody preparation can be assessed by degrees of aggregation, degradation or fragmentation by methods known to those skilled in the art, including, but not limited to, rCGE, sodium dodecyl sulfate polyacrylamide gel electrophoresis (SDS-PAGE) and HPSEC, compared to a reference.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. The compositions can take the form of solutions, suspensions, emulsion, tablets, pills, capsules, powders, sustained-release formulations, depots and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate etc. Examples of suitable carriers are described in "Remington's Pharmaceutical Sciences," Martin. Such compositions will contain an effective amount of the antibody, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid-monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts such as Tris, HEPES and other such known buffers can be used.

Preservatives may be added to retard microbial growth, and may be added in amounts ranging from 0.2/o %-1% (w/v). Suitable preservatives for use with the present invention include phenol, benzyl alcohol, m-cresol, methyl paraben, propyl paraben, octadecyldimethylbenzyl ammonium chloride, benzyaconium halides (e.g., chloride, bromide and iodide), hexamethonium chloride, alkyl parabens such as methyl or propyl paraben, catechol, resorcinol, cyclohexanol and 3-pentanol.

Isotonicifiers are present to ensure physiological isotonicity of liquid compositions of the instant invention and include polyhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc., organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose, glucose; disaccharides, such as lactose, maltose and sucrose; trisaccharides such as raffinose; polysaccharides such as dextran and so on. Stabilizers are present in the range from 0.1 to 10,000 w/w per part of active protein.

Additional miscellaneous excipients include bulking agents, (e.g., starch), chelating agents (e.g., EDTA), antioxidants (e.g., ascorbic acid, methionine or vitamin E) and cosolvents.

The formulation herein also may contain more than one active compound as necessary for the particular indication being treated, preferably those with complementary activities that do not adversely impact each other. For example, it may be desirable to further provide an immunosuppressive agent. Such molecules suitably are present in combination in amounts that are effective for the purpose intended.

As used herein, the term "surfactant" refers to organic substances having amphipathic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and nonionic surfactants. Surfactants often are used as wetting, emulsifying, solubilizing and dispersing agents for various pharmaceutical compositions and preparations of biological materials.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

As used herein, the term, "inorganic salt," refers to any compound, containing no carbon that result from replacement of part or all of the acid hydrogen or an acid by a metal or group acting like a metal, and often are used as a tonicity adjusting compound in pharmaceutical compositions and preparations of biological materials. The most common inorganic salts are NaCl, KCl, $NaH_2PO_4$ etc.

The instant invention encompasses liquid formulations having stability at temperatures found in a commercial refrigerator and freezer found in the office of a physician or laboratory, such as from about −20° C. to about 5° C., said stability assessed, for example, by high performance size exclusion chromatography (HPSEC), for storage purposes, such as for about 60 days, for about 120 days, for about 180 days, for about a year, for about 2 years or more. The liquid formulations of the present invention also exhibit stability, as assessed, for example, by HSPEC, at room temperatures, for a at least a few hours, such as one hour, two hours or about three hours prior to use.

The term "small molecule" and analogous terms include, but are not limited to, peptides, peptidomimetics, amino acids, amino acid analogues, polynucleotides, polynucleotide analogues, nucleotides, nucleotide analogues, organic or inorganic compounds (i.e., including heterorganic and/or ganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Thus, in the case of cancer, the antibodies of the invention may be administered alone or in combination with other types of cancer treatments, including conventional chemotherapeutic agents (paclitaxel, carboplatin, cisplatin and doxorubicin), anti-EGFR agents (gefitinib, erlotinib and cetuximab), anti-angiogenesis agents (bevacizumab and sunitinib), as well as immunomodulating agents, such as interferon-α and thalidomide.

As used herein, the terms "therapeutic agent" and "therapeutic agents" refer to any agent(s) which can be used in the treatment, management or amelioration of a disease, disorder, malady and the like associated with aberrant IL-4 and/or IL-13 metabolism and activity.

In addition, the antibodies of the instant invention may be conjugated to various effector molecules such as heterologous polypeptides, drugs, radionucleotides or toxins, see, e.g., WO 92/08495; WO 91/14438; WO 89/12624; U.S. Pat. No. 5,314,995; and EPO 396,387. An antibody or fragment thereof may be conjugated to a therapeutic moiety such as a cytotoxin (e.g., a cytostatic or cytocidal agent), a therapeutic agent or a radioactive metal ion (e.g., α emitters, such as, for example, $^{213}$Bi). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracindione, mitoxantrone, mithramycin, actinomycin D, 1-dehydrotestosterone, glucocorticoids, procaine, tetracaine, lidocaine, propranolol and puromycin and analogs or homologues thereof. Therapeutic agents include, but are not limited to, antimetabolites (e.g., methotrexate, 6-mercaptopurine, 6-thioguanine, cytarabine, 5-fluorouracil and decarbazine), alkylating agents (e.g., mechlorethamine, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin, daunomycin and doxorubicin), antibiotics (e.g., dactinomycin, actinomycin, bleomycin, mithramycin and anthramycin (AMC)), and anti-mitotic agents (e.g., vincristine and vinblastine).

Techniques for conjugating such a therapeutic moiety to antibodies are well known, see, e.g., Arnon et al., in Monoclonal Antibodies and Cancer Therapy, Reisfeld et al. (eds.), p. 243-56 Alan R. Liss (1985); Hellstrom et al., in Controlled Drug Delivery, 2nd ed., Robinson et al., eds., p. 623-53, Marcel Dekker (1987); Thorpe, in Monoclonal Antibodies '84: Biological And Clinical Applications, Pinchera et al., eds., p. 475-506 (1985); Monoclonal Antibodies For Cancer Detection and Therapy. Baldwin et al., eds., p. 303-16, Academic Press (1985); and Thorpe, et al., Immunol Rev 62:119 (1982). Alternatively, an antibody can be conjugated to a second antibody to form an antibody heteroconjugate, such as a bifunctional antibody, see, e.g., U.S. Pat. No. 4,676,980.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM 1 (WO 97/33899), AIM II (WO 97/34911), Fas ligand (Takahashi et al., Int Immunol, 6:1567 (1994)), VEGF (WO 99/23105); a thrombotic agent; an anti-angiogenic agent, e.g., angiostatin or endostatin; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (GCSF) or other growth factors.

The formulations to be used for in vivo administration must be sterile. That can be accomplished, for example, by filtration through sterile filtration membranes. For example, the liquid formulations of the present invention may be sterilized by filtration using a 0.2 μm or a 0.22 μm filter.

Sustained-release preparations may be prepared. Suitable examples of sustained-release preparations include semipermeable matrices of solid hydrophobic polymers containing the antibody, which matrices are in the form of shaped articles, e.g., films or matrices. Examples of sustained-release matrices include polyesters, hydrogels (for example, poly(2-hydroxyethylmethacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers (such as injectable microspheres composed of lactic acid-glycolic acid copolymer) and poly-D-(−)-3-hydroxybutyric acid. While polymers such as ethylene-vinyl acetate and lactic acid-glycolic acid enable release of molecules for over 100 days, certain hydrogels release proteins for shorter time periods. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, amino acid substitution and developing specific polymer matrix compositions.

The antibody or variant composition will be formulated, dosed and administered in a manner consistent with good medical practice. Factors for consideration in this context include the particular disorder being treated, the particular mammal or human being treated, the clinical condition of the individual patient, the cause of the disorder, the site of delivery of the agent, the method of administration, the scheduling of administration, and other factors known to medical practitioners. The "therapeutically effective amount" of the antibody or variant to be administered will be governed by such considerations, and can be the minimum amount necessary to prevent, ameliorate or treat a IL-4 and/or IL-13 mediated disease, condition or disorder.

The antibody or variant optionally is formulated with one or more agents currently used to prevent or treat the disorder in question. The effective amount of such other agents depends on the amount of antibody present in the formulation, the type of disorder or treatment and other factors discussed above. These are generally used in the same dosages and with administration routes as used hereinbefore or about from 1 to 99% of the heretofore employed dosages.

As used herein, the term "effective amount" refers to the amount of a therapy (e.g., a prophylactic or therapeutic agent), which is sufficient to reduce the severity and/or duration of a IL-4 and/or IL-13 mediated disease, ameliorate one or more symptoms thereof, prevent the advancement of a IL-4 and/or IL-13 mediated disease or cause regression of a disease, or which is sufficient to result in the prevention of the development, recurrence, onset, or progression of a IL-4 and/or IL-13 mediated disease or one or more symptoms thereof, or enhance or improve the prophylactic and/or therapeutic effect(s) of another therapy (e.g., another therapeutic agent) useful for treating a IL-4 and/or IL-13 mediated disease.

The amount of therapeutic antibody or fragment thereof which will be effective in the use or treatment of a particular disorder or condition will depend on the nature of the disorder or condition, and can be determined by standard clinical techniques. Where possible, a dose-response curve and the pharmaceutical compositions of the invention can be first derived in vitro. If a suitable animal model system is available, again a dose-response curve can be obtained and used to extrapolate a suitable human dose practicing methods known in the art. However, based on common knowledge of the art, a pharmaceutical composition effective in promoting a diminution of an inflammatory effect, for example, may provide a local therapeutic agent concentration of between about 5 and 20 ng/ml, and, preferably, between about 10 and 20 ng/ml.

In a preferred embodiment, an aqueous solution of therapeutic polypeptide, antibody or fragment thereof can be administered by subcutaneous injection. Each dose may range from about 0.5 mg to about 50 mg per kilogram of body weight, or more preferably, from about 3 mg to about 30 mg per kilogram body weight. The dosage can be ascertained empirically for the particular disease, patient population, mode of administration and so on, practicing pharmaceutical methods known in the art.

The dosing schedule for subcutaneous administration may vary from once a week to daily depending on a number of clinical factors, including the type of disease, severity of disease and the sensitivity of the subject to the therapeutic agent.

The instant invention provides methods for preparing liquid formulations of the antibody or IL-4 and/or IL-13 binding fragment thereof, said methods comprising concentrating a fraction of purified antibody to a final concentration of about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 200 mg/ml, about 250 mg/ml, about 300 mg/ml or more using, for example, a semi-permeable membrane with an appropriate molecular weight (mw) cutoff (e.g., 30 kD cutoff for $F_{(ab')2}$ fragments thereof; and 10 kD cutoff for $F_{ab}$ fragments).

In addition, the present invention also encompasses stable liquid formulations of the products of interest that have improved half-life in vivo. Thus, the antibody of interest has a half-life in a subject, preferably a human, of greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, greater than 5 months or more.

To prolong the serum circulation of an antibody in vivo, various techniques can be used. For example, inert polymer molecules, such as high molecular weight polyethylene glycol (PEG), can be attached to an antibody with or without a multifunctional linker either through site-specific conjugation of the PEG to the N-terminus or to the C-terminus of the antibody or via ε amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion exchange chromatography. PEG-derivatized antibodies can be tested for binding activity as well as for in vivo efficacy using methods known to those of skilled in the art, for example, by immunoassays described herein.

An antibody having an increased half-life in vivo can also be generated by introducing one or more amino acid modifications (i.e., substitutions, insertions or deletions) into an IgG constant domain, or $F_cR$ binding fragment thereof (such as an $F_c$ or hinge $F_c$ domain fragment), see, e.g., WO 98/23289; WO 97/34631; and U.S. Pat. No. 6,277,375.

Further, an antibody can be conjugated to albumin to make an antibody more stable in vivo or have a longer half life in vivo. The techniques are known in the art, see e.g., WO 93/15199, WO 93/15200 and WO 01/77137; and EPO 413, 622. The antibody also can be modified, for example, by glycosylation, acetylation, phosphorylation, amidation, derivatization by known protecting/blocking groups, proteolytic cleavage, linkage to a cellular ligand or other protein and so on.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine or other "caine" anesthetic to ease pain at the site of the injection. Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

The invention also provides that a liquid formulation of the present invention is packaged in a sealed container such as an ampule or sachet indicating the quantity of the product of interest. The liquid formulations of the instant invention can be in a scaled container indicating the quantity and concentration of the antibody or antibody fragment. The liquid formulation of the instant invention can be supplied in a sealed container with at least 15 mg/ml, 20 mg/ml, 30 mg/ml, 40 mg/ml, 50 mg/ml. 60 mg/ml, 70 mg/ml, 80 mg/ml, 90 mg/ml, 100 mg/ml, 150 mg/ml, 200 mg/ml, 250 mg/ml, or 300 mg/ml of IL-4 and/or IL-13 antibody in a quantity of 1 ml, 2 ml, 3 ml, 4 ml, 5 ml, 6 ml, 7 ml, 8 ml, 9 ml, 10 ml, 15 ml or 20 ml, for example.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for diagnosing, preventing or treating a IL-4 and/or IL-13 mediated condition or disease and may have a sterile access port (for example, the container may be an intravenous solution bag or a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

The invention now will be exemplified for the benefit of the artisan by the following non-limiting examples that depict some of the embodiments by and in which the instant invention can be practiced.

EXAMPLES

Example 1: Sequencing of the Fv Domain of Mouse Anti-Human IL-13 Monoclonal Antibody Clone B-B13

The reagent used in the method below was mouse anti-IL-13 monoclonal antibody clone B-B13 purchased from Cell Sciences, Inc. (Canton, Mass., USA). Cell Sciences is the US distributor of Diaclone (Besancon, France), which manufactured the antibody B-B13.

The amino acid sequence of anti-IL-13 monoclonal antibody Clone B-B13 was determined by a combination of Edman N-terminal sequencing and mass spectrometric analysis. The antibody was subjected to the following different approaches in order to generate polypeptide or peptide fragments, and these were fractionated by different approaches in order to prepare samples that were subsequently subjected to Edman N-terminal sequencing, and Liquid Chromatography/Mass Spectrometry/Mass Spectrometry (LC-MS/MS) analysis with associated protein sequence database peptide matching.

SDS-Page of the antibody, either untreated or treated with pyrogluamino peptidase, to separate the heavy and light chains, followed by blotting to polyvinylidene fluoride (PVDF) membrane and Edman N-terminal sequencing of the bands.

Limited partial proteolysis with specific proteases of the antibody followed by SDS-Page and blotting to PVDF membrane and Edman N-terminal sequencing of the bands.

Limited partial chemical cleavage of the whole antibody, or heavy and light chain SDS-Page gel bands, followed by SDS-Page and blotting to PVDF membrane and Edman N-terminal sequencing of bands.

Proteolysis of the whole antibody or heavy and light chain SDS-Page gel bands with specific proteases and LC/MS/MS analysis.

Proteolysis of heavy and light chain SDS-Page gel bands with specific proteases followed by reverse phase high pressure liquid chromatography fractionation (rp-hplc), and subsequent Edman N-terminal sequencing and LC/MS/MS analysis of fractions.

Limited proteolysis of the antibody with the protease papain, fractionation of the Fd (VH-CH1 fragment of the antibody heavy chain) gel band by SDS-Page, proteolysis with specific proteases, reverse phase high performance liquid chromatograph (rp-hplc), and subsequent Edman N-terminal sequencing and LC/MS/MS analysis of fractions.

Example 2: Sequencing of the Fv Domain of Mouse Anti-Human IL-4 Monoclonal Antibody Clone 8D4-8

The reagent mouse anti-IL-4 monoclonal antibody clone 8D4-8 was purchased from Biozol diagnostica Vertrieb GmbH (Eching, Germany). Biozol is the German distributor of BioLegend (San Diego, Calif., USA) which manufactured the antibody 8D4-8.

The amino acid sequence of a mouse monoclonal anti-IL-4 antibody (clone 8D4-8) was determined by a combination of Edman sequencing and mass spectrometry (Pham et al., 2006, Anal. Biochem. 352: 77-86; Roberts et al., 2005, Anal. Chem. 67: 3613-25). Briefly, the antibody was first separated into light and heavy chains and then each chain was cleaved by sequence specific proteases or chemically. Resulting peptides were separated by reverse phase chromatography and analyzed by Matrix-assisted laser desorption/ionization spectrometry (MALDI) and/or LC-MS/MS. Unique peptides as well as the intact heavy and light chains were than subjected to Edman sequencing for unambiguous determination of the protein sequence.

Example 3: Humanization of the Fv Domain of Mouse Anti-Human IL-13 Monoclonal Antibody Clone B-B13

The humanization protocol described hereinabove was used to humanize the B-B13 clone. Six humanized versions were suggested which include mutations in the CDRs to address problematic residues (deamidation site, solvent exposed methionine, acide labile positions).

The VL & VH sequences of B-B13 were blasted against the July 2007 version of the Protein Data Bank (PDB). The most similar light and heavy chain amino acid sequences were retrieved. The closest homologue for the variable light chain was found to be 1EGJ. The closest homologue for the heavy chain was found to be 1FNS. The structures 1EGJ & 1FNS were used to build up a homology model of the variable domains which was subsequently energy minimized using the standard procedure implemented in Molecular Operating Environment (MOE). MOE is a comprehensive suite of softwares for computer assisted drug design distributed by the Chemical Computing group. A molecular dynamic (MD) calculation of a 3D homology model of B-B13 was subsequently performed for 1.7 nanoseconds in Generalized Born implicit solvent. The resulting 1,700 snapshots from the MD trajectory were then used to calculate, for each B-B13 amino-acid, the distribution of its root mean square deviations (rmsd) compared to a reference medoid position. A statistical test, comparing the rmsd distribution of each amino-acid to the global rmsd distribution, is finally used to decide if the amino-acid is flexible enough, as seen during the MD, to be considered as likely to interact with B-cell receptors and responsible for activation of the immune response. The flexible positions of the murine B-B13 variable region were compared to the corresponding positions in human antibody sequences in the January 2007 version of the ImMunoGeneTics Database that has been downloaded locally. Only those residues which display flexibility greater than three times the mean and a few flanking residues that preserve the 3D structures of these flexible residues were retained for the search. The human antibody variable region with the most identical flexible residues, with special considerations given to positions that come within 5.0 Å of a CDR, was chosen to replace the murine the B-B13 antibody variable region flexible residues. A number of mutations in the CDRs were also included in the proposed versions to avoid problematic residues. The following motifs of sequences were considered: Asp-Pro (acide labile bond), Asn-X-Ser/Thr (glycosylation), Asn-Gly/Ser/Thr (deamidation site in exposed area), Met (oxidation in exposed area). The resulting humanized sequences were blasted for sequence similarity against UniProtKB/Swiss-Prot database providing confidence that reasonable assumption has been made. It was found that all sequences show high degree of similarity to number of human antibodies. In addition none of the sequences contains any known B- or T-cell epitope listed in the Immune Epitope Database and Analysis Resource (IEDB database).

Three versions for the heavy chain (H1, H2, H3) and three versions were suggested for the light chain (L1, L2, L3). The three versions of the light chain are derived from CAA83271.1 (Genebank accession number CAA83271). The L1 version has 4 mutations. The L2 version includes an additional mutation to remove a DP site (Pro99) in CDR3. L3 incorporates two additional mutations located in the CDRs when compared with L2 which are two presumed deamidation sites (N34Q, N96A). The H1, H2 and H3 versions of the heavy chain are derived from CAC39364.1 (Genebank accession number CAC39364). This template was not the top scoring template but it was the highest scoring template which did not contain sequence exhibiting high homology (>70%) with known immunogenic sequence. Version H contains 6 mutations and the H2 sequence incorporates two additional mutations to address three deamidation sites (N60A, N73T, and N83T). The sequential numbering of amino acidy reflects their natural order within the protein (N-terminus to C-terminus). H3 contains two additional mutations (Y100R & D106K) which were thought to improve potency. Six combinations of VL and VH variants were recommended for generation of humanized antibodies: VL1×VH1, VL2×VH2, VL1×VH3, VL3×VH1, VL3×VH2 and VL3×VH3. As shown in Table 1, the amino acid changes were made in humanized B-B13 VL and VH variants using the re-surfacing technology set forth in the detailed description section of the instant application. The left column indicates the original amino acids and their positions in the murine B-B13 mAb.

TABLE 1

| Light Chain (Sequential numbering) | (VL1) | (VL2) | (VL3) |
|---|---|---|---|
| Asn1 | Asp | Asp | Asp |
| Asn34 | Asn | Asn | Gln |
| Pro44 | Ala | Ala | Ala |
| Glu83 | Gln | Gln | Gln |
| Asp85 | Glu | Glu | Glu |
| Asn96 | Asn | Asn | Ala |
| Pro99 | Pro | Ser | Ser |
|  | 4 mutations | 5 mutations | 7 mutations |
| Heavy Chain | (VH1) | (VH2) | (VH3) |
| Gln1 | Glu | Glu | Glu |
| Ser15 | Gly | Gly | Gly |
| Gln16 | Gly | Gly | Gly |
| Asn60 | Asn | Ala | Ala |
| Ser61 | Asp | Asp | Asp |
| Asn73 | Asn | Ser | Ser |
| Lys81 | Glu | Glu | Glu |
| Asn83 | Asn | Thr | Thr |
| Gln86 | Arg | Arg | Arg |
| Tyr100 | Tyr | Tyr | Arg |
| Asp106 | Asp | Asp | Lys |
|  | 6 mutations | 9 mutations | 11 mutations |

Example 4: Humanization of the Fv Domain of Mouse Anti-Human IL-4 Monoclonal Antibody Clone 8D4-8

The humanization (resurfacing) technology described hereinabove was used to humanize the 8D4-8 clone. Two humanized versions were prepared. One version includes one mutation in the CDRs of the heavy chain which was thought to address a problematic residue (exposed acide labile positions).

The VL & VH sequences of 8D4-8 were blasted against the July 2007 version of the PDB. The most similar light and heavy chain amino acid sequences were retrieved. The closest homologue for the variable light chain is 1YDJ. The closest homologue for the heavy chain was found to be 1IQW. The structures 1YDJ & 1IQW were used to build to up a homology model of the variable domains which was subsequently energy minimized using the standard procedure implemented in MOE. A molecular dynamic (MD) calculation of a 3D homology model of 8D4-8 was subsequently performed for 1.7 nanoseconds in Generalized Born implicit solvent. The resulting 1,700 snapshots from the MD trajectory were then used to calculate, for each 8D4 amino-acid, the distribution of its root mean square deviations (rmsd) compared to a reference medoid position. A statistical test, comparing the rmsd distribution of each amino-acid to the global rmsd distribution, is finally used to decide if the amino-acid is flexible enough, as seen during the MD, to be considered as likely to interact with B-cell receptors and responsible for activation of the immune response. The flexible positions of the murine 8D4-8 variable region were compared to the corresponding positions in human antibody sequences in the January 2007 version of the ImMunoGeneTics Database that has been downloaded locally. Only those residues which display flexibility greater than three times the mean and a few flanking residues that preserve the 3D structures of these flexible residues were retained for the search. The human antibody variable region with the most identical flexible residues, with special considerations given to positions that come within 5.0 Å of a CDR, was chosen to replace the murine the 8D4-8 antibody variable region flexible residues. Eventually, some additional mutations were also made to avoid problematic residues. The following motifs of sequences were considered: Asp-Pro (acide labile bond), Asn-X-Ser/Thr (glycosylation), Asn-Gly/Ser/Thr (deamidation site in exposed area), Met (oxidation in exposed area). The only problematic residue found was a DP site in the CDR2 of the heavy chain. The resulting humanized sequences were blasted for sequence Two versions for the heavy chain (H1, 12) and one version for the light chain (L1) were suggested. The L version of the light chain is derived from BAC01676.1 (Genebank accession number BAC01676). The L version has 3 mutations. The H1 and H2 versions of the heavy chain are derived from BAC02418.1 (Genebank accession number BAC02418). Version H1 contains 9 mutations and the H2 version includes an additional mutation to remove a DP site (Pro53) in CDR2. Two combinations, VL1×VH1 and VL1×VH2, were prepared.

Table 2 shows the amino acid changes that were made in humanized 8D4-8 VL and VH variants using the humanization (re-surfacing) technology. The left column indicates the original amino acids and their positions in the murine 8D4-8 mAb.

TABLE 2

| Light Chain (Sequential numbering) | (VL1) | |
|---|---|---|
| Asn5 | Thr | |
| Leu15 | Val | |
| Ser39 | Lys | |
| | 3 mutations | |
| Heavy Chain | (VH1) | (VH2) |
| Gln10 | Glu | Glu |
| Arg13 | Lys | Lys |
| Thr16 | Ala | Ala |
| Pro53 | Pro | Ala |
| Lys65 | Gln | Gln |
| Asp66 | Gly | Gly |
| Arg74 | Glu | Glu |
| Ser76 | Thr | Thr |
| Leu93 | Val | Val |
| Thr118 | Leu | Leu |
| | 9 mutations | 10 mutations |

Example 5: Cloning and Generation of Chimeric Anti-IL-13 Clone B-B13 Monoclonal Antibody, a Chimeric Anti-IL-4 Clone 8D4-8 Monoclonal Antibody and Humanized Variants Amino acid sequences of the variable heavy and light chains of the anti-IL-13 clone B-B13 and the anti-IL-4 clone 8D4-8 were backtranslated into nucleotide sequence and generated respectively using a modified protocol of the overlap extension PCR (OE-PCR) described by Young L. and Dong Q. (Nucl. Acids Res. (2004), 32(7), e59). PCR products were cloned into the pCR®4-TOPO using the Invitrogen TOPO TA cloning kit (Cat #45-0641) and sequenced using M13 forward and M13 reverse primers. The variable domains were fused together to the constant heavy (IGHG1, Genebank accession number Q569F4) or light chain (IGKC) Genebank accession number Q502W4) respectively, digested with NheI and HindIII and each ligated into the NheI/HindIII sites of the episomal expression vector pXL, an analogon of the pTT vector described by Durocher et al. (2002), Nucl. Acids Res. 30(2), E9, creating the plasmids for the mammalian expression of the chimeric B-B13-heavy and light chains and the chimeric 8D4-8 heavy and light chains.

The expression clones encoding the humanized variants of the anti-IL-13 clone B-B13 and the anti-IL-4 clone 8D4-8 were also synthetically generated by overlap extension PCR (OE-PCR), based on the proposed amino acid exchanges of the original sequences.

The expression plasmids encoding the heavy and light chain of the antibody were propagated in E. coli DH5a. Plasmids used for transfection were prepared from E. coli using the Qiagen EndoFree Plasmid Mega Kit.

For transfection HEK293 FreeStyle cells (Invitrogen) were seeded at $3\times10^5$ cells/mL in 100 mL volume of serum-free FreeStyle medium (Invitrogen) in a 500 mL shaker flask. Cells were cultured in a 37° C. incubator with a humidified atmosphere of 8% $CO_2$, on an orbital shaker platform rotating at 110 rpm.

Three days post-seeding viable and total cell were determined with a CASY electronic cell counter (Schärfe System GmbH). Cells with viability greater than 90% were used for transfection at a cell density of 1-1.5×$10^6$ cells/mL. 100 mL cells were transfected in a 500 mL shaker flask with a mix of heavy and light chain expression plasmids ($5\times10^7$ μgDNA/cell) using FugeneHD (Roche) at a DNA:FugeneHD ratio of 2:7, at conditions described by the manufacturer. Transfected cells were cultured for 7 days in a 37° C. incubator (8% $CO_2$) on an orbital shaker platform rotating at 110 rpm.

A Nunc F96-MaxiSorp-Immuno plate was coated with goat anti-Human IgG (Fc specific) [NatuTec A80-104A]. The antibody was diluted to 10 ug/ml in carbonate coating buffer (50 mM sodium carbonate pH 9.6) and dispensed at 50 uL per well. The plate was sealed with adhesive tape, and stored overnight at 4 C. The plate was washed 3 times with Wash buffer (PBS pH 7.4 0.1% Tween20). 150 uL of blocking solution (1% BSA/PBS) was dispensed into each well to cover the plate. After 1 hour at RT the plate was washed 3 times with Wash buffer. 100 uL of sample or standards (in a range from 1500 ng/ml to 120 ng/ml) were added and let sit for 1 hour at RT. The plate was washed 3 times with Wash buffer. 100 uL of goat anti-Human IgG-FC-HRP conjugate [NatuTec A80-104P-60] diluted 1:10.000 were added using incubation solution (0.1% BSA, PBS pH 7.4, 0.05% Tween20). After 1 hour incubation at RT, the plate was washed 3 times with Wash buffer. 100 uL of ABTS substrate (10 mg ABTS tablet (Pierce 34026) in ml of 0.1 M $Na_2HPO_4$, 0.05 M citric acid solution, pH 5.0. Addition of 10 uL of 30% $H_2O_2$/10 ml Substrate buffer prior to use) were dispensed to each well, allow the color to develop. After the color has developed (approximately 10 to 15 minutes), 50 uL of 1% SDS Solution were added to stop the reaction. The plate was read at A405.

Proteins were purified by affinity chromatography on Protein A (HiTrap™ Protein A HP Columns, GE Life Sciences). After elution from the column with 100 mM acetate buffer with 100 mM NaCl pH 3.5, the monoclonal antibodies were formulated in PBS and 0.22 μm filtered. Protein concentration was determined by measurement of absorbance at 280 nm. Each batch was analyzed using a Protein 200 Plus LabChip kit on the Agilent 2100 bioanalyzer under reducing and non-reducing conditions to determine the purity and the molecular weight of each subunit and of the monomer.

Example 6: Characterization of Humanized Anti-IL-13 Clone B-B13 Variants and Humanized Anti-IL-4 Clone 8D4-8 Variants The reagents recombinant human IL-13 and IL-4 were purchased from Chemicon (USA). The Biacore kinetic analysis was performed as follows.

Surface plasmon resonance technology on a Biacore 3000 (GE Healthcare) was used for detailed kinetic characterisation of purified antibodies. A capture assay using a species specific antibody (e.g. human-Fc specific MAB 1302, Chemicon) for capture and orientation of the investigated antibodies was used. The capture antibody was immobilized via primary amine groups (10000 RU) on a research grade CM5 chip (GE Life Sciences) using standard procedures. The analysed antibody was captured with an adjusted RU value that would result in maximal analyte binding of 30 RU at a flow rate of 10 l/min. Binding kinetics were measured against recombinant human IL-4 and IL-13 over a concentration range between 0 to 50 nM in HBS EP (10 mM HEPES pH 7.4, 150 mM NaCl, 3 mM EDTA, 0.005% Surfactant P20) at a flow rate of 30 μl/min. Chip surfaces were regenerated with 10 mM glycine pH2.5. Kinetic parameters were analysed and calculated in the BIAevaluation program package using a flow cell without captured antibody as reference. To investigate additive binding of both antigens, a wizard-driven co-inject method has been applied in which one antigen was injected immediately followed by the antigen mix of IL-13/IL-4.

The antibodies of the present invention were measured for biological activity by measuring the inhibition of IL-4 or IL-13 mediated cell proliferation in TF-1 cells. Briefly, Applicants used IL-4 or IL-13 to stimulate the growth of TF-1 cells. TF-1 is a cell line that is dependent on cytokines for growth and responds to many cytokines including IL-4 and IL-13. The induced growth (compared to baseline conditions in the absence of cytokine) represents the biological activity of IL-4 or IL-13. Anti-IL-4, anti-IL-13 and bispecific anti-IL-4/IL-13 antibodies were shown to block IL-4 or IL-13 induced TF-1 cell growth. In addition, the bispecific anti-IL-4/IL-13 antibodies were shown to block TF-1 cell proliferation induced by combined IL-4 and IL-13 stimulation. The blocking effect was measured in a dose-dependent manner to generate IC50 (antibody concentration at 50% inhibition) as the antibody neutralization potency against its target, i.e., IL-4 or IL-13. Details of the methods employed are described in more detail below.

TF-1 cells (ATCC, CRL-2003) were maintained in complete medium (DMEM with high glucose, 25 mM Hepes buffer and glutamine, 10% FBS, 1×P/S, 1 mM sodium pyruvate) containing freshly added hGM-CSF at final concentration of 4 ng/ml. 24 hrs before IL-13 (15 ng/ml) or IL-4 (1 ng/ml) treatment. Cells were seeded in 96-well plates at 0.05×106/ml in complete medium without hGM-CSF. Serial dilutions of antibody with the corresponding cytokine were pre-incubated for 30 minutes at 37° C. before adding to cells. Cells were cultured for 72 hours (37° C., 5% CO2). MTS/PMS solution of cellTiter 96 Aqueous was added. The cells were then incubated for 3 hours. After that period, absorbance at 490 nm using a plate reader was recorded. IC50 values were calculated using Speed software.

The binding kinetics and neutralization activity of humanized B-B13 variants are shown in Table 3. (nt, not tested).

TABLE 3

| antibody | on-rate ($M^{-1} \times S^{-1}$) | off-rate ($S^{-1}$) | KD (M) | IC50 (M) |
| --- | --- | --- | --- | --- |
| Murine B-B13 | 8.64E+05 | 3.73E−04 | 5.63E−10 | Nt |
| chB-B13 WT | 1.76E+06 | 4.61E−04 | 2.61E−10 | 7.4E−9 |

TABLE 3-continued

| antibody | on-rate ($M^{-1} \times S^{-1}$) | off-rate ($S^{-1}$) | KD (M) | IC50 (M) |
| --- | --- | --- | --- | --- |
| huB-B13 VL1 × VH1 | 1.74E+06 | 6.91E−04 | 3.96E−10 | 1.57E−8 |
| huB-B13 VL1 × VH3 | 1.93E+06 | 3.95E−04 | 2.05E−10 | Nt |
| huB-B13 VL2 × VH2 | 1.13E+06 | 1.77E−04 | 1.57E−10 | Nt |
| huB-B13 VL3 × VH1 | 1.93E+06 | 3.33E−04 | 1.72E−10 | 5.2E−9 |
| huB-B13 VL3 × VH2 | 2.55E+06 | 1.12E−04 | 4.39E−11 | 3.2E−9 |
| huB-B13 VL3 × VH3 | 2.14E+06 | 4.05E−04 | 1.89E−10 | Nt |

One humanized B-B13 variant, huB-B13 VL3×VH2, has significantly higher affinity compared with the original murine B-B13 (13 fold) and chimeric B-B13 (6 fold). The improved affinity may lead to increased potency and efficacy when these humanized anti-IL-13 antibodies are used to treat asthma patients. In addition, the humanized antibodies may have reduced immunogenicity compared with the murine antibody or the to chimeric antibody when used in man.

The binding kinetics and neutralization activity of humanized 8D4-8 variants are shown in Table 4.

TABLE 4

| antibody | on-rate ($M^{-1} \times S^{-1}$) | off-rate ($S^{-1}$) | KD (M) | IC50 (M) |
| --- | --- | --- | --- | --- |
| murine 8D4-8 | 5.57E+06 | 2.17E−04 | 3.77E−11 | 9.7E−11 |
| ch8D4-8 WT | 2.49E+07 | 1.95E−04 | 7.83E−12 | 8.4E−11 |
| Hu8D4-8 VL1 × VH1 | 4.72E+07 | 1.55E−04 | 3.29E−12 | 4.1E−11 |
| Hu8D4-8 VL1 × VH2 | 2.57E+07 | 3.48E−04 | 1.39E−11 | 1.35E−10 |

One humanized 8D4-8 variant, hu8D4-8 VL1×VH1 has significantly higher affinity compared with the original murine 8D4-8 (11 fold) and chimeric 8D4-8 (2 fold). The improved affinity may lead to increased potency and efficacy when this humanized anti-TL-4 antibody is used to treat asthma patients. In addition, the humanized antibody may have reduced immunogenicity compared with the murine antibody or the chimeric antibody when used in man.

Example 7: Cloning and Generation of Humanized Anti-IL-4/IL-13 Bispecific Antibodies The format used for the expression of bispecific antibodies (BsAb) is an IgG variant of the dual domain double head format described in U.S. Pat. No. 5,989,830. In this format an IgG molecule is elongated at its N-terminus on the corresponding heavy and light chains, by an additional variable domain of a second antibody. Thus, the resulting IgG molecule is a heterotetramer composed of two heavy and two light chains. The heavy chains consist of two variables heavy domains (VH1-VH2) deriving from two different antibodies joined together by a linker composed of ten amino acids $(G4S)_2$ and fused to the IgG4 constant domain. The light chains consist of two variables light domains (VL1-VL2) deriving from two different antibodies joined together by a linker composed of ten amino acids $(G4S)_2$ and fused to the constant kappa region.

Sequences for the variable heavy and light domains of the 8D4-8 variants were generated by PCR introducing a BamHI restriction site (GGATCC) at their respective 5'-ends encoding a part of the (G4S)$_2$-(GGATCC)-8D4-8. The 3' sequence of the VH of the 8D4-8 humanized variants ended with an ApaI restriction site (encoding the first amino acids of the CH1 domain) for a later fusion to the IGHG4 sequence (Q569F4, with deletion of the terminal Lys and a double mutation S241P and L248E). The 3'-end of the VL8D4-8 ended with a BsiWI restriction site encoding the first two amino acids of the constant kappa chain for a later fusion to IGKC (Gene Bank Accession Number Q502W4).

Sequences for the variable heavy and light domains of the B-B13 variants were generated by PCR introducing a BamHI restriction site at their respective 3'-ends encoding a part of the (G4S)$_2$-(B-B13)-(GGA GGC GGA GGG TCC GGA GGC GGA GGATCC (SEQ ID NO: 7)). Both sequences for the VH and VL of the B-B13 variants were generated with a NheI restriction site at their respective 5'-ends, followed by an ATG start codon and a leader peptide encoding sequence.

The VH of B-B13 and 8D4-8 were fused together through their BamHI sites within the (G4S)$_2$ linker. The VL of B-B13 and 8D4-8 were fused to each other through their BamHI sites within the (G4S) linker. Hence the tandems of heavy and the light chains generated had the following composition.

Bispecific antibody heavy chain: NheI-Leader peptide-VH-B-B13-(G4S)$_2$-VH 8D4-8-ApaI.

Bispecific antibody light chain: NheI-Leader peptide-VL-B-B13-(G4S)$_2$-VL 8D4-8-BsiWI.

All intermediate PCR fragments were cloned into into the pCR®4-TOPO using the Invitrogen TOPO TA cloning kit (Cat #: 45-0641) and sequenced using M13 forward and M13 reverse primers.

After sequence validation the heavy chain tandems were fused through their ApaI site to the IGHG4 sequence and the variable light chain tandems were fused through their BsiWI site to IGKC. The created dual domain heavy chain and light chain were digested with NheI and HindIII and each ligated into the NheI/HindIII sites of the episomal expression vector pXL, creating the plasmids for mammalian expression of the TBTI-heavy and light chains respectively.

Four humanized bispecific anti-IL-4/anti-IL-13 constructs were generated based on the following combinations of humanized VH and VL versions of B-B13 and 8D4-8 as shown in Table 5.

TABLE 5

| Bispecific anti-IL-4/anti-IL-13 Ab | Anti-IL-13 Fv | Anti-IL-4 Fv |
|---|---|---|
| huTBTI3_1_1 | B-B13 VL3 × VH2 | 8D4-8 VL1 × VH2 |
| huTBTI3_2_1 | B-B13 VL3 × VH2 | 8D4-8 VL1 × VH1 |

TABLE 5-continued

| Bispecific anti-IL-4/anti-IL-13 Ab | Anti-IL-13 Fv | Anti-IL-4 Fv |
|---|---|---|
| huTBTI3_1_2 | B-B13 VL2 × VH2 | 8D4-8 VL1 × VH2 |
| huTBTI3_2_2 | B-B13 VL2 × VH2 | 8D4-8 VL1 × VH1 |

Example 8: Characterization of the Humanized Bispecific Antibodies

Binding and neutralization activity assays were performed as described in the previous Examples.

Table 6 depicts the binding kinetics of four humanized anti-IL-4/IL-13 antibody variants. All four constructs of bispecific antibodies binds to IL-4 and IL-13 with high affinities.

TABLE 6

| | IL-13 affinity | | | IL-4 affinity | | |
|---|---|---|---|---|---|---|
| BsAB | on-rate ($M^{-1} \times S^{-1}$) | off-rate ($S^{-1}$) | KD (M) | On-rate ($M^{-1} \times S^{-1}$) | off-rate ($S^{-1}$) | KD (M) |
| huTBTI3-1_1 | 2.27E+06 | 1.70E−04 | 7.47E−11 | 2.55E+06 | 3.78E−04 | 1.48E−10 |
| huTBTI3-2_1 | 2.17E+06 | 1.69E−04 | 7.80E−11 | 4.00E+06 | 1.39E−04 | 3.47E−11 |
| huTBTI3-1_2 | 8.50E+05 | 1.64E−04 | 1.93E−10 | 2.23E+06 | 3.08E−04 | 1.38E−10 |
| huTBTI3-2_2 | 8.20E+05 | 2.12E−04 | 2.59E−10 | 3.96E+06 | 1.32E−04 | 3.32E−11 |

The neutralization activity of humanized anti-IL-4/IL-13 bispecific antibody variants is summarized in Table 7. Both huTBTI3-1_1 and huTBTI3-2_1 completely neutralized IL-13 or IL-4 induced TF-1 cell proliferation with IC50 shown below.

TABLE 7

| Antibody | IC50 (nM) in IL-13 assay | IC50 (nM) in IL-4 assay |
|---|---|---|
| huTBTI3-1_1 | 3.7 | 1.7 |
| huTBTI3-2_1 | 4.1 | 0.32 |

It is well known that a mutant IL-13 allele is linked in high frequency with asthma (Heinzmann A. et al., 2000, Hum Mol Genet 9, 4, p 549-559). Therefore, the binding kinetics of the bispecific antibodies to the mutant IL-13 protein (human IL-13 R112Q variant, PeproTech, Rocky Hill, N.J., USA) was studied. The results indicated that the huTBTI3-1_1 and huTBTI3-2_1 bound to the IL-13 variant similarly to the wild type IL-13.

Table 8 shows the binding kinetics of humanized anti-IL-4 μL-13 molecules to mutant IL-13 protein.

TABLE 8

| | IL13 variant affinity | | |
|---|---|---|---|
| BsAB | on-rate ($M^{-1} \times S^{-1}$) | off-rate ($S^{-1}$) | KD (M) |
| huTBTI3-1_1 | 9.74E+05 | 1.18E−04 | 1.21E−10 |
| huTBTI3-2_1 | 9.48E+05 | 2.00E−04 | 2.11E−10 |

The invention claimed is:

1. An isolated humanized antibody or antibody fragment thereof that specifically binds IL-4, wherein the antibody or antibody fragment thereof comprises a light chain variable domain comprising CDRs having the amino acid sequences HASQNIDVWLS (SEQ ID NO: 14), KASNLHTG (SEQ ID NO: 15), and QQAHSYPFT (SEQ ID NO: 16) and a heavy chain variable domain comprising CDRs having the amino acid sequences GYSFTSYWIH (SEQ ID NO: 17), IDPSDGETR (SEQ ID NO: 18) and LKEYGNYDSFYFDV (SEQ ID NO: 19).

2. The antibody or antibody fragment thereof of claim 1, wherein the light chain variable domain comprises an amino acid sequence at least 95% identical to the amino acid sequence of SEQ ID NO:3 and the heavy chain variable domain comprises an amino acid sequence at least 95% identical to the amino acid sequence of SEQ ID NO:4.

3. The antibody or antibody fragment thereof of claim 2, wherein the light chain variable domain comprises the amino acid sequence of SEQ ID NO:3 and a heavy chain domain comprises the amino acid sequence of SEQ ID NO:4.

4. The antibody or antibody fragment thereof of claim 1, wherein the antibody or antibody fragment is an antibody comprising a heavy chain and a light chain, wherein the heavy chain comprises CH1, CH2 and CH3 domains of a constant region and the light chain comprises a CL domain of a constant region.

5. The antibody or antibody fragment thereof of claim 4, wherein the antibody is an IgG4 antibody.

6. A pharmaceutical composition comprising the antibody or antibody fragment of claim 1 and a pharmaceutically acceptable carrier.

* * * * *

SEQUENCE LISTING

<160> NUMBER OF SEQ ID NOS: 23

<210> SEQ ID NO 1
<211> LENGTH: 111
<212> TYPE: PRT
<213> ORGANISM: Artificial Sequence
<220> FEATURE:
<223> OTHER INFORMATION: humanized mouse/ mouse VL3 region

<400> SEQUENCE: 1

```
Asp Ile Val Leu Thr Gln Ser Pro Ala Ser Leu Ala Val Ser Leu Gly
1               5                  10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
            100                 105                 110
```

<210> SEQ ID NO 2
<211> LENGTH: 118
<212> TYPE: PRT
<213> ORGANISM: Artificial Sequence
<220> FEATURE:
<223> OTHER INFORMATION: humanized mouse/mouse VH2 region

<400> SEQUENCE: 2

```
Glu Val Gln Leu Lys Glu Ser Gly Pro Gly Leu Val Ala Pro Gly Gly
1               5                  10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser
        115
```

<210> SEQ ID NO 3
<211> LENGTH: 108
<212> TYPE: PRT
<213> ORGANISM: Artificial Sequence
<220> FEATURE:
<223> OTHER INFORMATION: humanized mouse/mouse VL1 region

<400> SEQUENCE: 3

```
Asp Ile Gln Met Thr Gln Ser Pro Ala Ser Leu Ser Val Ser Val Gly
1               5                  10                  15
```

```
Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg
            100                 105

<210> SEQ ID NO 4
<211> LENGTH: 124
<212> TYPE: PRT
<213> ORGANISM: Artificial Sequence
<220> FEATURE:
<223> OTHER INFORMATION: humanized mouse/mouse VH1 region

<400> SEQUENCE: 4

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
 50                  55                  60

Gln Gly Arg Ala Thr Leu Thr Val Asp Glu Ser Thr Ser Thr Ala Tyr
 65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 5
<211> LENGTH: 124
<212> TYPE: PRT
<213> ORGANISM: Artificial Sequence
<220> FEATURE:
<223> OTHER INFORMATION: humanized mouse/mouse VH2 region

<400> SEQUENCE: 5

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Ala Ser Asp Gly Glu Thr Arg Leu Asn Gln Arg Phe
 50                  55                  60

Gln Gly Arg Ala Thr Leu Thr Val Asp Glu Ser Thr Ser Thr Ala Tyr
 65                  70                  75                  80

Met Gln Leu Arg Ser Pro Thr Ser Glu Asp Ser Ala Val Tyr Tyr Cys
```

```
                    85                  90                  95
Thr Arg Leu Lys Glu Tyr Gly Asn Tyr Asp Ser Phe Tyr Phe Asp Val
                100                 105                 110

Trp Gly Ala Gly Thr Leu Val Thr Val Ser Ser Ala
        115                 120

<210> SEQ ID NO 6
<211> LENGTH: 10
<212> TYPE: PRT
<213> ORGANISM: Artificial Sequence
<220> FEATURE:
<223> OTHER INFORMATION: linker

<400> SEQUENCE: 6

Gly Gly Gly Gly Ser Gly Gly Gly Gly Ser
1               5                   10

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ggaggcggag ggtccggagg cggaggatcc                                           30

<210> SEQ ID NO 8
<211> LENGTH: 15
<212> TYPE: PRT
<213> ORGANISM: Artificial Sequence
<220> FEATURE:
<223> OTHER INFORMATION: hB-B13 VL3 CDR

<400> SEQUENCE: 8

Arg Ala Ser Glu Ser Val Asp Ser Tyr Gly Gln Ser Tyr Met His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: hB-B13 VL3 CDR

<400> SEQUENCE: 9

Leu Ala Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: hB-B13 VL3 CDR

<400> SEQUENCE: 10

Gln Gln Asn Ala Glu Asp Ser Arg Thr
1               5

<210> SEQ ID NO 11
<211> LENGTH: 10
<212> TYPE: PRT
<213> ORGANISM: Artificial Sequence
<220> FEATURE:
<223> OTHER INFORMATION: hB-B13 VH2 CDR
```

```
<400> SEQUENCE: 11

Gly Phe Ser Leu Thr Asp Ser Ser Ile Asn
1               5                   10

<210> SEQ ID NO 12
<211> LENGTH: 5
<212> TYPE: PRT
<213> ORGANISM: Artificial Sequence
<220> FEATURE:
<223> OTHER INFORMATION: hB-B13 VH2 CDR

<400> SEQUENCE: 12

Asp Gly Arg Ile Asp
1               5

<210> SEQ ID NO 13
<211> LENGTH: 10
<212> TYPE: PRT
<213> ORGANISM: Artificial Sequence
<220> FEATURE:
<223> OTHER INFORMATION: hB-B13 VH2 CDR

<400> SEQUENCE: 13

Asp Gly Tyr Phe Pro Tyr Ala Met Asp Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: h8D4-8 VL1 CDR

<400> SEQUENCE: 14

His Ala Ser Gln Asn Ile Asp Val Trp Leu Ser
1               5                   10

<210> SEQ ID NO 15
<211> LENGTH: 8
<212> TYPE: PRT
<213> ORGANISM: Artificial Sequence
<220> FEATURE:
<223> OTHER INFORMATION: h8D4-8 VL1 CDR

<400> SEQUENCE: 15

Lys Ala Ser Asn Leu His Thr Gly
1               5

<210> SEQ ID NO 16
<211> LENGTH: 9
<212> TYPE: PRT
<213> ORGANISM: Artificial Sequence
<220> FEATURE:
<223> OTHER INFORMATION: h8D4-8 VL1 CDR

<400> SEQUENCE: 16

Gln Gln Ala His Ser Tyr Pro Phe Thr
1               5

<210> SEQ ID NO 17
<211> LENGTH: 10
<212> TYPE: PRT
<213> ORGANISM: Artificial Sequence
<220> FEATURE:
<223> OTHER INFORMATION: h8D4-8 VH1 CDR
```

```
<400> SEQUENCE: 17

Gly Tyr Ser Phe Thr Ser Tyr Trp Ile His
1               5                   10

<210> SEQ ID NO 18
<211> LENGTH: 9
<212> TYPE: PRT
<213> ORGANISM: Artificial Sequence
<220> FEATURE:
<223> OTHER INFORMATION: h8D4-8 VH1 CDR

<400> SEQUENCE: 18

Ile Asp Pro Ser Asp Gly Glu Thr Arg
1               5

<210> SEQ ID NO 19
<211> LENGTH: 14
<212> TYPE: PRT
<213> ORGANISM: Artificial Sequence
<220> FEATURE:
<223> OTHER INFORMATION: h8D4-8 VH1 CDR

<400> SEQUENCE: 19

Leu Lys Glu Tyr Gly Asn Tyr Asp Ser Phe Tyr Phe Asp Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: h8D4-8 VH2 CDR

<400> SEQUENCE: 20

Gly Tyr Ser Phe Thr Ser Tyr Trp Ile His
1               5                   10

<210> SEQ ID NO 21
<211> LENGTH: 9
<212> TYPE: PRT
<213> ORGANISM: Artificial Sequence
<220> FEATURE:
<223> OTHER INFORMATION: h8D4-8 VH2 CDR

<400> SEQUENCE: 21

Ile Asp Ala Ser Asp Gly Glu Thr Arg
1               5

<210> SEQ ID NO 22
<211> LENGTH: 14
<212> TYPE: PRT
<213> ORGANISM: Artificial Sequence
<220> FEATURE:
<223> OTHER INFORMATION: h8D4-8 VH2 CDR

<400> SEQUENCE: 22

Leu Lys Glu Tyr Gly Asn Tyr Asp Ser Phe Tyr Phe Asp Val
1               5                   10

<210> SEQ ID NO 23
<211> LENGTH: 5
<212> TYPE: PRT
```

```
<213> ORGANISM: Artificial Sequence
<220> FEATURE:
<223> OTHER INFORMATION: linker

<400> SEQUENCE: 23

Gly Gly Gly Gly Ser
1               5
```